US010780069B2

(12) United States Patent
Monga et al.

(10) Patent No.: US 10,780,069 B2
(45) Date of Patent: Sep. 22, 2020

(54) USE OF GC-1 IN TRANSPLANT RELATED POPULATION

(71) Applicants: University of Pittsburgh—Of the Commonwealth System of Higher Education, Pittsburgh, PA (US); Università degli Studi di Cagliari, Cagliari (IT)

(72) Inventors: Satdarshan Pal Singh Monga, Wexford, PA (US); Amedeo Columbano, Selargius (IT)

(73) Assignees: University of Pittsburgh—Of the Commonwealth System of Higher Education, Pittsburgh, PA (US); Universitá degli Studi di Cagliari, Cagliari (IT)

( * ) Notice: Subject to any disclaimer, the term of this patent is extended or adjusted under 35 U.S.C. 154(b) by 0 days.

(21) Appl. No.: 15/980,645

(22) Filed: May 15, 2018

(65) Prior Publication Data

US 2018/0333378 A1 Nov. 22, 2018

Related U.S. Application Data

(60) Provisional application No. 62/508,114, filed on May 18, 2017.

(51) Int. Cl.
*A61K 31/192* (2006.01)
*A61K 9/00* (2006.01)

(52) U.S. Cl.
CPC .......... *A61K 31/192* (2013.01); *A61K 9/0019* (2013.01); *A61K 9/0053* (2013.01)

(58) Field of Classification Search
USPC ........................................................ 514/571
See application file for complete search history.

(56) References Cited

U.S. PATENT DOCUMENTS

2016/0081955 A1* 3/2016 Scanlan ............... A61K 31/192
514/571

OTHER PUBLICATIONS

Min et al. (FASEB Journal 31, 1, Supplement 805.4, Apr. 2017; IDS document 2 of IDS filed May 15, 2018) (Year: 2017).*
Brandhagen et al. (Liver Transplantation, 9, 2003, S16-S28). (Year: 2003).*
Gisbert et al. (Liver Transplantation and Surgery, 1997, 3, 416-422) (Year: 1997).*
Tancevski et al. (Recent Patents on Cardiovascular Drug Discovery, 2011, 6, 16-19). (Year: 2011).*
Taki-Eldin (European Surgical Research, 2012, 48, 139-153) (Year: 2012).*
Lopez-Fontal et al. (PLoS One, Jan. 2010, 5, e8710, pp. 1-10) (Year: 2010).*
Zachoval et. al., Journal of Hepatology 35 (2001) 35:86-91). (Year: 2001).*
Alvarado et al., "Thyroid hormone receptor ⊕ agonist induces ⊕-catenin-dependent hepatocyte proliferation in mice: Implications in hepatic regeneration," *Gene Expr.* 17(1): 19-34 (2016).
Min et al., "Thyroid receptor beta agonist reduces tumor burden in an established murine model of human hepatocellular cancer," *FASEB Journal* 31(1): Supplement 805.4 (Apr. 2017)(Abstract).
Columbano et al., "GC-1: A thyromimetic with multiple therapeutic applications in liver disease," *Gene Expression* 17: 264-275 (2017).
Columbano et al., "The thyroid hormone receptor-⊕ agonist GC-1 induces cell proliferation in rat liver and pancreas," *Endocrinology* 147(7): 3211-3218 (e-PUB Mar. 30, 2006).
Perra et al., "Thyroid hormone (T3) and TR⊕ agonist GC-1 inhibit/reverse nonalcoholic fatty liver in rats," *The FASEB Journal* 22: 2981-2989 (2008).
Eisener-Dorfman et al., "Cautionary insights on knockout mouse studies; the gene or not the gene?" *Brain Behav. Immun.* 23(3): 318-324 (Mar. 2009).
Hüsing et al, "Lipids in liver transplant recipients," *World Journal of Gastroenterology* 22(12): 3315-3324 (Mar. 28, 2016).
Madhwal et al, "Is liver transplantation a risk factor for cardiovascular disease? A meta-analysis of observational studies," *Liver Transplantation* 18: 1140-1146 (2012).
Speliotes et al., "Treatment of dyslipidemia in common liver diseases," *Clinical Gastroenterology and Hepatology* 16(8):1189-1196 (2018).

* cited by examiner

*Primary Examiner* — Marcos L Sznaidman
(74) *Attorney, Agent, or Firm* — Klarquist Sparkman, LLP

(57) ABSTRACT

Methods are disclosed for the use of GC-1 (sobetirome), a prodrug thereof, or a pharmaceutically acceptable salt or prodrug thereof to increase liver regeneration and healing in liver transplant donors and recipients.

20 Claims, 21 Drawing Sheets

FIG. 4A
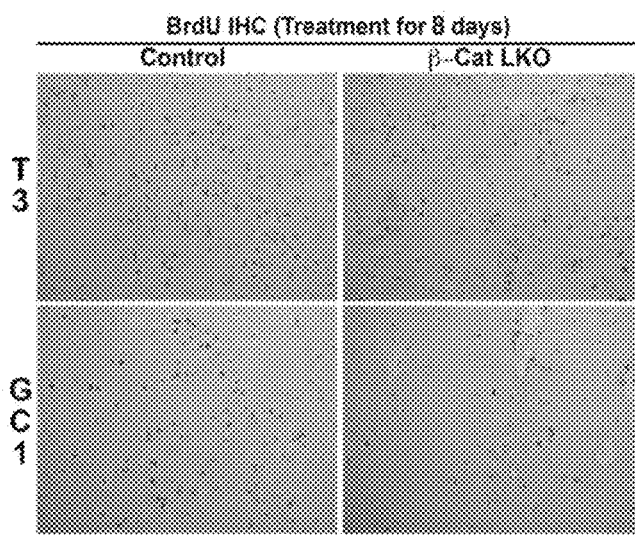
FIG. 4C Cyclin-D1 IHC (Treatment for 8 days)
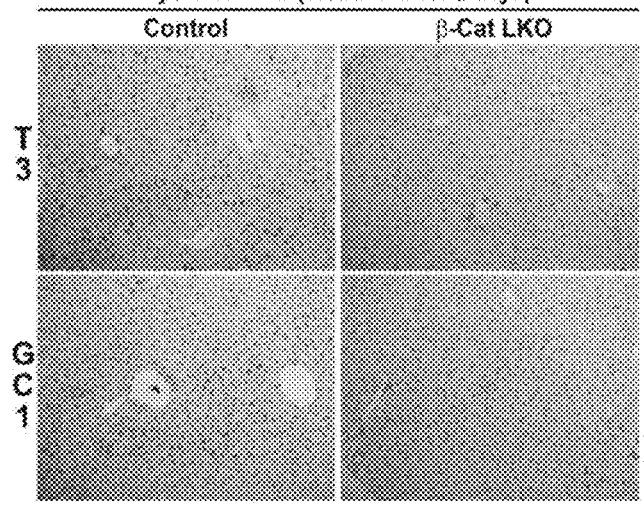
FIG. 4B
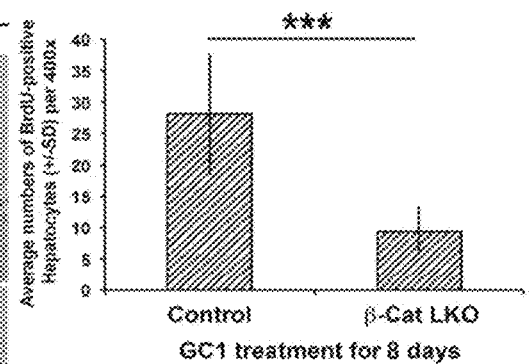
FIG. 4D
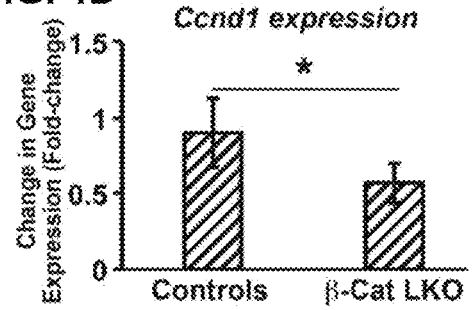
FIG. 4E
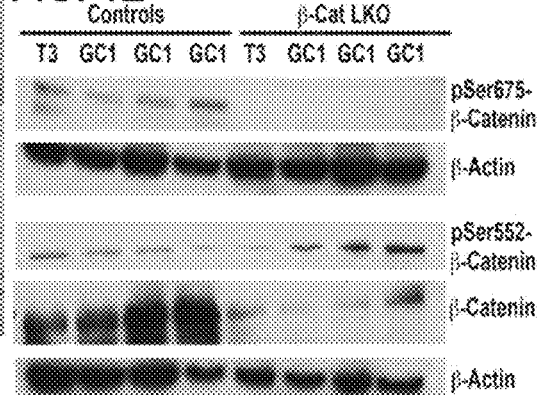

FIG. 5A
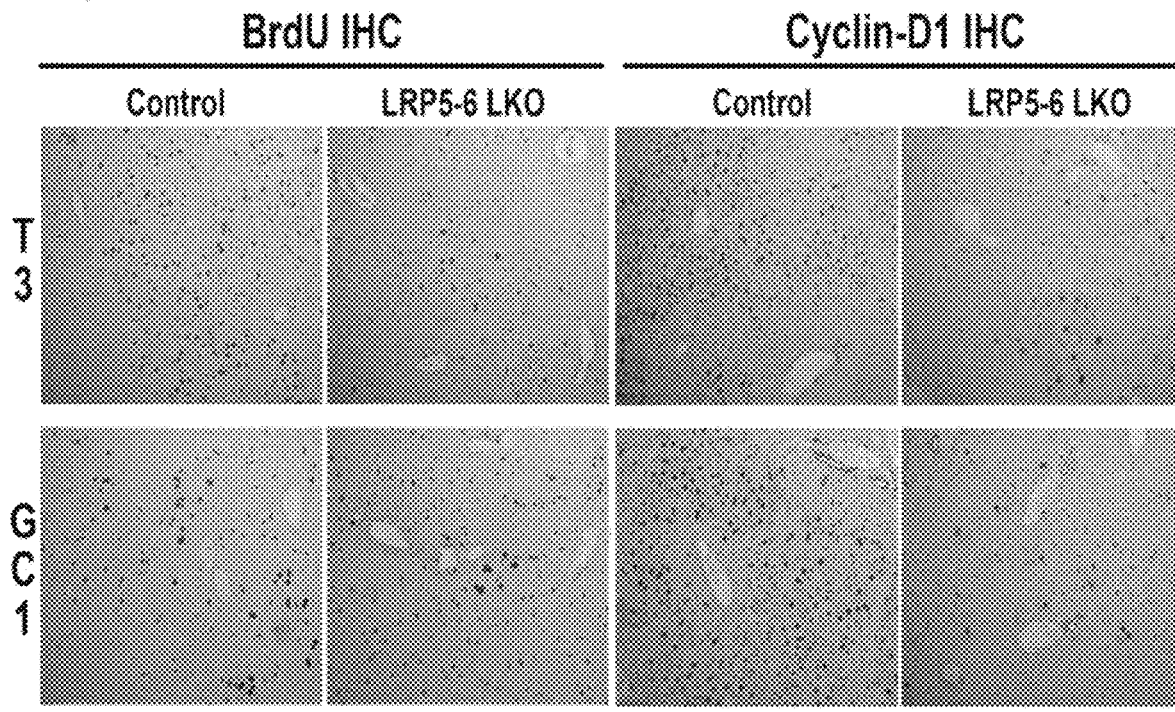
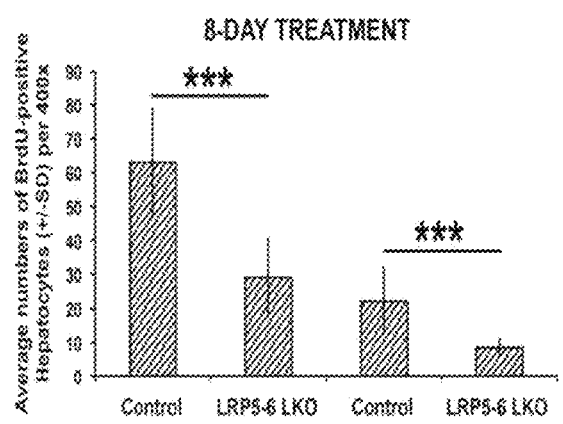
FIG. 5B
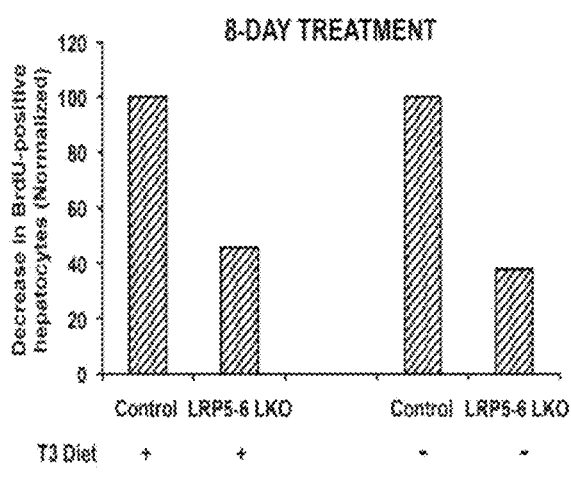
FIG. 5C

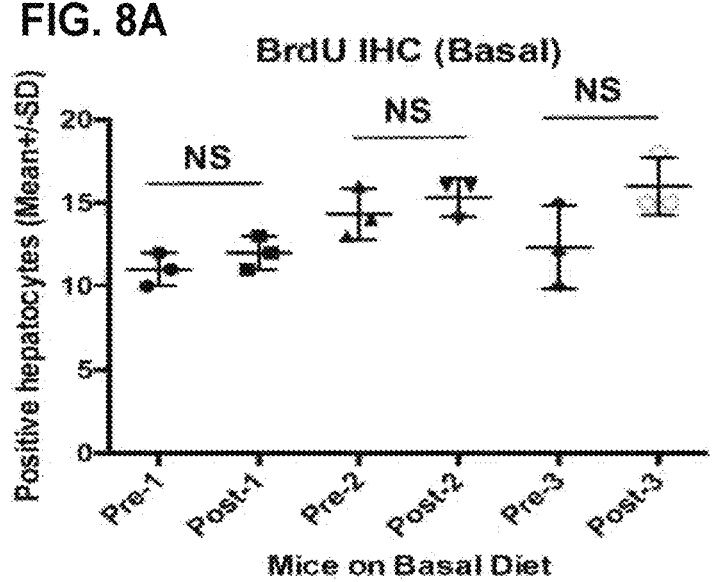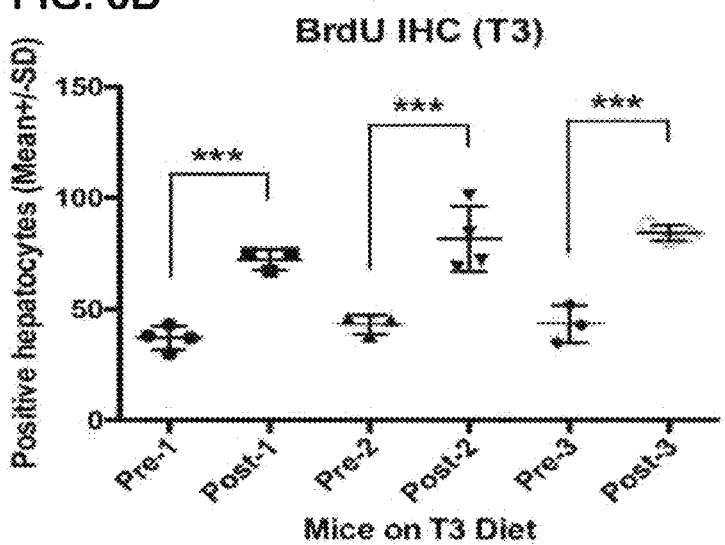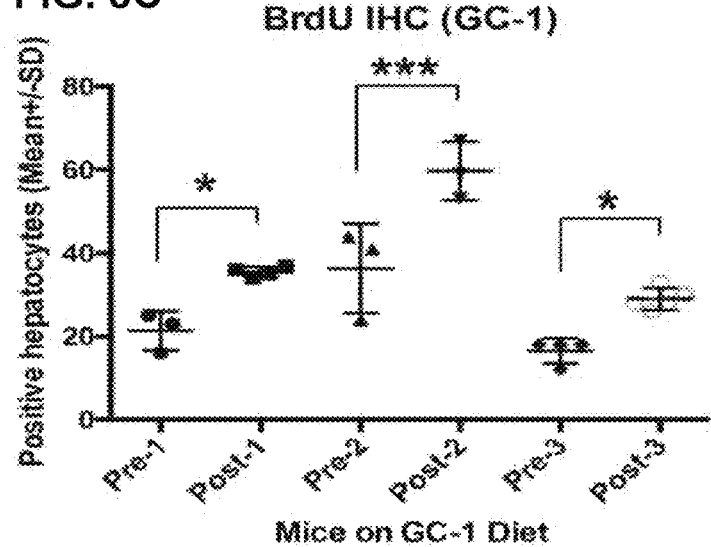

FIG. 11A
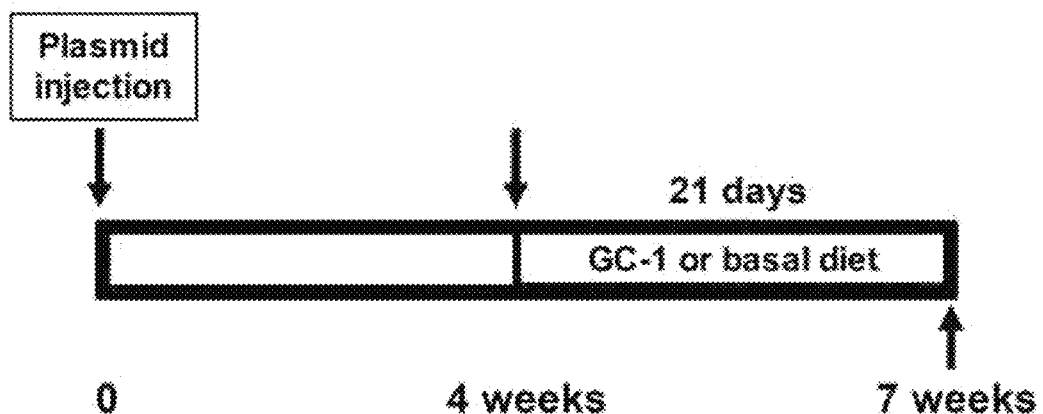
FIG. 11B
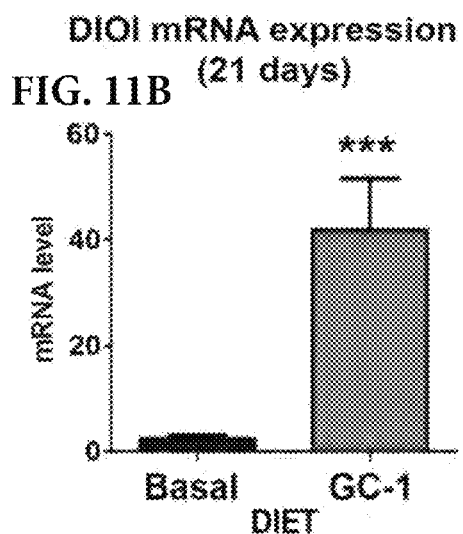
FIG. 11C
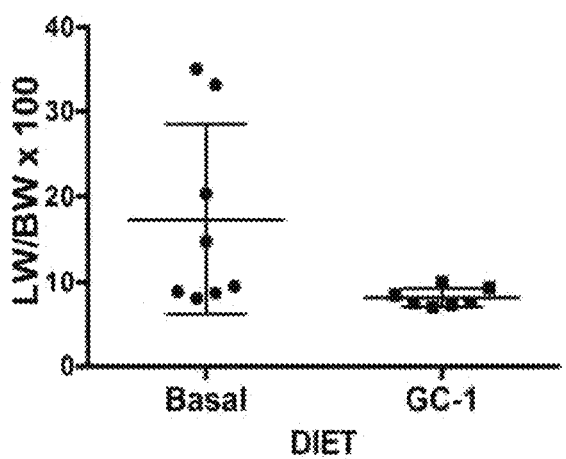
FIG. 11D
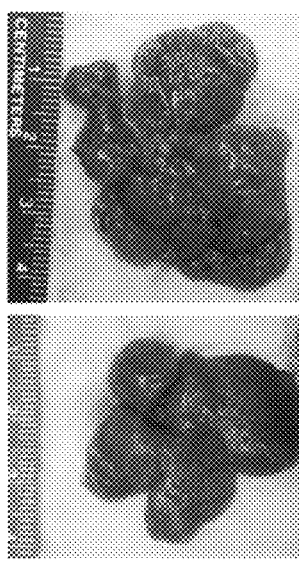
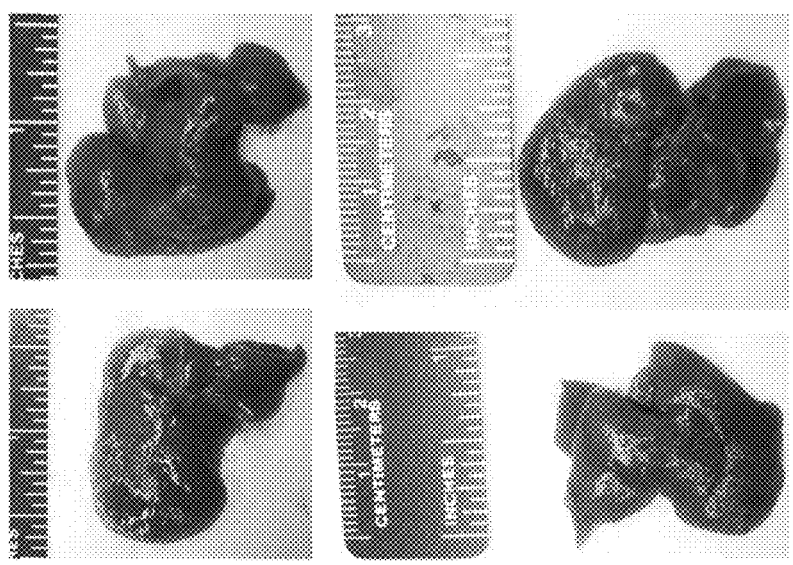

FIG. 16A
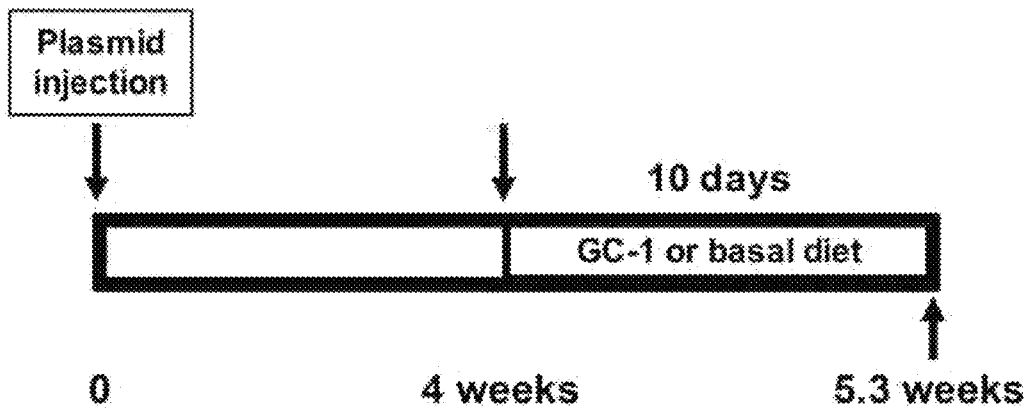
FIG. 16B DIOI mRNA expression (10 days)
FIG. 16C 10 days
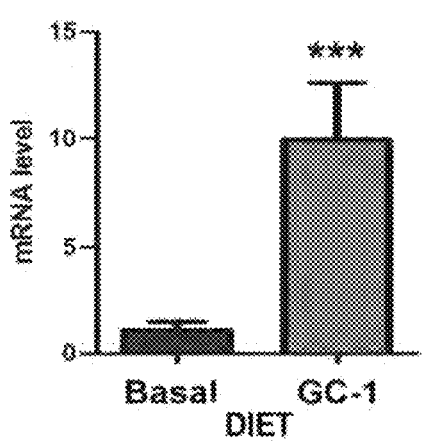
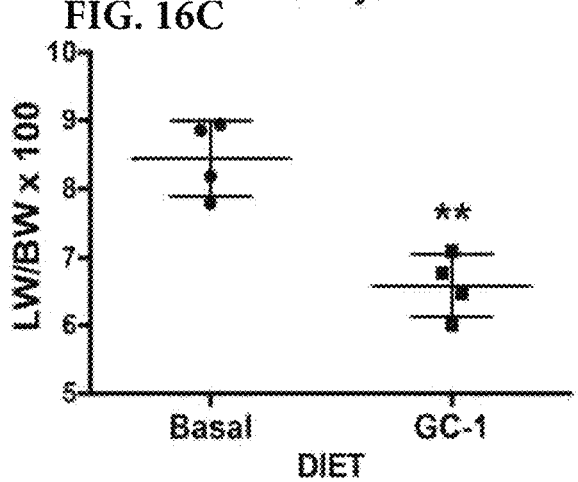
FIG. 16D Basal Diet (10 days) GC-1 Diet
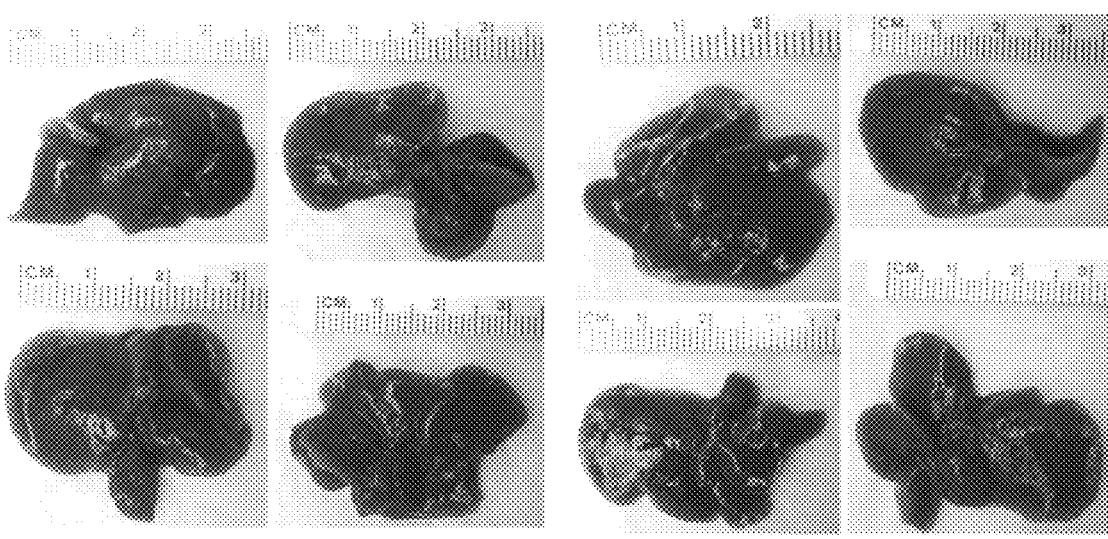

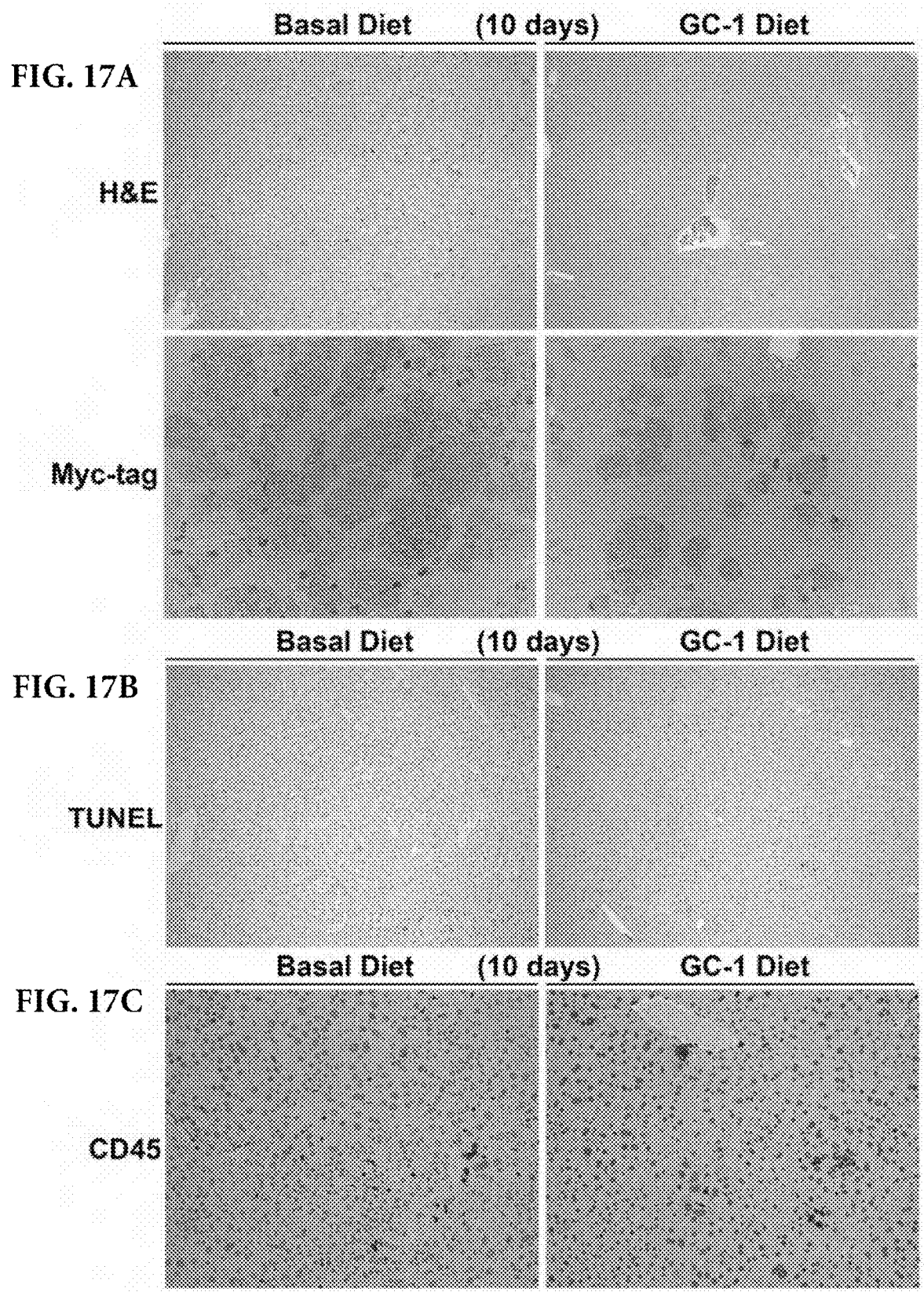

12
USE OF GC-1 IN TRANSPLANT RELATED POPULATION

CROSS REFERENCE TO RELATED APPLICATIONS

This claims the benefit of U.S. Provisional Application No. 62/508,114, filed May 18, 2017, which is incorporated herein by reference.

ACKNOWLEDGMENT OF GOVERNMENT SUPPORT

This invention was made with government support under grant nos. CA204586, DK062277 and DK100287 awarded by the National Institutes of Health. The government has certain rights in the invention.

FIELD

This disclosure concerns liver transplantation, specifically to the use of GC-1 (sobetirome), or prodrug thereof, or a pharmaceutically acceptable salt thereof, to increase liver regeneration and healing, such as in liver transplant donors and recipients.

BACKGROUND

The capacity of the liver to recover its size after resection has allowed extensive liver resection. However, post-hepatectomy liver failure (PHLF) remains one of the potential complications of liver resection. PHLF is defined as a post-operatively acquired deterioration in the ability of the liver to maintain its normal functions, and is one of the most life-threatening complications. The incidence of PHLF varies between 1.2% and 32%.

In PHLF there is a delicate balance between volume loss and excess growth, based on complex mechanisms. Several mechanisms for regeneration/regulation of liver size have been investigated, including cytokines, growth factors, and matrix remodeling. The main concern in clinical decision-making for management of patients with insufficient liver function involves whether the liver will maintain its size and function after surgical resection, such as when the subject is a liver donor. In this regard, the investigation of liver regeneration dynamics using factors routinely tested in the clinic represents an important issue in practical clinical settings. However, the need remains for treatment of PHLF.

Liver transplantation is a complex procedure that is performed at many health centers in the US, as well as numerous centers in Europe and other countries. The supply of liver allografts from non-living donors is lower than of the number of potential recipients, a reality that has spurred the development of living donor liver transplantation. An understanding of the molecular mechanisms of liver regeneration improves the survival rate of patients after surgical resection of large amounts of liver tissue. Liver regeneration is a well-regulated biological response to hepatocellular injury or loss involving a complex system of inflammatory, proliferative, and metabolic mechanisms and networks; an understanding of these pathways and agents that can modulate them will help improve the survival rate of patients after surgical resection of large amounts of liver tissue. Methods are needed to improve graft survival and increase liver function in both liver transplant recipients and liver donors.

SUMMARY

An improvement of the liver regenerative results in a reduction of the amount of liver tissue required for liver transplantation. Methods for increasing liver regeneration also reduce the risk for the donor and enhances the growth of the transplant within the recipient.

Methods are disclosed herein for increasing proliferation of hepatocytes. These methods include selecting a subject that is in need of increased proliferation of hepatocytes; and administering to the subject an effective amount of a pharmaceutical composition comprising GC-1 (sobetirome) or a pharmaceutically acceptable salt thereof, thereby increasing hepatocyte cell number. In some embodiments, a subject is selected for treatment that does not have a liver cancer, such as hepatocellular carcinoma. In some embodiments, the subject has a liver disease, such as cirrhosis. In further embodiments, the subject has an overdose, such as an acetaminophen overdose.

In some embodiments, methods are disclosed for increasing hepatocyte cell number in a liver transplant in a subject. These methods include selecting a subject that is the recipient of a liver transplant; and administering to the subject an effective amount of a pharmaceutical composition comprising GC-1 (sobetirome) or a pharmaceutically acceptable salt thereof, thereby increasing hepatocyte cell number in the liver transplant. In some non-limiting examples, the subject has small for size syndrome (SFSS). In other non-limiting examples, the subject is the recipient of a cadaveric liver transplant. In further non-limiting examples, the subject is the recipient of a liver transplant from a living donor.

In additional embodiments, methods are disclosed for increasing hepatocyte cell number in a liver donor. The methods include selecting a subject that is a liver donor, wherein the subject has donated a portion of their liver, and administering to the subject an effective amount of a pharmaceutical composition comprising GC-1 (sobetirome) or a pharmaceutically acceptable salt thereof. In some non-limiting examples, the subject is an older liver donor, such as a subject of greater than about 45 year old, such as, but not limited to, a subject about 45-55 years old.

In some embodiments, the GC-1 or the pharmaceutically acceptable salt thereof is administered intravenously to the subject, such as at a dose of 0.1 mg/kg to about 0.5 mg/kg. For example, the GC-1 or the pharmaceutically acceptable salt thereof is administered at a dose of 0.3 mg/kg. In other embodiments, the GC-1 or the pharmaceutically acceptable salt thereof is administered orally to the subject. In further embodiments, the GC-1 or the pharmaceutically acceptable salt thereof is administered within one day of a liver transplantation or resection procedure. In further embodiments the GC-1 or the pharmacologically acceptable salt thereof can be administered for about 7, 8, 9, 10, 11, 12, 13, or 14 days.

In other embodiments, the methods include measuring the metabolic function of the liver in the subject and/or measuring liver size in the subject and/or obtaining a lipid profile of the subject.

In further embodiments, the subject is human. In more embodiments, the subject has overdosed on acetaminophen.

The foregoing and other objects, features, and advantages of the invention will become more apparent from the following detailed description.

Nuclear cyclin-D1 was also increased in GC-1 treated mice. B. Western Blot of whole liver lysates showed increased Cyclin-D1 and pSer675-β-catenin in GC-1 treated mice compared with DMSO control. C. Bar graphs shows that the difference in ALT and bilirubin (BR) levels between the experimental groups and control animals were not significant (NS) and all values were within normal limits. D. Comparable normal hepatic histology in 8 days DMSO and GC-1-injected control mice (100×).

Figure 2A:
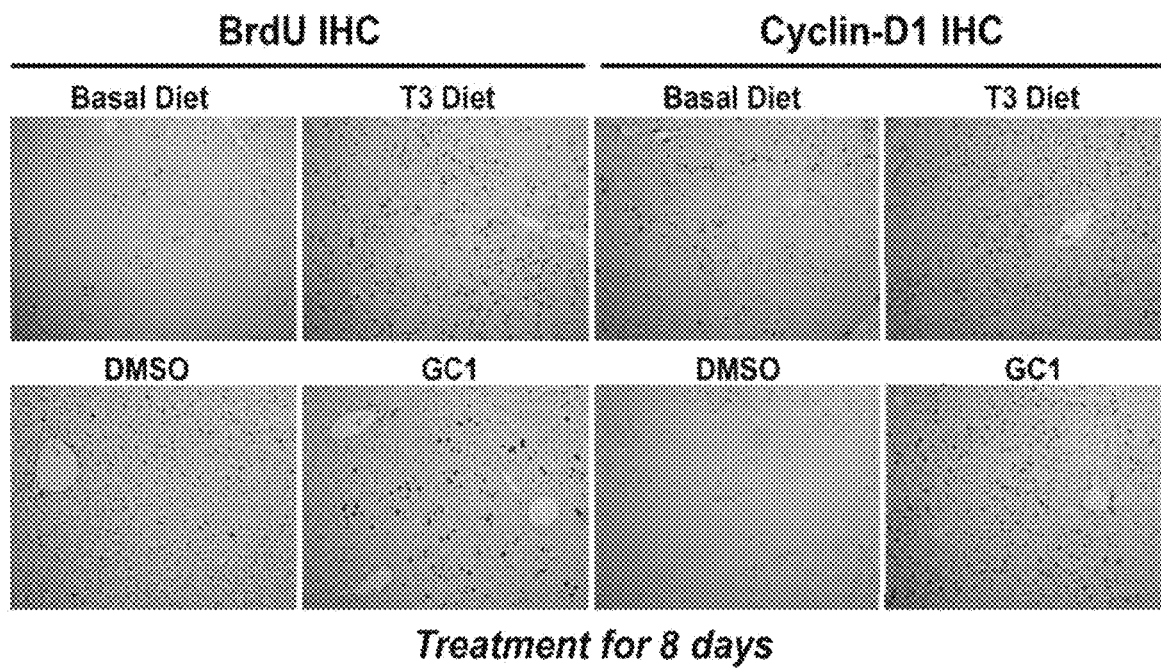
Figure 2B:
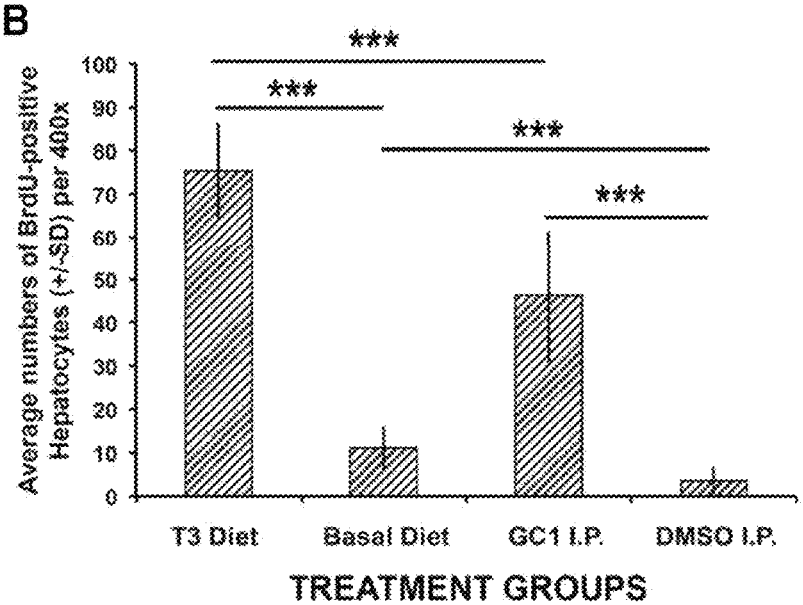

FIGS. 2A-2B. Comparison of T3 diet supplemented versus GC-1 injected mice. A. Immunohistochemistry for BrdU and Cyclin-D1 shows increased staining in T3 and GC-1 treatment groups when compared with respective controls. (100×). B. Bar graphs showing average number of BrdU positive hepatocyte nuclei per high power field (400×) in different conditions. Ten high power fields were counted for each group. T3 diet showed the highest proliferation when compared with basal diet and with GC-1 injections (*P<0.001). GC-1 showed increased proliferation when compared to DMSO injected controls (*P<0.001). DMSO injected controls had less baseline proliferation than basal diet fed animals with no other intervention (***P<0.001).

Figure 3A:
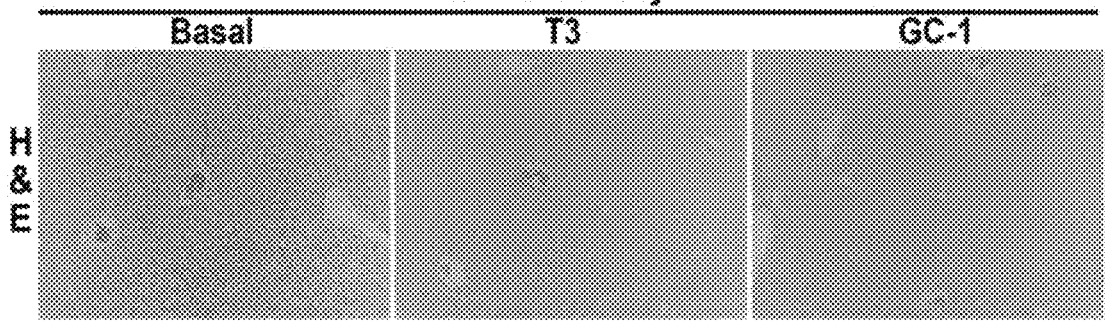
Figure 3B:
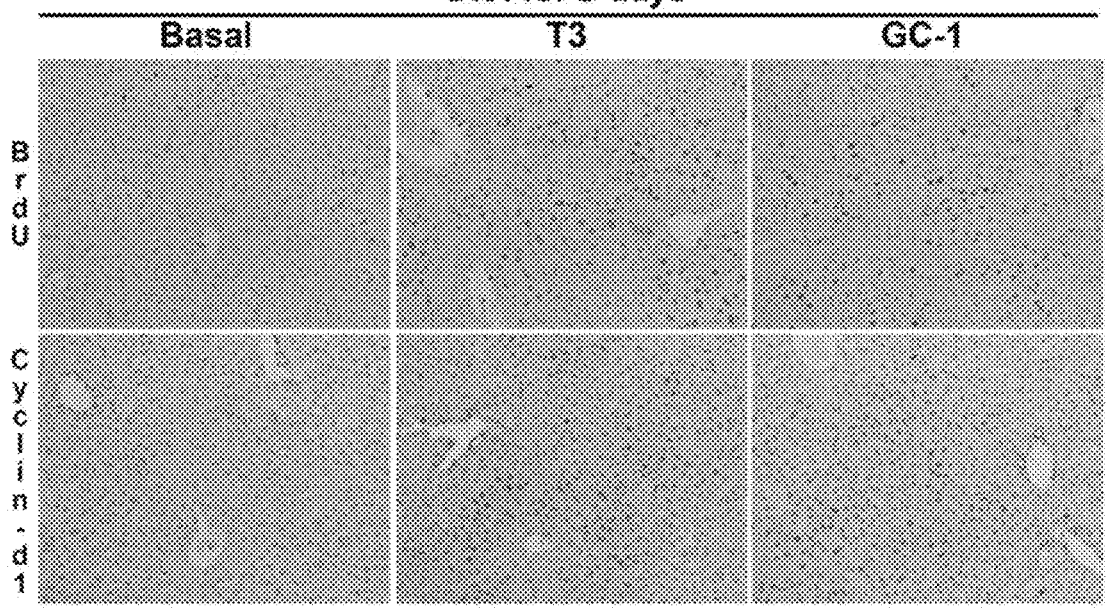
Figure 3C:
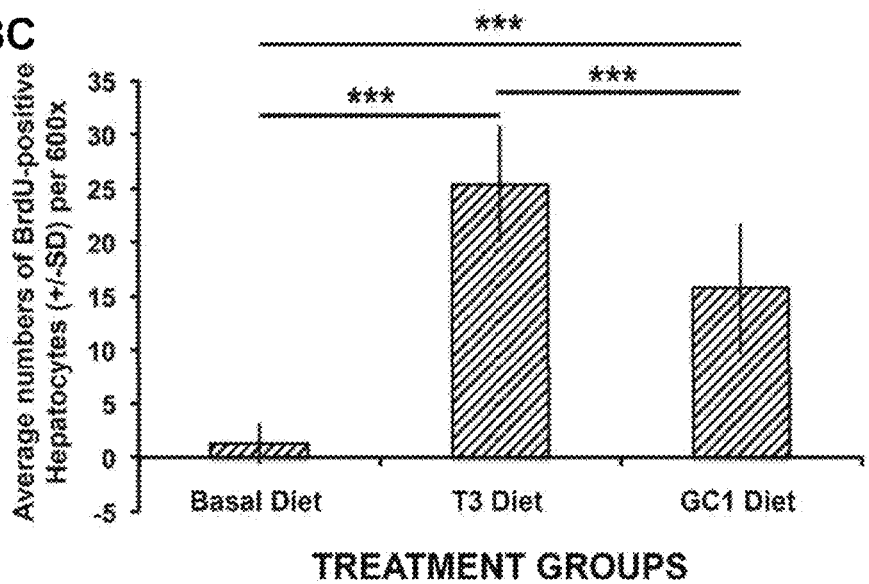

FIGS. 3A-3C. Increased hepatocyte proliferation in wild type mice fed T3 supplemented (4 mg/kg) and GC-1 supplemented (5 mg/kg) diet. A. Similar hepatic histology is observed in H&E stained sections in basal diet, T3- and GC-diet fed mice as shown in representative images from all three groups (100×). B. Immunohistochemistry shows increased BrdU incorporation and increased nuclear Cyclin D-1 in both T3 and GC-1 diet fed groups when compared to basal diet fed animals (100×). C. Bar graphs showing average number of BrdU positive hepatocyte nuclei per high power field (600×) in different conditions. Ten high power fields were counted for each group. T3 and GC-1 fed animals had significantly more BrdU-positive hepatocyte nuclei than basal diet GC-1 fed mice (*p<0.001). Interestingly, a significant difference in hepatocyte proliferation was also evident between the T3 and GC-1 diet fed mice (*p<0.001).

FIGS. 4A-4E. β-Catenin in hepatocytes is required for GC-1-induced hepatocyte proliferation A. Immunohistochemistry for BrdU shows decreased staining in T3 diet fed and GC-1 injected in β-catenin-LKO as compared to control mice. As shown in previous work, there is increased proliferation in control mice fed T3 diet. (100×). B. Bar graphs showing average number of BrdU positive hepatocyte nuclei per high power field (400×) in GC-1 injected β-catenin-LKO as compared to control mice. Total ten high power fields per group were counted. A significant difference in hepatocyte proliferation was observed between the two groups. (***p<0.001). C. Immunohistochemistry for Cycin-D1 shows increased staining in the livers of littermate control mice that received T3 or GC-1 as compared to notably less staining in β-catenin-LKO mice. (100×). D. Real-Time PCR shows significant decrease in mRNA expression of Cyclin-D1 in GC-1 injected 3-catenin-LKO mice as compared to littermate controls; (one tailed T-test, *p<0.05). E. Representative Western blots using liver lysates from β-catenin-LKO and controls after treatment with T3 or GC-1. As expected, β-catenin and pSer675β-catenin levels are absent or low. Interestingly, pSer552β-catenin levels are similar to wild type or slightly increased.

FIGS. 5A-5C. T3 and GC-1 induced proliferation is blunted in the absence of redundant Wnt co-receptors LRP5-6 in hepatocytes. A. BrdU and Cyclin-D1 immunohistochemistry shows decreased staining of hepatocytes in LRP5-6 LKO as compared to littermate controls in response to T3 and GC1 administration. Continued staining of smaller non-parenchymal cells is observed in controls and LRP5-6 LKO in response to T3 and GC-1 (100×). B. Bar graph shows a significant decrease in the number of hepatocytes displaying BrdU positive nuclei per HPF (400×) in the liver sections of LRP5-6 versus controls in response to T3 and GC-1 (***p<0.001). C. Normalizing BrdU counts to their respective controls show that LRP5-6 LKO show comparably reduced percentage of hepatocyte labeling in response to T3 and GC-1.

FIGS. 6A-6F. T3 and GC-1 induce β-catenin activation via both PKA and Wnt signaling. A. Representative Western blots showing comparable total β-catenin levels in liver lysates from controls and LRP5-6 administered T3 diet for 8 days. Despite increased levels of pSer675-β-catenin and pSer552-β-catenin, decreased Cyclin-D1 was evident in LRP5-6 LKO group. GAPDH and β-Actin were loading controls. B. Representative Western blots showing comparable total β-catenin levels in liver lysates from controls and LRP5-6 injected with GC-1 for 8 days. Despite comparably high levels of pSer675-β-catenin and even greater pSer552-β-catenin levels in LRP5-6 LKO liver lysates, Cyclin-D1 levels were notably lower in this group. Ponceau Red shows comparable loading in all lanes. C. Real-Time PCR shows reduced mRNA expression of Cyclin-D1 gene in the livers from GC-1 injected LRP5-6 LKO as compared to controls (one tailed T-test, *p<0.05). D. Western blot shows comparable levels of TCF4 in the liver lysates of LRP5-6 LKO and littermate control livers. GAPDH shows equal loading in all lanes. E. Representative Western blot shows 8 days of GC-1 diet fed animals leads to notably increased levels of active β-catenin (upper panel-darker exposure; lower panel-lighter exposure). Liver lysates from T3 or GC-1 administered 3-Cat LKO show very low levels of active β-catenin, presumably from the non-parenchymal cells. GAPDH represents comparable loading in all lanes. F. Representative Western blot shows notable increase in active β-catenin levels in liver lysates from control littermates administered T3 or GC-1 for 8 days as compared to basal diet. However, comparable levels of active β-catenin were observed in LRP5-6 LKO liver lysates fed basal diet or administered T3 or GC-1 diet for 8 days. GAPDH depicts equal loading in each lane.

Figure 7A:
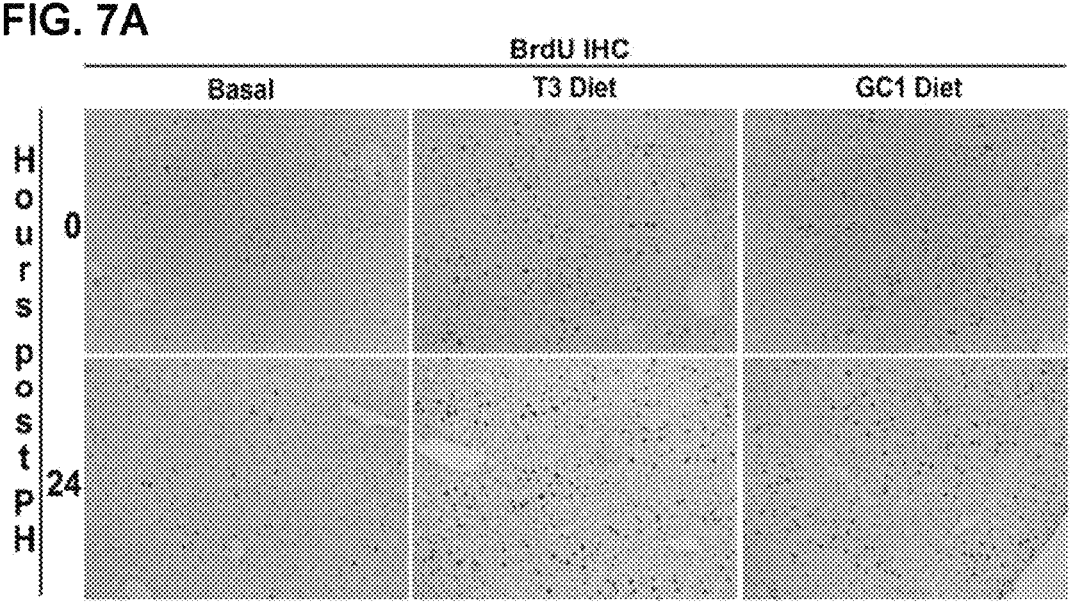
Figure 7B:
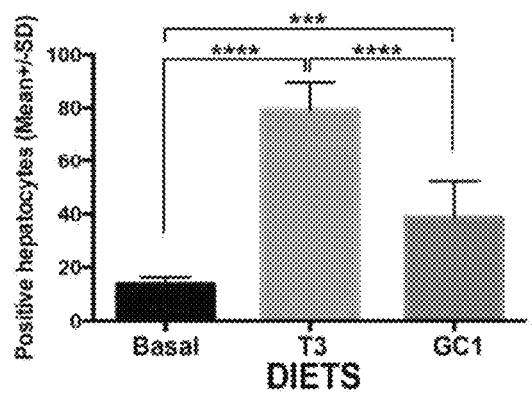
Figure 7C:
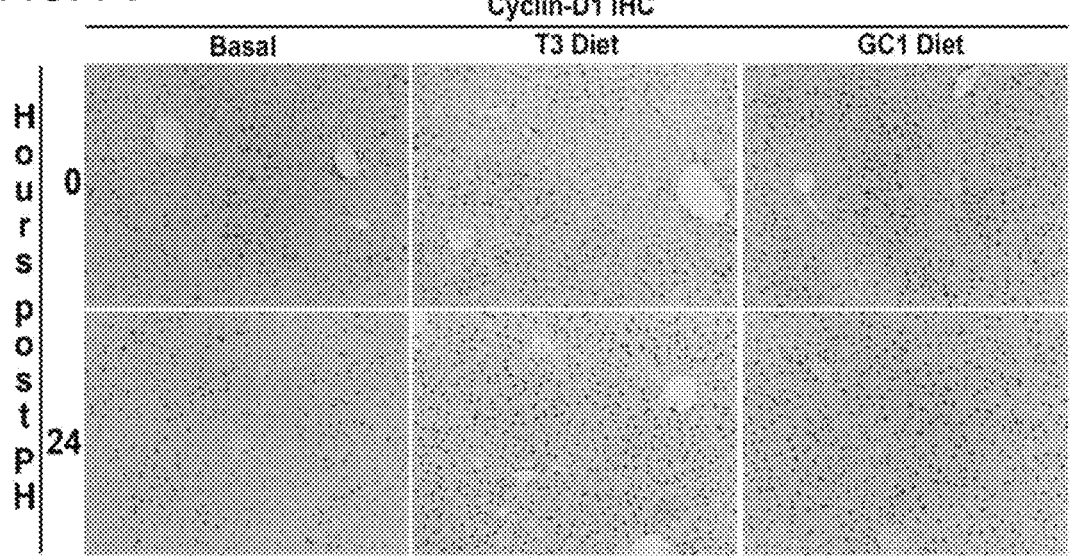

FIGS. 7A-7C. Increased hepatocyte proliferation and Cyclin-D1 expression after partial hepatectomy in mice pre-treated with T3 or GC-1 supplemented diet for 8 days. A. Immunohistochemistry for BrdU shows increased numbers of hepatocyte staining positive after 8 days of T3 or GC-1 feeding ad libitum as compared to mice fed basal diet. The analysis was carried out in lobes that were surgically removed at the time of hepatectomy (Time 0). A further increase in BrdU staining was evident in regenerating livers at 24 hours in animals that were maintained on T3 or GC-1 diet post-surgery as compared to the group fed basal diet after surgery. (100×). B. Bar graph shows a significant increase in the number of BrdU positive hepatocytes at 24 hours after hepatectomy in the control diet fed group versus T3 diet (**p<0.0001) and control diet fed versus GC-1 diet fed group (*p<0.001). Further, significant difference was also observed between T3- and GC-1-fed group (****p<0.0001). C. Immunohistochemistry for Cyclin-D1 shows increased numbers of hepatocyte staining positive after 8 days of T3 or GC-1 feeding ad libitum as compared to mice fed basal diet. The analysis was carried in lobes that were surgically removed at the time of hepatectomy (Time 0). A further increase in Cyclin-D1 staining was evident in regenerating livers at 24 hours in animals that were maintained on T3 or GC-1 diet post-surgery as compared to the group fed basal diet after surgery (100×).

FIGS. 8A-8C. Increased hepatocyte proliferation after partial hepatectomy in mice pre-treated with T3 or GC-1 supplemented diet for 8 days. A. Bar graph showing no significant (NS) differences in the average number of number of BrdU-positive hepatocytes per 100× field in liver sections in three independent mice on basal diet at the time of hepatectomy (Pre-1-3) versus at 24 hours after hepatectomy in the same animals (Post-1-3). B. Bar graph showing significant differences (***p<0.001) in the average number of number of BrdU-positive hepatocytes per 100× field in liver sections in three independent mice on T3 diet at the time of hepatectomy (Pre-1-3) versus at 24 hours after hepatectomy in the same animals (Post-1-3). C. Bar graph showing significant differences (*p<0.05; ***p<0.001) in the average number of number of BrdU-positive hepatocytes per 100× field in liver sections in three independent mice on GC-1 diet at the time of hepatectomy (Pre-1-3) versus at 24 hours after hepatectomy in the same animals (Post-1-3).

Figure 9:
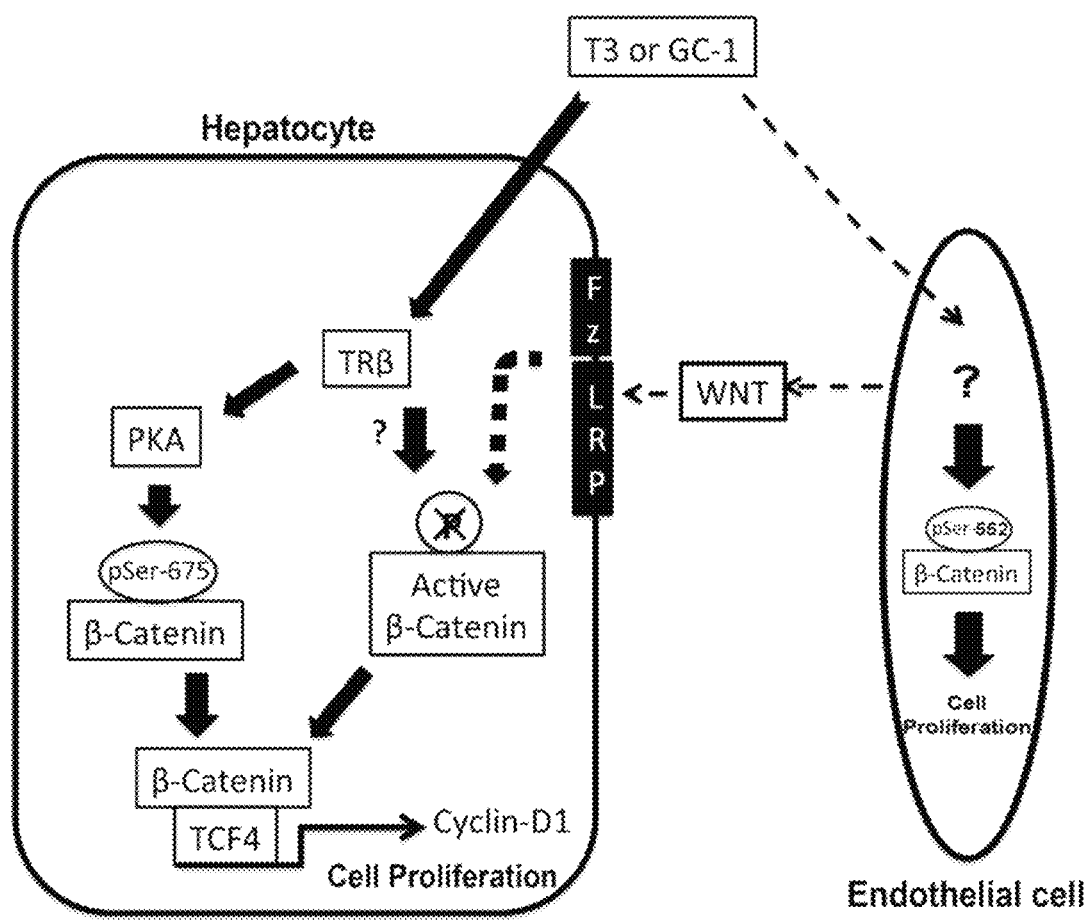
Figure 10A:
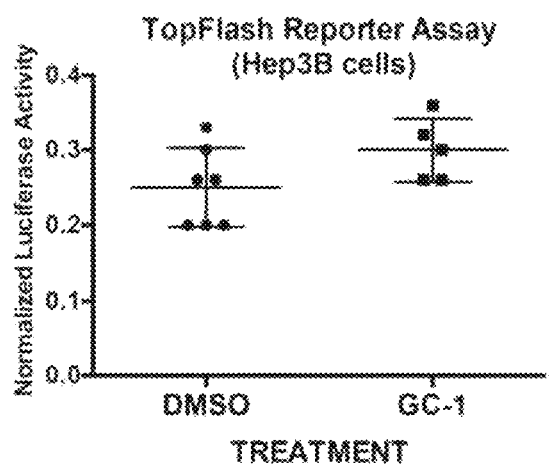
Figure 10B:
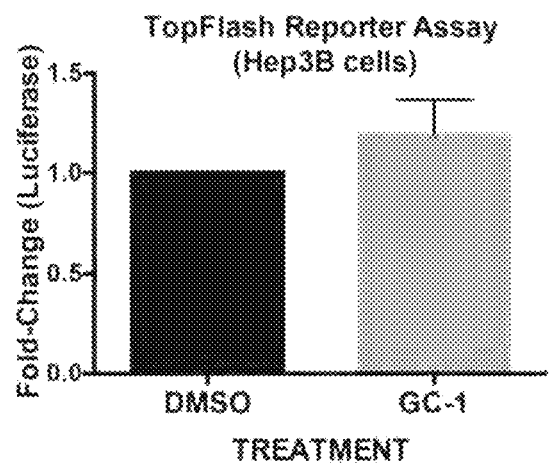
Figure 10C:
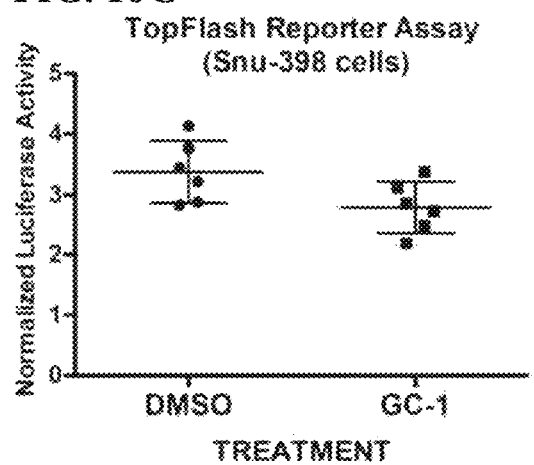
Figure 10D:
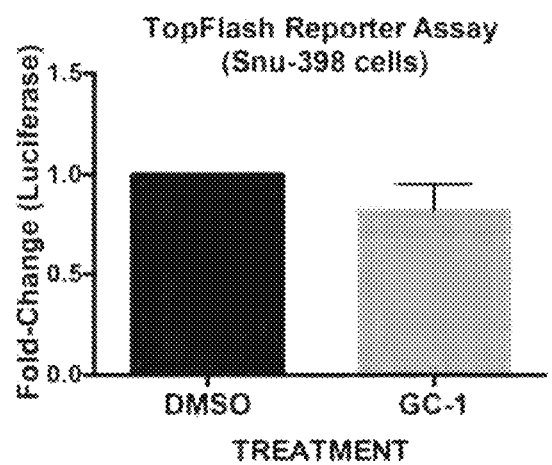
Figure 10E:
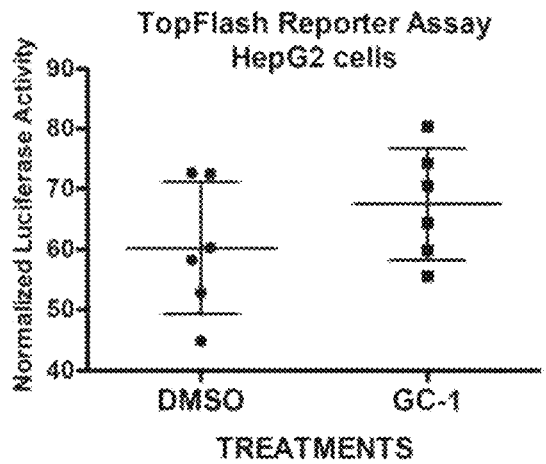
Figure 10F:
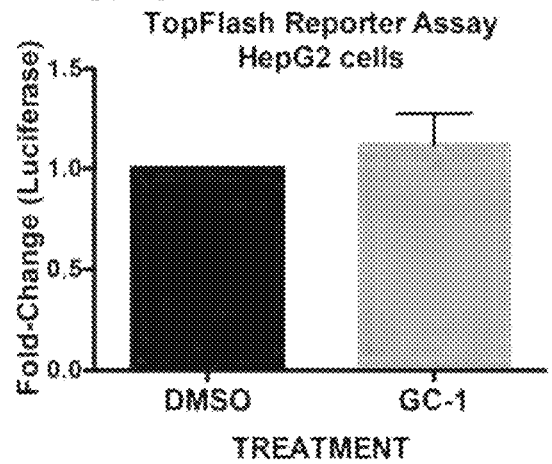

FIG. 9. Mechanism of T3/GC-1 induced β-catenin activation leading to Cyclin-D1 expression and cell proliferation. In hepatocytes, T3/GC-1 appears to activate β-catenin via PKA-dependent mechanism as well as through canonical Wnt signaling. It is likely that T3/GC-1 may induce β-catenin activation in endothelial cells to induce cell proliferation and also may stimulate Wnt release to activate β-catenin in hepatocytes in a paracrine fashion.

FIGS. 10A-10F. GC-1 does not influence β-catenin-TCF4 activity as evident by TopFlash reporter assay in liver tumor cell lines. (A) Bar graph shows insignificant differences in TopFlash luciferase reporter activity in Hep3B cells (have wild-type CTNNB1 gene) treated with DMSO or 7 μM GC-1. Each well for the treatment groups, is indicated by a closed circle (DMSO) or box (GC-1).-10F. (B) Lack of TopFlash reporter response to GC-1 in Hep3B cells is depicted as fold-change to DMSO treatment. (C) Bar graph shows insignificant differences in TopFlash luciferase reporter activity in Snu-389 cells (have exon-3 point mutant-CTNNB1 gene) treated with DMSO or 7 μM GC-1. Each well for the treatment groups, is indicated by a closed circle (DMSO) or box (GC-1). (D) Lack of TopFlash reporter response to GC-1 in Snu-398 cells is depicted as fold-change to DMSO treatment. (E) Bar graph shows insignificant differences in TopFlash luciferase reporter activity in HepG2 cells (have exon-3 deletion mutant-CTNNB1 gene) treated with DMSO or 71 μM GC-1. Each well for the treatment groups, is indicated by a closed circle (DMSO) or box (GC-1). (F) Lack of TopFlash reporter response to GC-1 in HepG2 cells is depicted as fold-change to DMSO treatment.

FIGS. 11A-11D: hMet-mutant-β-catenin injected mice fed GC-1 diet for 3 weeks, develop lesser HCC than controls. (A) Schematic showing the timing of GC-1 or basal diet administration and animal sacrifice in reference to the HTVI of SBTT plasmids. (B) RT-PCR using RNA isolated from livers shows around 40-fold increase in gene expression of deiodinase after 21-days of GC-1-diet as compared to basal diet. (***p<0.001). (C) An almost significant (p=0.0506) difference in liver weight/body weight (LW/BW×100) is observed after 21-days of GC-1-diet (n=7) as compared to basal diet (n=8) suggesting a decrease in tumor burden. Individual animals in each group are indicated by a closed circle or box. (D) Representative gross liver images from 21-days of GC-1 versus basal diet fed animals show lesser nodularity and tumor burden in GC-1 group.

FIGS. 12A-12D. Decreased tumor size in hMet-mutant-β-catenin model following 21-days of GC-1 reflected by histology and reduced Myc-tag, without any change in cell death. (A) Representative H&E stained sections show relatively fewer and smaller microscopic hepatic tumor nodules in GC-1 treated group at 21 days (50×). (B) Representative IHC for Myc-tag shows smaller hepatic tumor nodules at 21-days of GC-1 treatment versus controls (50×). (C) Representative WB shows a modest decrease in overall levels of Myc-tag which supports an overall lower tumor burden after 21 days of GC-1 treatment. GAPDH shows comparable loading. (D) A modestly higher number of TUNEL-positive nuclei within the tumor foci were evident in the control diet-fed group versus GC-1-diet-fed mice, likely due to larger size of tumor nodules (50×).

Figure 13A:
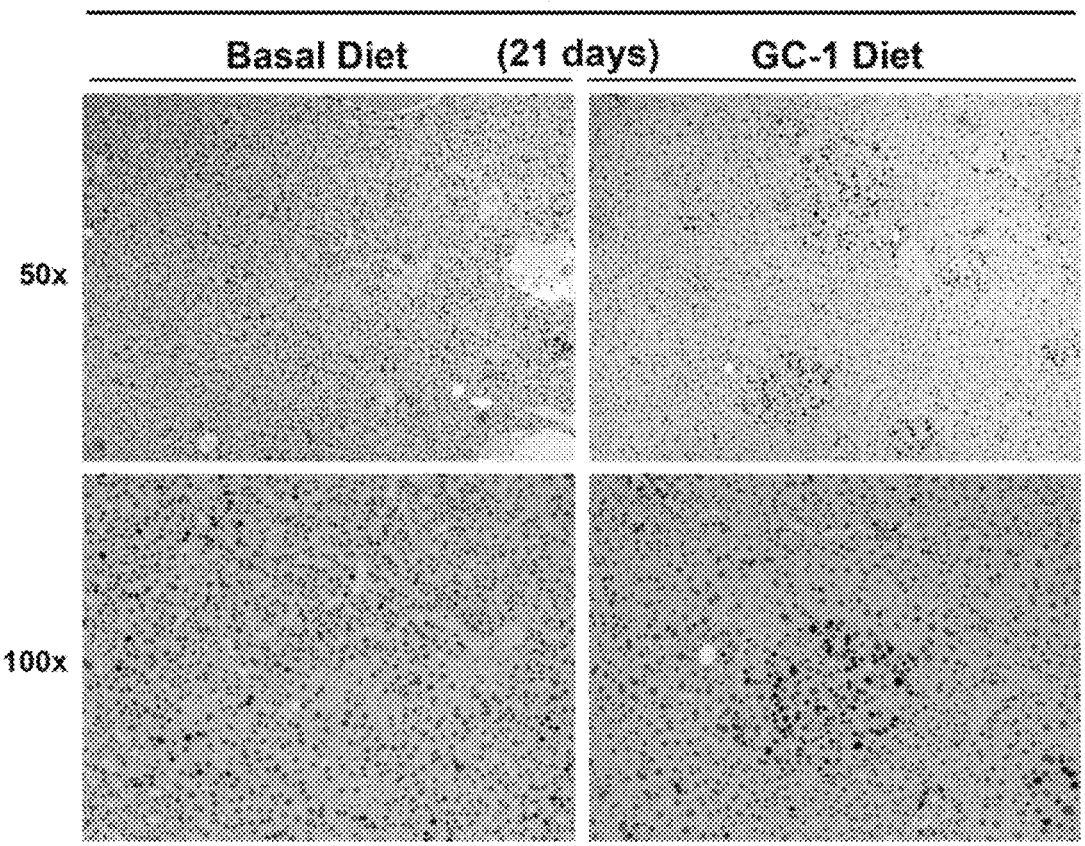
Figure 13B:
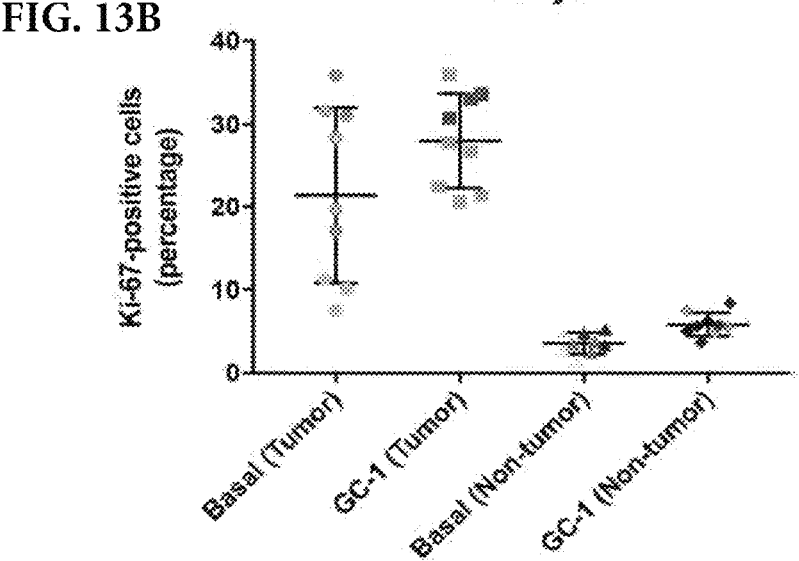

FIGS. 13A-13B. Continued proliferation in smaller tumor nodules following 21-days of GC-1 treatment as shown by numbers of cells in S-phase. (A) Scattered Ki-67 positive cells in large tumor nodules in liver sections of basal diet fed mice. While tumor nodules were smaller in GC-1 treated group, several cells continued to be Ki-67-positive cells within tumor foci (50×). (B) Quantification of Ki-67 staining shows comparable percentage of Ki-67-positive tumor cells within foci in control diet and GC-1 diet fed mice. Non-tumor tissues in both groups also showed insignificant differences in Ki-67 positivity.

Figure 14A:
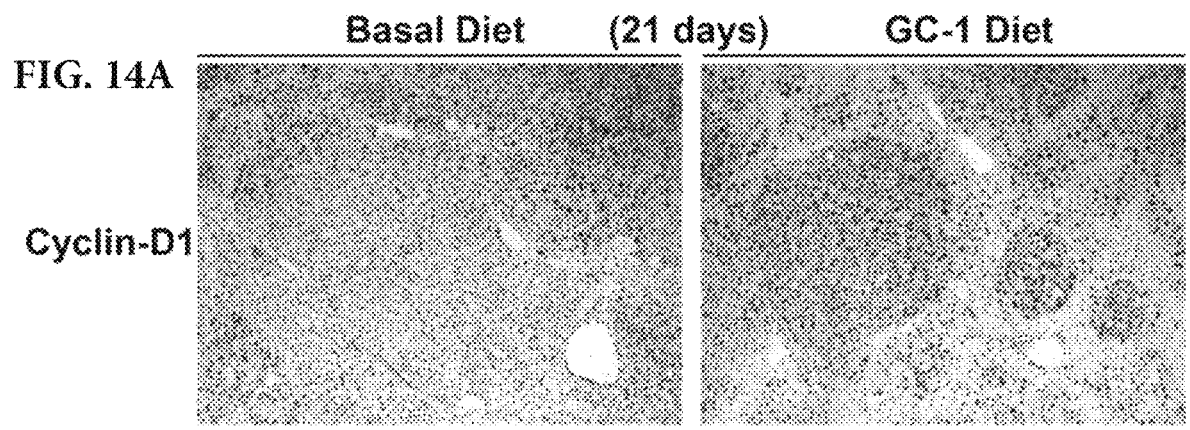
Figure 14B:
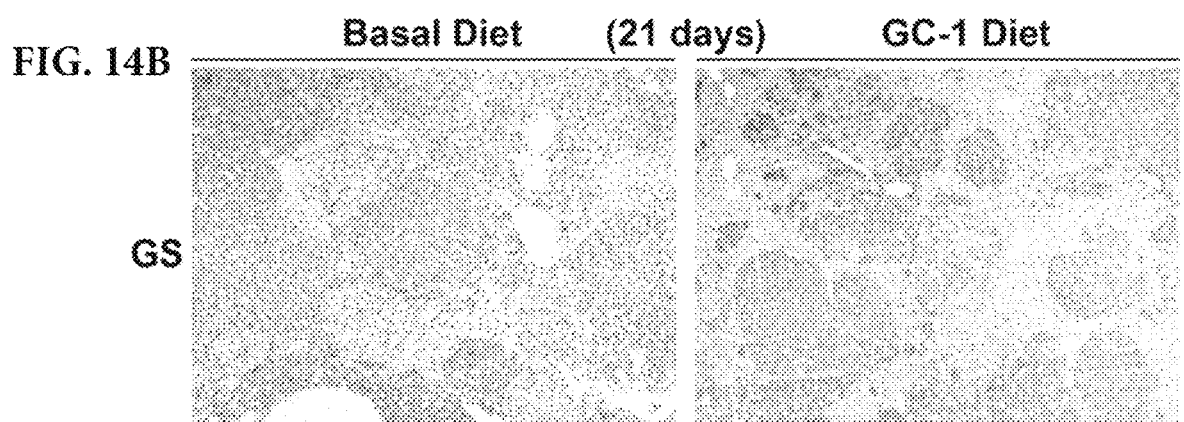
Figure 14C:
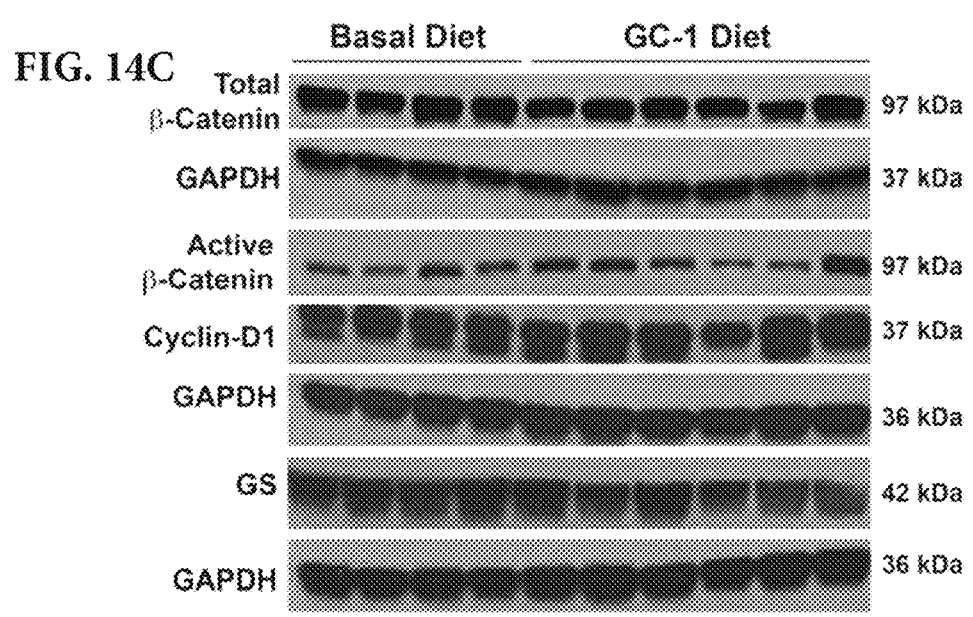

FIGS. 14A-14C. β-Catenin signaling in tumor-bearing livers remains unaffected after 21 days of GC-1 treatment. (A) A representative section from the liver of hMet-β-catenin mice fed 21 days with GC-1 or basal diet fed and stained for cyclin-D1 shows comparably positive staining although the tumor foci were smaller after GC-1 treatment (50×). (B) A representative IHC image for GS shows GS-positive tumor nodules in both GC-1 and basal diet groups although, the foci were notably smaller in GC-1 group (50×). (C) No change in levels of total β-catenin, active-n-catenin, cyclin-D1 and marginal decrease in total GS levels by representative WB, following 21-days of GC-1 treatment, suggests no change in Wnt/β-catenin signaling. GAPDH shows comparable loading.

Figure 15A:
Figure 15B:
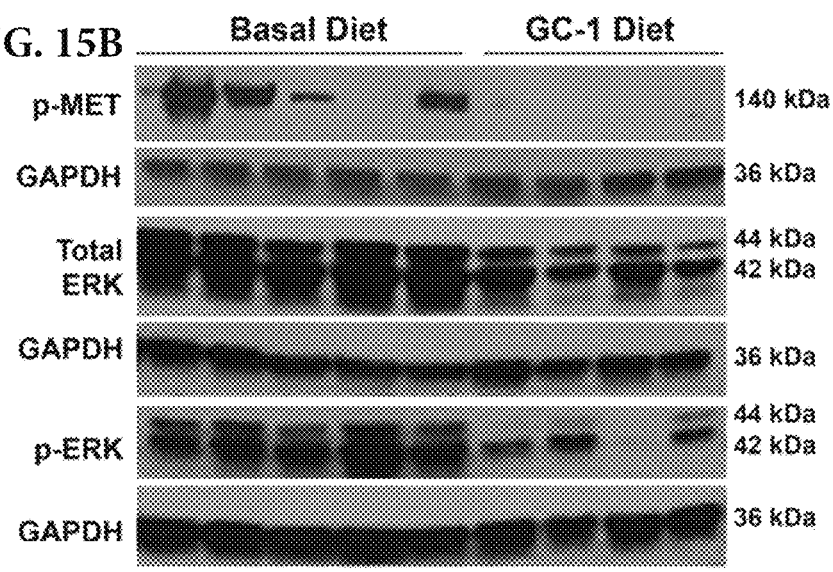
Figure 15C:
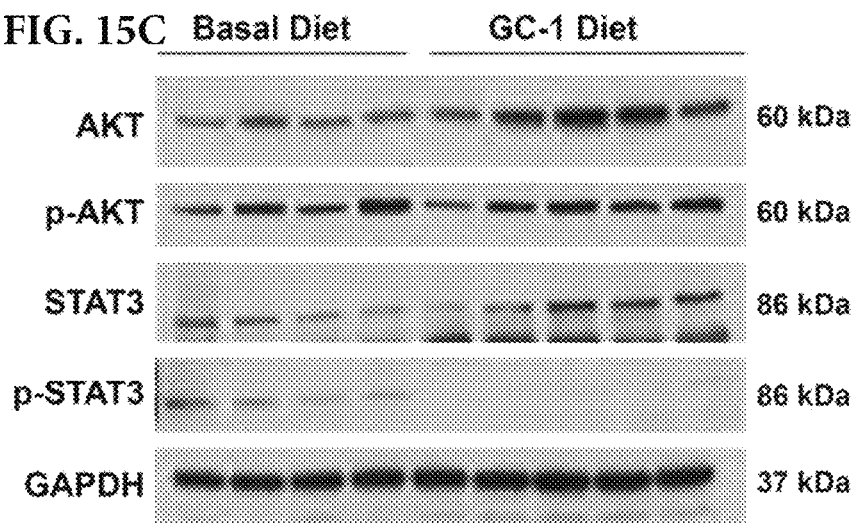

FIGS. 15A-15C. GC-1 treatment of hMet-mutant-β-catenin mice for 21-days leads to marked inhibition of Met signaling. (A) A profound decrease in p-Met (Y1234/Y1235) is observed by WB analysis using whole liver lysates from GC-1 treated mice versus basal diet controls. A marginal but variable decrease in total Met was also evident in this group. GAPDH shows comparable loading. (B) Another representative WB shows lack of p-Met (Y1234/1235) along with a dramatic decrease in downstream p-ERK1 (T202) and p-ERK2 (Y204) in GC-1 treated liver lysates. Total ERK1/2 levels were modestly decreased as well. GAPDH shows comparable loading. (C) A representative WB shows no change in p-AKT levels while total AKT levels were marginally increased after GC-1 treatment. However, while total STAT3 levels were relatively unaltered, a notable decrease in p-STAT3 (Y705) was clearly noticeable after 21 days of GC-1 treatment. GAPDH verified comparable protein loading.

FIGS. 16A-16D. hMet-mutant-β-catenin injected mice fed GC-1 diet for 10 days, show significantly less tumors than controls. (A) Schematic showing the timing of GC-1 or basal diet administration and animal sacrifice in reference to the HTVI of SBTT plasmids. (B) RT-PCR using RNA isolated from livers shows around 10-fold increase in gene expression of deiodinase after 10-days of GC-1-diet as compared to basal diet. (***p<0.001). (C) A significant difference in liver weight/body weight (LW/BW×100) is observed after 10-days of GC-1-diet (n=4) as compared to basal diet (n=4) suggesting a decrease in tumor burden.

Individual animals in each group are indicated by a closed circle or box. (**p<0.01). (D) Representative gross liver images from 10-days of GC-1 versus basal diet fed animals show unremarkable differences in the two groups.

FIGS. 17A-17C. Decreased tumor volume in hMet-mutant-β-catenin model following 10 days of GC-1 diet is not due to altered cell survival or inflammation. (A) Representative H&E stained sections (upper panels) show relatively fewer and smaller microscopic tumor foci evident as nodules composed of cells with basophilia, pyknotic nuclei and greater nuclear to cytoplasmic ratio, in 10-day GC-1-diet fed group versus basal diet group. IHC for Myc-Tag (lower panels) for 10-day GC-1 treated group versus controls, also shows smaller and fewer tumor foci (50×). (B) Comparable TUNEL-positive nuclei within the tumor foci were evident in the 10-day control diet-fed group versus GC-1-diet-fed mice (50×). (C) Comparable numbers of CD45-positive inflammatory cells were seen in both basal diet and GC-1 diet group (100×).

Figure 18A:
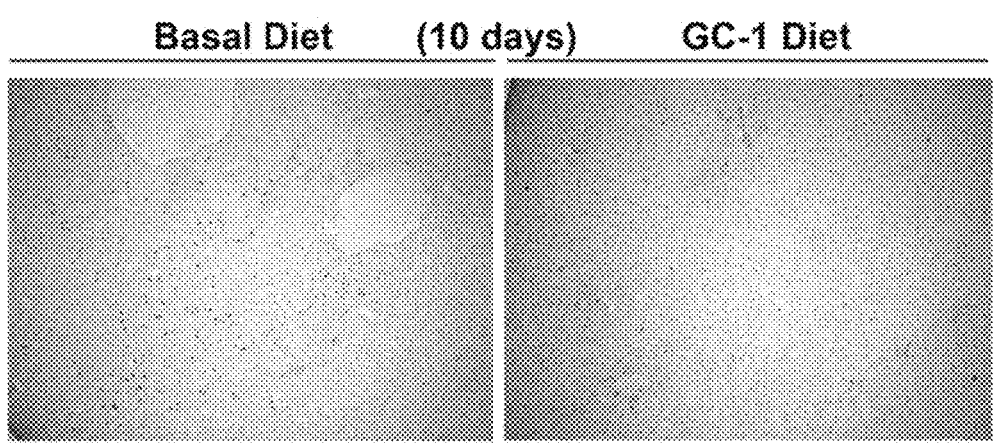
Figure 18B:
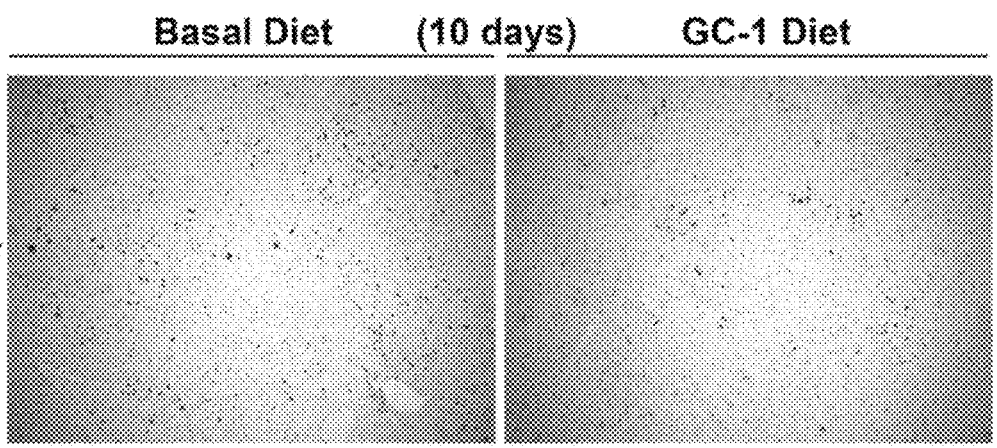
Figure 18C:
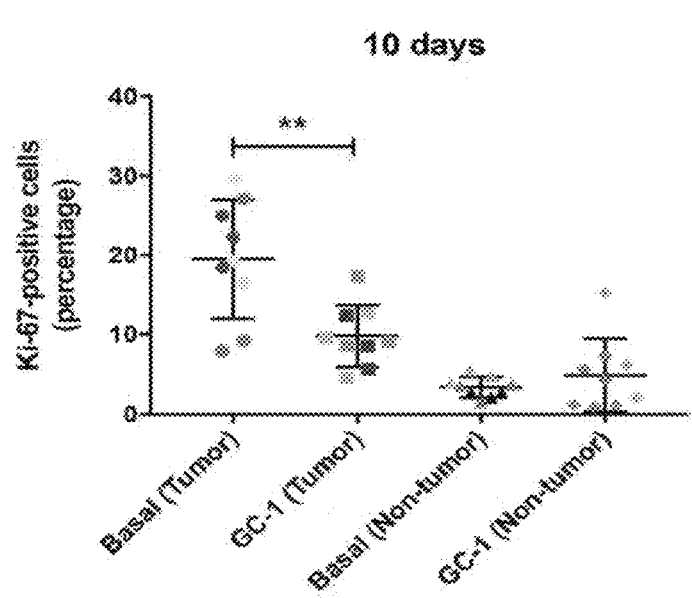

FIGS. 18A-18C. Decreased tumor volume in hMet-mutant-β-catenin model following 10 days of GC-1 diet is due to lower tumor cell proliferation. (A) IHC for BrdU shows a dramatic decrease in the numbers of BrdU-positive cells after 10-days of GC-1 feeding as compared to controls (50×). (B) A notable decrease in the numbers of Ki-67-positive cells within tumor nodules is evident in GC1-treated group versus controls (50×). (C) Quantification of Ki-67 staining shows a highly significant (**p<0.01) decrease in percentage of Ki-67-positive tumor cells in tumor foci in 10-day GC-1 diet fed mice as compared to basal diet group. Non-tumor tissues in both groups showed insignificant differences in Ki-67 positivity.

Figure 19A:
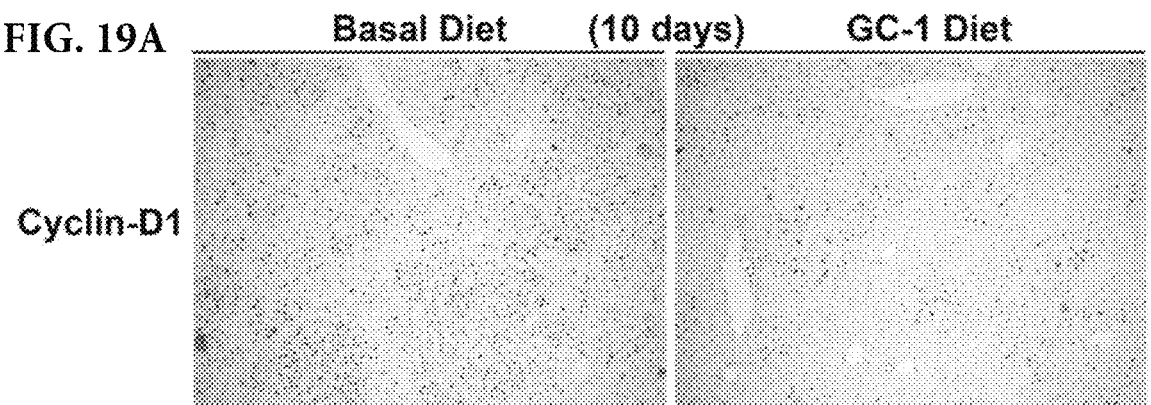
Figure 19B:
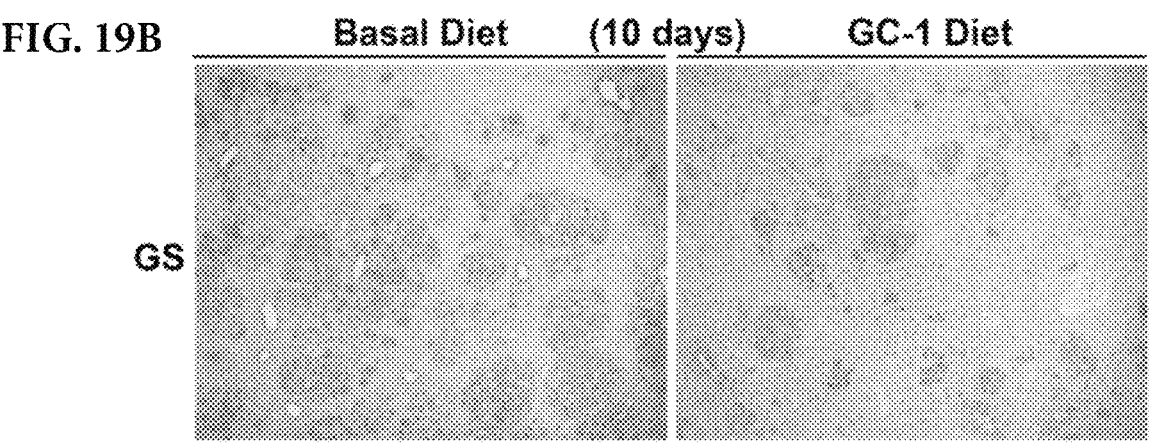
Figure 19C:
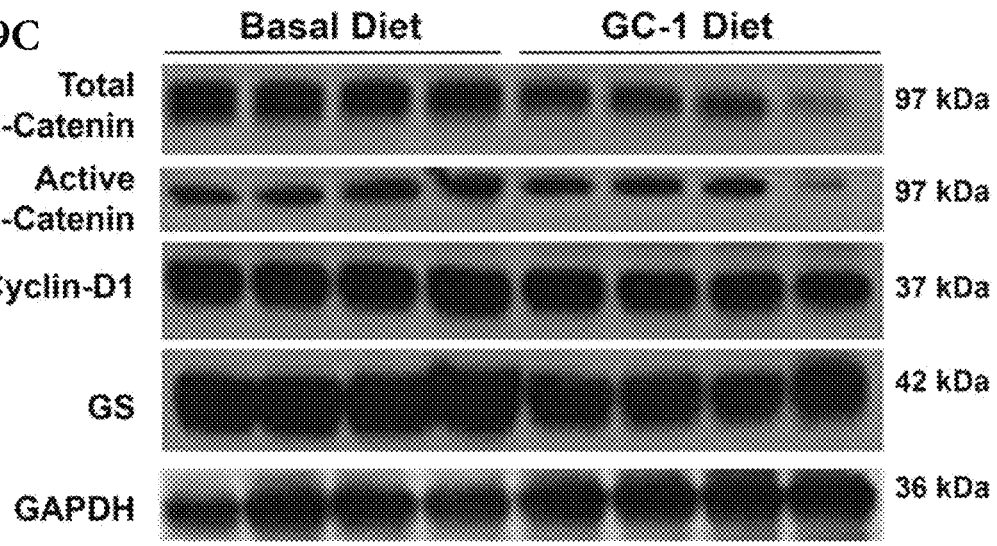

FIGS. 19A-19C: Ten days of GC-1 treatment does not impact Wnt signaling despite lowering tumor burden. (A) Representative sections from the livers of hMet-β-catenin mice fed 10 days with GC-1 or basal diet fed and stained for cyclin-D1 show comparably positive staining within tumor foci although the tumor foci were smaller in the GC-1 group (50×). (B) Representative IHC for GS also shows GS-positive tumor nodules in both GC-1 and basal diet groups although, the foci were notably smaller in GC-1 group (50×). (C) Representative WB analysis shows a marginal decrease in overall levels of total β-catenin, cyclin-D1 and GS but not active β-catenin, all supporting an overall lower tumor burden after 10 days of GC-1 treatment but not a direct impact on Wnt/β-catenin signaling. GAPDH shows comparable loading.

Figure 20A:
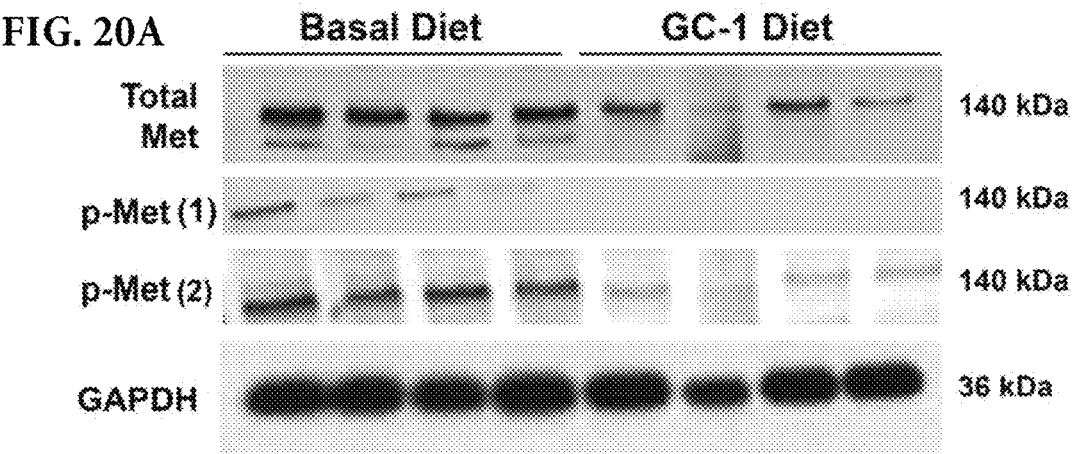
Figure 20B:
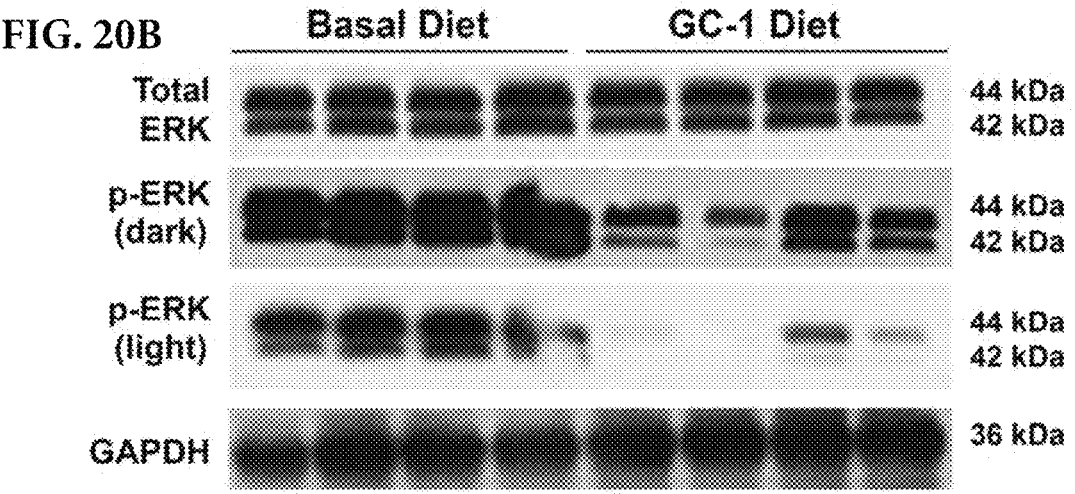
Figure 20C:
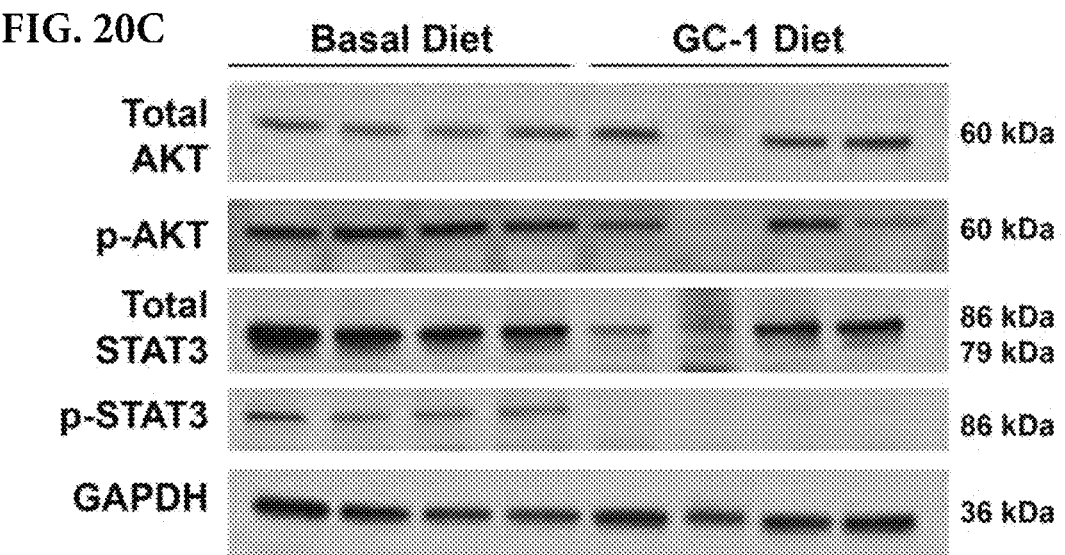

FIGS. 20A-20C. Remarkable decrease in Met-ERK and Met-STAT3 signaling following 10 days of GC-1 treatment in hMet-mutant-β-catenin mice. (A) A pronounced decrease in p-Met (Y1234/Y1235) is observed and validated by two independent antibodies by WB analysis using whole liver lysates from 10-day GC-1 treated versus basal-diet fed hMet-mutant-β-catenin mice. A marginal decrease in total Met levels was evident in this group as well. GAPDH shows comparable loading. (B) A representative WB using total liver lysates shows a dramatic decrease in p-ERK1 (T202) and p-ERK2 (Y204) but not total ERK after 10 days of GC-1. GAPDH shows comparable loading. (C) A representative WB shows no change in total AKT or p-AKT levels after 10 days of GC-1 treatment. Total STAT3 levels were overall reduced while p-STAT3 (Y705) levels were drastically lower after 10 days of GC-1 treatment. GAPDH verified comparable protein loading.

Figure 21:
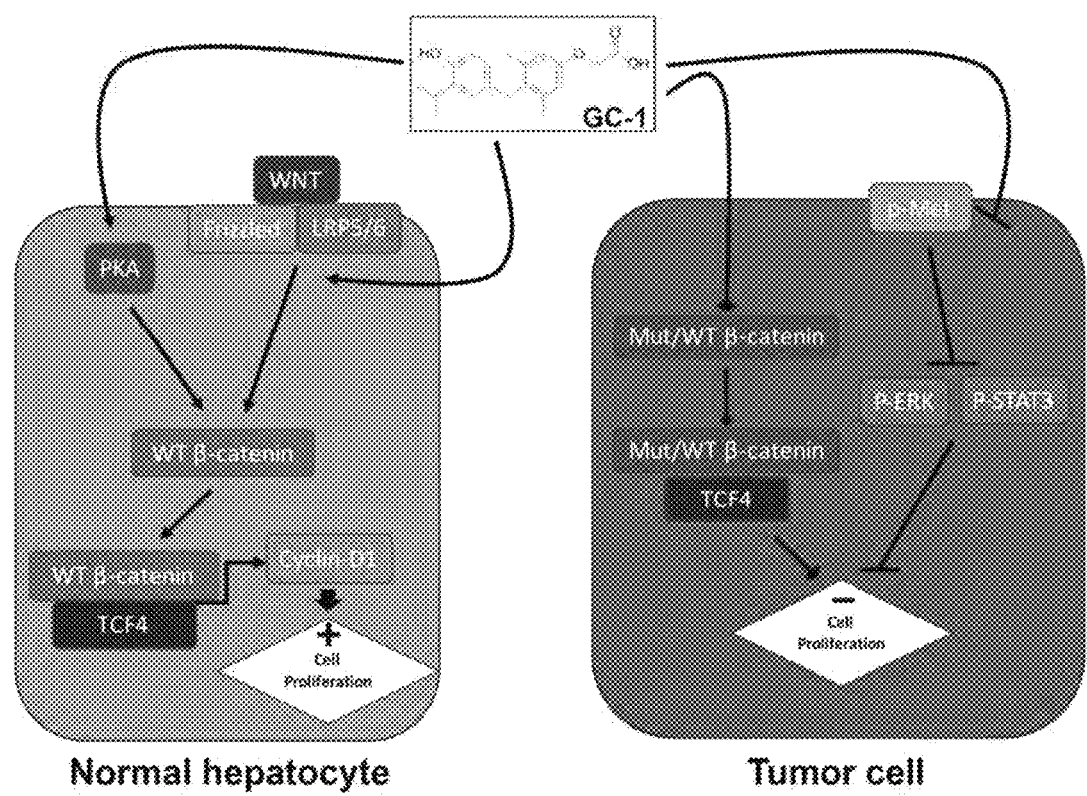

FIG. 21. Schematic of disparate effect of GC-1 on β-catenin signaling in normal hepatocyte versus a liver tumor cell. Thyroid hormone receptor 3 agonist GC-1 induces β-catenin signaling in normal hepatocyte by activating PKA-dependent ser675-phosphorylation (arrow) of β-catenin as well as by Wnt-dependent mechanisms (arrow). This leads to enhanced cyclin-D1 expression and hepatocyte proliferation and may be applicable for regenerative therapies. However, in a tumor cell, GC-1 is unable to increase β-catenin activation (diamond short) irrespective of the CTNNB1 mutational status. In addition, it dramatically inhibits Met-ERK and Met-Stat3 phosphorylation to have a profound effect on tumor burden in hMet-mutant-β-catenin mice, which represents around 10% of all human HCC.

DETAILED DESCRIPTION

It is disclosed herein that GC-1 can be utilized post-hepatectomy, such as in liver transplant populations, including living donors prior to donor surgery and in living donor recipients. GC-1 can also be used for the treatment of post liver transplant cadaveric recipients with SFSS (Small for size syndrome). Without being bound by theory, the method can extend the criteria for donor livers including donor after cardiac death (DCD donors), because more livers can be utilized, thus decreasing the scarcity of organs and reducing wait list mortality.

GC-1 can also be used in high risk donors. Marginal or extended criteria donors (ECD) are defined as those with a greater risk of initial poor function or graft failure and therefore an increased risk for recipient morbidity and mortality. For example, GC-1 can be used in elderly donors, donors with a high grade of steatosis, DCD/non-heart-beating donors, or split grafts. GC-1 can also be used in donors with a high Donor Risk Index (DRI), see for example, gastro_cchmc.org/calculators/donor-risk-index/, for example subjects that are over about 40, 41, 42, 43, 44, 45, 46, 47, 48, 48, 40 or 50 years old, for example, donor that are 40 to 55 years old, such as 45 to 55 years old.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. sobetirome or a pharmaceutically acceptable salt thereof), by any effective route. Exemplary routes of administration are described herein.

Hepatocyte: A cell of the main parenchymal tissue of the liver, that make up 70-85% of the mass of the liver. The typical hepatocyte is cubical with sides of 20-30 μm, and produces serum albumin, fibrinogen, and the prothrombin group of clotting factors (except for Factors 3 and 4). Hepatocytes also synthesize lipoproteins, ceruloplasmin, transferrin, complement, and glycoproteins. A hepatocyte is a normal (non-malignant) cell.

Liver Cancer (Hepatic Cancer): Cancer that initiates from the cells of the liver. The most frequent liver cancer, accounting for approximately 75% of all primary liver cancers, is hepatocellular carcinoma (HCC) which is formed by malignant transformation of hepatocytes. Liver cancer can also form from other structures within the liver such as the bile duct, such as cholangiocarcinoma and cholangiocellular cystadenocarcinoma. Cancers produced from muscle in the liver are leiomyosarcoma and rhabdomyosarcoma.

Liver Disease: Diseases and conditions of the liver including liver cirrhosis, alcoholic and non-alcoholic fibrosis as well as to liver disease or changes associated with obesity, diabetes and metabolic syndrome. Other examples of liver diseases include: hepatitis, fatty liver, toxic liver failure, hepatic cirrhosis, diabetes-associated liver disease, liver steatosis, liver fibrosis, liver cirrhosis, chronic hepatitis and the like. Liver disease does not include liver cancer.

Liver regeneration: Morphologic changes in which hepatocyte growth occurs in either a recipient or a donor of a liver transplant. The hepatic growth generally results in an increase in hepatic function.

Liver transplantation: Partial and whole liver transplantations in which the liver of a donor is partially or wholly resected and partially or wholly transplanted into a recipient. In partial liver transplantation, a partial liver from a donor, corresponding to about 30-50% of the normal liver volume of a recipient, is harvested and grafted into a recipient.

Macrovesicular Steatosis: Abnormal retention of lipids within a cell, reflecting an impairment of the normal processes of fatty acid and/or triglyceride synthesis and elimination. Excess lipid accumulates in vesicles that displace the cytoplasm. In macrovesicular steatosis, the vesicles become large enough to distort the cell's nucleus. The condition is not particularly detrimental to the cell in mild cases, large accumulations can disrupt cell constituents, and in severe cases cells may even burst. Many different mechanisms can disrupt normal lipid movement through the cell and cause steatosis. Those mechanisms can be classified based on whether they result in an oversupply of lipid or a failure of lipid breakdown. Oversupply of lipid may result from, among other conditions, obesity, insulin resistance, or alcoholism. Certain toxins, such as alcohols, carbon tetrachloride, aspirin, and diptheria toxin, among others, interfere with cellular machinery involved in lipid metabolism. In addition, certain metabolic diseases are characterized by defects in lipid metabolism. For example, in Gaucher's disease, the lysosomes fail to degrade glycolipids, resulting in steatosis.

Microvesicular Steatosis: A variant form of hepatic fat accumulation whose histologic features contrast with the much more common macrovesicular steatosis. The condition was originally described in association with conditions sharing a number of biochemical and clinical features: acute fatty liver of pregnancy. Reye's syndrome, Jamaican vomiting sickness, sodium valproate toxicity, high-dose tetracycline toxicity and certain congenital defects of urea cycle enzymes. Microvesicular steatosis has been observed in a wide variety of conditions, including alcoholism, toxicity of several medications, hepatitis delta virus infection (primarily in South America and Central Africa), sudden childhood death, congenital defects of fatty acid beta oxidation, cholesterol ester storage disease. Wolman disease and Alper's syndrome, see. e.g., M. L. Hautekeete et al., (1990) *Acta Clin. Belg.* 45(5):311-326.

Partial Heptatectomy or Resection: A surgical procedure in which a portion of the liver is removed. The surgeon may remove a part of the liver, such as an entire lobe, or an even larger portion of the liver. In a partial hepatectomy, the surgeon typically leaves sufficient healthy liver tissue to maintain the functions of the liver in a donor.

Pharmaceutical composition: A composition containing GC-1, or a pharmaceutically acceptable salt thereof, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

Pharmaceutically acceptable salt: A salt of GC-1 which is, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free carboxylic acid group with a suitable base. Representative alkali or alkaline earth metal salts include sodium, lithium, potassium, calcium, magnesium, and the like, as well as nontoxic ammonium, primary ammonium, secondary ammonium, tertiary ammonium, or quaternary ammonium cations, including, but not limited to ammonium, tetramethylammonium, tetraethylammonium, methylammonium, dimethylammonium, trimethylammonium, triethylammonium, ethylammonium, and the like.

Pharmaceutically acceptable excipient (pharmaceutically acceptable carrier): Any ingredient other than GC-1, or a pharmaceutically acceptable salt thereof (e.g., a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The pharmaceutically acceptable excipients or carriers useful for each specific mode of administration are described herein.

Resection: The excision of a portion or all of an organ or other structure. For example, liver resection refers to surgical removal of a portion of the liver and is usually performed to remove the diseased portion of the liver, or to provide a portion of a liver for transplant into another subject.

Small-For-Size (SFS) Liver Transplant: A surgical technique in which a donor liver is split into two or more fragments, each of which is subsequently transplanted into a different recipient. Adequate hepatic regeneration is essential for recovery of patients receiving SFS transplants, most of whom are chronically ill with severely compromised liver function. Inadequate regeneration can result in "small-for-size graft syndrome," characterized by poor bile production, intractable ascites, and prolonged cholestasis, and is often associated with surgical and septic complications.

Sobetirome (GC-1): A synthetic diarylmethane derivative that was investigated clinically as a potential therapeutic for hypercholesterolemia (see U.S. Pat. No. 5,883,294, which is herein incorporated by reference). Other names for GC-1 found in the literature and regulatory filings include QRX-431 and GC-1.

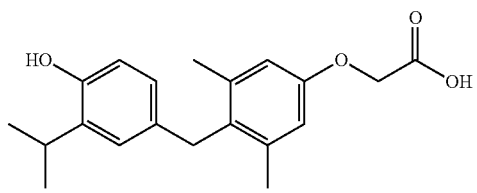 [SMILES: Cc1cc(OCC(=O)O)cc(C)c1Cc1ccc(O)c(C(C)C)c1]

Subject: An animal (e.g., a mammal, such as a human). A subject to be treated according to the methods described herein may be one who has been diagnosed with a neurodegenerative disease involving demyelination, insufficient myelination, or under-development of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

Therapeutically effective amount: A quantity of GC-1, or a pharmaceutically acceptable salt thereof, sufficient to achieve a desired effect in a subject, or in a cell, being treated with GC-1. The effective amount of GC-1 depends on several factors, including, but not limited to the subject or cells being treated, and the manner of administration of the therapeutic composition. In some embodiments, a "therapeutically effective amount" of GC-1, or a pharmaceutically acceptable salt thereof, is the amount sufficient to increase liver function in a subject. In other embodiments, a "therapeutically effective amount" of GC-1, or a pharmaceutically acceptable salt thereof, is the amount sufficient to increase the number of liver cells in a liver transplant donor or a liver transplant recipient. Treating also refers to blocking, suppressing, inhibiting, reducing, attenuating, ameliorating or reversing any or all conditions, effects or cause(s) of the liver injury, as well as symptoms or diseases related to the liver injury: increasing the time between the disappearance of a condition, symptoms or effect and its reoccurrence; stabilizing an adverse symptom associated with liver injury; or reducing, slowing, or stabilizing the progression of a condition associated liver injury.

Transplantation of Liver: Grafting of one or more partial hepatic tissue(s) or cell(s) taken or derived from another or the subject's own liver. A transplant can be autologous (from the same subject) or allogeneic (from a different subject). Generally, a liver transplant is allogeneic. The tissue can be matched for the Major Histocompatibility Complex (MHC) class II.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

Administration of GC-1 (Sobetirome) or Pharmaceutical Compositions Thereof

GC-1, a prodrug thereof (see Placzek et al., Bioorg Med Chem. 2016 Nov. 15; 24(22):5842-5854, incorporated herein by reference, which discloses prodrugs of GC-1 such as ester prodrugs) and pharmaceutically acceptable salts thereof can be administered according to any suitable route of administration for treatment. For example, standard routes of administration include intravenous, oral, parenteral, or topical routes of administration. In particular, the route of administration of GC-1, a prodrug thereof, or a pharmaceutically acceptable salt thereof can be oral (e.g., enteral, buccal, sublingual, sublabial, or by inhalation). Parenteral route of administration of GC-1, a prodrug thereof, or a pharmaceutically acceptable salt thereof, can be, e.g., intra-arterial, intravenous, intraventricular, intramuscular, subcutaneous, intraspinal, intraorbital, or intracranial; these routes can also be utilized in the disclosed methods. In some embodiments, a topical route of administration is utilized, such as cutaneous, intranasal, or ophthalmic.

Pharmaceutical compositions comprising GC-1 have been described in the art (see, e.g., U.S. Pat. No. 5,883,294, which is herein incorporated by reference). GC-1, prodrugs thereof, and pharmaceutically acceptable salts thereof that are to be administered intravenously or orally can be formulated as liquids, for example suspensions or emulsions, or as tablets, capsules or lozenges. A liquid composition will generally include a suspension or solution of GC-1, a prodrug thereof, or pharmaceutically acceptable salt in a suitable liquid carrier, for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. A liquid formulation can be prepared in dimethyl sulfoxide (DMSO).

In some instances, a composition for intramuscular administration contains a suspension or solution of active ingredient in an oil, for example *arachis* oil or sesame oil. A composition for intravenous administration can include a sterile isotonic aqueous solution containing, for example active ingredient, dextrose, sodium chloride, a co-solvent, for example polyethylene glycol and, optionally, a chelating agent, for example ethylenediamine tetracetic acid and an anti-oxidant, for example, sodium metabisulphite. Alternatively, the solution can be freeze dried and then reconstituted with a suitable solvent just prior to administration.

In some cases, for oral administration, a powder containing active compound, suspending agent, sucrose and a sweetener can be reconstituted with water to form a suspension; and a syrup can be prepared from a powder containing active ingredient, sucrose and a sweetener. A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix. A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule. GC-1, prodrugs thereof, and pharmaceutically acceptable salts thereof to be administered parenterally can be formulated, for example, for intramuscular or intravenous administration.

GC-1, prodrugs thereof, and pharmaceutically acceptable salts thereof for rectal administration can be formulated as suppositories. A typical suppository formulation will generally include active ingredient with a binding and/or lubricating agent such as a gelatin or cocoa butter or other low melting vegetable or synthetic wax or fat.

GC-1, prodrugs thereof, and pharmaceutically acceptable salts thereof to be administered topically can be formulated as transdermal compositions. Such compositions include, for example, a backing, active compound reservoir, a control membrane, liner and contact adhesive.

Non-limiting examples of formulations for buccal, sublingual, and/or sublabial administration may be found in U.S. Published Patent Application No. 2012/0058962, U.S. Published Patent Application No. 2013/0225626, U.S. Published Patent Application No. 2009/0117054, and U.S. Pat. No. 8,252,329; the disclosure of each of which is incorporated herein by reference. For buccal, sublingual, or sublabial administration, the compositions may take the form of tablets, lozenges, etc. formulated in a conventional manner, as described for oral dosage forms. In some embodiments, the formulation for buccal, sublingual, or sublabial administration includes one or more of taste masking agents, enhancers, complexing agents, and other described above pharmaceutically acceptable excipients and carriers.

Taste masking agents include, for example, taste receptor blockers, compounds which mask the chalkiness, grittiness, dryness, and/or astringent taste properties of an active compound, compounds which reduce throat catch as well as compounds which add a flavor. A taste receptor blocker used in the formulation of the present disclosure may include Kyron T-134, a glycoprotein extract called miraculin from the fruit of the plant *synsepalum dulcifcum*, ethyl cellulose, hydroxypropyl methylcellulose, arginine, sodium carbonate, sodium bicarbonate, gustducin blockers and mixtures thereof. Compounds which mask the chalkiness, grittiness, dryness and/or astringent taste properties of an active compound include those of a natural or synthetic fatty type or other flavorant such as cocoa, chocolate (e.g., mint chocolate), cocoa butter, milk fractions, vanillin butter fat, egg or egg white, peppermint oil, wintergreen oil, spearmint oil, and similar oils. Compounds which reduce throat catch include combinations of high and low solubility acids. For example, high solubility acids suitable for use here include amino acids (e.g., alanine, arginine etc.), glutaric, ascorbic, malic, oxalic, tartaric, malonic, acetic, citric acids and mixtures thereof. Low solubility acids suitable for use include oleic, stearic and aspartic acids plus certain amino acids such as glutamic acid, glutamine, histidine, isoleucine, leucine, methionine, phenylalanine, serine, tryptophan, tyrosine, valine and fumaric acid. Actual amounts used will vary depending on the amount of throat catch or burn exhibited by the active used but will generally be in the range of 1 to 40%. Flavoring agents include sweeteners and flavors. Examples of suitable sweeteners and flavors include mannitol, sorbitol, maltitol, lactitol, isomaltitol, erythritol, xylitol, sucrose, ammonium glycyrrhizinate, mango aroma, black cherry aroma, sodium citrate, colloidal silicon dioxide, sucralose; zinc gluconate; ethyl maltitol; glycine; acesulfame-K; aspartame; saccharin; acesulfam K, neohesperidin DC, thaumatin, stevioside, fructose; xylitol; honey; honey extracts; corn syrup, golden syrup, misri, spray dried licorice root; glycerrhizine; dextrose; sodium gluconate; *stevia* powder; glucono delta-lactone; ethyl vanillin; vanillin; normal and high-potency sweeteners or syrups or salts thereof and mixtures thereof. Other examples of appropriate flavoring agents include coffee extract, mint; lamiacea extracts; citrus extracts; almond oil; babassu oil; borage oil; blackcurrant seed oil; canola oil; castor oil; coconut oil; corn oil; cottonseed oil; evening primrose oil; grape seed oil; groundnut oil; mustard seed oil; olive oil; palm oil; palm kernel oil; peanut oil; grapeseed oil; sunflower oil; sesame oil; shark liver oil; soybean oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; safrole, citric acid, d-limonene, malic acid, and phosphoric acid or salts and/or mixtures thereof.

Enhancers are the agents that increase membrane permeability and/or increase the solubility of a particular active compound. Both issues can be pivotal to the properties of the formulation. An enhancer may be a chelator, a surfactant, a membrane-disrupting compound, a fatty or other acid; a non-surfactant, such as an unsaturated cyclic urea. A chelator may be, e.g., EDTA, citric acid, sodium salicylate, or a methoxysalicylate. A surfactant may be, e.g., sodium lauryl sulphate, polyoxyethylene, POE-9-laurylether, POE-20-cetylether, benzalkonium chloride, 23-lauryl ether, cetylpyridinium chloride, cetyltrimethyl ammonium bromide, or an amphoteric or a cationic surfactant. A membrane-disrupting compound may be, e.g., a powdered alcohol (such as, menthol) or a compound used as lipophilic enhancer. Fatty and other acids include, e.g., oleic acid, capric acid, lauric acid, lauric acid/propylene glycol, methyloleate, yso-phosphatidylcholine, and phosphatidylcholine. Other enhancers that may be used in buccal, sublingual, and sublabial formulations of the present disclosure include, e.g., lysalbinic acid, glycosaminoglycans, aprotinin, azone, cyclodextrin, dextran sulfate, curcumin, menthol, polysorbate 80, sulfoxides, various alkyl glycosides, chitosan-4-thiobutylamide, chitosan-4-thiobutylamide/GSH, chitosan-cysteine, chitosan-(85% degree N-deacetylation), poly(acrylic acid)-homocysteine, polycarbophil-cysteine, polycarbophil-cysteine/GSH, chitosan-4-thioethylamide/GSH, chitosan-4-thioglycholic acid, hyaluronic acid, propanolol hydrochloride, bile salts, sodium glycocholate, sodium deoxycholate, sodium taurocholate, sodium glycodeoxycholate, and sodium taurodeoxycholate.

Buffering materials can be both used to increase solubility and enhance adsorption of active compounds. Examples of suitable buffering materials or antacids suitable for use herein comprise any relatively water soluble antacid acceptable to the Food & Drug Administration, such as aluminum carbonate, aluminum hydroxide (or as aluminum hydroxide-hexitol stabilized polymer, aluminum hydroxide-magnesium hydroxide co-dried gel, aluminum hydroxide-magnesium trisilicate codried gel, aluminum hydroxide-sucrose powder hydrated), aluminum phosphate, aluminum hydroxyl carbonate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide, and magnesium trisilicate, and/or mixtures thereof. Preferred buffering materials or antacids include aluminum hydroxide, calcium carbonate, magnesium carbonate and mixtures thereof, as well as magnesium hydroxide. Many of these compounds have the advantage of also being taste masking agents particularly useful for addressing throat catch. The selection of the other excipients, such as permeation enhancers, disintegrants, masking agents, binders, flavors, sweeteners and taste-masking agents, is specifically matched to the active depending on the predetermined pharmacokinetic profile and/or organoleptic outcome.

Liquid drug formulations suitable for use with nebulizers and liquid spray devices and electrohydrodynamic (EHD) aerosol devices will typically include GC-1, a prodrug thereof, or a pharmaceutically acceptable salt thereof with a pharmaceutically acceptable carrier.

In some embodiments, the pharmaceutically acceptable carrier is a liquid, e.g., alcohol, water, polyethylene glycol, or a perfluorocarbon. Optionally, another material may be added to alter the aerosol properties of the solution or suspension. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., U.S. Pat. Nos. 5,112,598 and 5,556,611, each of which is herein incorporated by reference).

Methods of Stimulating Liver Regeneration

Provided herein are methods of stimulating liver regeneration in a subject, such as, but not limited to, a liver transplant donor or a liver transplant recipient. In some embodiments, the methods stimulate liver regeneration and decrease ischemia/reperfusion injury. In some embodiments, the subject can have a partial liver resection, and optionally can be a transplant donor. In other embodiments, the subject can be a recipient of a liver transplant, such as a cadaveric transplant or a transplant from a living donor. The subject can be a mammal, such as a domestic animal or a primate. In some examples, the subject is a human. In some embodiments, the subject does not have liver cancer, such as hepatocellular carcinoma.

In some embodiments, the individual has undergone a partial hepatectomy or liver resection. In some non-limiting examples, the partial hepatectomy or liver resection removed 5%, 10%, 15%, 20%, 25%, 30%, 35%, 40%, 45%, 50%, 55%, 60%, 65%, 70%, 75%, 80%, 85%, 90%, or 95% by mass of the subject's liver. In some embodiments, the subject is a liver donor. In some embodiments, the hepatectomy is anatomic, so that the lines of resection match the limits of one or more functional segments of the liver as defined by the Couinaud classification. The subject can be a living donor for a liver transplant. The subject can be an adult (over 18 years old), or a child (under 13 years old) or a teenager (13 to 19 years old). The subject can be over 20, 30, 40, 50, or 60 years old.

In further embodiments, the subject has undergone a liver transplant, and is a transplant recipient. In further embodiments the subject has undergone a small-for-size liver transplant. In some embodiments, the individual has undergone a liver transplant due to liver damage caused by toxic injury, traumatic injury, microvesicular steatosis, or macrovesicular steatosis. In some non-limiting examples, the toxic injury results from acetominophen overdose, exposure to carbon tetrachloride ($CCl_4$), bacterial endotoxin, use or abuse of intravenous or prescription drugs, chemotherapy, excessive consumption of alcohol, or infection with hepatitis virus A, B. or C. Traumatic injury can result from surgical resection or blunt force trauma, such as that occurring in an automobile accident. In certain embodiments, the method of stimulating liver regeneration in an individual in need thereof comprises administering to the individual a pharmaceutical composition including GC-1, a prodrug thereof, or a pharmaceutically acceptable salt thereof. In some embodiments, the subject has received an extended criteria liver, such as, but not limited to, a liver harvested from a subject that is greater than about 45 years old, such as about 45 to about 55 years old, such as about 45 to old 50 years old. In further embodiments, the subject has received a cadaveric liver. In yet other embodiments, the subject has received a liver transplant from a living donor.

The dose and dosing schedule for administration of GC-1 (or a prodrug thereof of a pharmaceutically acceptable salt thereof) can vary and is determined in part by the clinical status of the subject, and the age, such as the weight and general health of the patient, and the route of administration. In some embodiments, the composition is administered daily. In other embodiments the composition is administered more than once a day, such as twice a day, three time a day or four times a day. In yet other embodiments, the composition is administered once a day, every other day, every three days or once a week. In some embodiments, the drug is administered by an intravenous infusion, such as within one day after transplantation or resection, and continued for at least 7 days, such as 8, 9, 10, 11, 12, 13 or 14 days, such as for about 7 to about 14 days. However, the IV infusion can be continued for longer periods, such as for up to three weeks. In a liver transplant donor, and IV infusion can be administered before and/or after a resection procedure.

In some embodiments, GC-1, a prodrug thereof, or a pharmacologically acceptable salt thereof is administered intravenously, such as using an infusion. In further embodiments, the dose of GC-1 is about 0.01 mg/kg to about 0.5 mg/kg, such as about 0.05 mg/kg to about 0.35 mg/kg, about 0.01 mg/kg to about 0.30 mg/kg, or about 0.1 mg/kg to about 0.3 mg/kg. In particular examples, the dose of GC-1 (or a pharmaceutically acceptable salt thereof) is about 0.2, 0.25, 0.3, 0.35, 0.4, 0.45 or 0.5 mg/kg. In further embodiments, the GC-1 can be administered within one day of a surgical procedure, such as a liver resection or a liver transplantation, for example in a liver donor or in a liver recipient. The GC-1 can be administered within 1, 2, 3, 4, 5, 6, 7, 8, 9, 10, 11, 12, 24, 36, 48, 72 or 96 hours of the surgical procedure, and continued, as disclosed above. The GC-1, prodrug thereof, or pharmaceutically acceptable salt thereof, can be administered after a procedure, such as, but not limited to, in a liver transplant recipient or liver transplant donor. The GC-1, prodrug thereof, or pharmaceutically acceptable salt thereof can be administered before a procedure, such as, but not limited to, to a liver transplant donor or recipient.

In particular embodiments, the GC-1, a prodrug thereof, or pharmaceutically acceptable salt is administered orally, such as once daily, twice daily, three times daily, once every two days, once weekly, twice weekly, three times weekly, once biweekly, once monthly, or once bimonthly. In certain embodiments, the compound is administered to the subject once daily or twice daily. In other embodiments, the effective amount is more than 30 µg (e.g., more than 50 µg, such as more than 100 µg). In some embodiments, the effective amount is more than 30 µg (e.g., more than 50 µg, such as more than 100 Cgg) daily. In certain embodiments, the effective amount is more than 30 µg (e.g., more than 50 µg, such as more than 100 Cgg) twice daily. In particular embodiments, the effective amount is more than 30 µg (e.g., more than 50 µg, such as more than 100 Cgg) once weekly. In other embodiments, the effective amount is more than 30 µg (e.g., more than 50 µg, such as more than 100 Cgg) twice weekly. In certain embodiments, the effective amount is at least 30 µg (e.g., more than 50 µg, such as more than 100 µg) three times weekly. In some embodiments, the effective amount is less than 1 mg (e.g., less than 500 µg, such as less than 200 µg). In further embodiments, the GC-1 can be administered within one day of a surgical procedure, such as a liver resection or a liver transplantation, for example in a liver donor or in a liver recipient. The GC-1, prodrug or salt can be administered within 1, 2, 3, 4, 5, 6, 7, 8, 9, 10, 11, 12, 24, 36, 48, 72 or 96 hours of the surgical procedure (before and/or after the procedure). In some embodiments, the GC-1, prodrug thereof, or pharmaceutically acceptable salt thereof is given about 12 hours before the surgery is performed. In some embodiments, GC-1, a prodrug thereof, or a pharmaceutically acceptable salt thereof is given orally within one day of a surgical procedure, such as a liver donation. In further embodiments, the GC-1 prodrug thereof, or pharmaceutically acceptable salt thereof is administered after the surgical procedure. This administration can be continued for at least 7 days, such as 8, 9, 10, 11, 12, 13 or 14 days, such as for about 7 to about 14 days. However, the oral administration can be continued for longer periods, such as for up to 3, 4, 5, 6, 7 or 8 weeks. In a liver donor, administration can be prior to, and subsequent to, surgical resection of the liver. The GC-1, prodrug thereof, or pharmaceutically acceptable salt thereof, can be administered after a procedure, such as, but not limited to, in a liver transplant recipient or liver transplant donor. The GC-1, prodrug thereof, or pharmaceutically acceptable salt thereof can be administered before a procedure, such as, but not limited to, to a liver transplant donor or recipient.

In some embodiments, the methods of the present disclosure involve administering a unit dosage form containing from 10 µg to 100 µg of GC-1, a prodrug thereof, or a pharmaceutically acceptable salt thereof, once, twice or three times per day orally. In some embodiments, the methods of the present disclosure involve administering a unit dosage form containing from 10 µg to 75 µg of GC-1, a prodrug thereof, or a pharmaceutically acceptable salt thereof, once, twice or three times per day. In other embodiments, the methods of the present disclosure involve administering a unit dosage form containing from 30 µg to 75 µg of GC-1, prodrug thereof, or a pharmaceutically acceptable salt thereof, once, twice or three times per day. In particular embodiments, the methods of the present disclosure involve administering a unit dosage form containing from 10 µg to 50 µg of GC-1, prodrug thereof, or a pharmaceutically acceptable salt thereof, once, twice or three times per day. In yet other embodiments, the methods of the present disclosure involve administering a unit dosage form containing from 30 µg to 50 µg of GC-1, prodrug thereof, or a pharmaceutically acceptable salt thereof, once, twice or three times per day. In still other embodiments, the methods of the present disclosure involve administering a unit dosage form containing from 50 µg to 75 µg of GC-1, prodrug thereof, or a pharmaceutically acceptable salt thereof, once, twice or three times per day. In further embodiments, the GC-1, prodrug or pharmaceutically acceptable salt can be administered within one day of a surgical procedure, such as a liver resection or a liver transplantation, for example in a liver donor or in a liver recipient. The GC-1, prodrug thereof, or pharmaceutically acceptable salt thereof, can be administered within 1, 2, 3, 4, 5, 6, 7, 8, 9, 10, 11, 12, 24, 36, 48, 72 or 96 hours of the surgical procedure, such as within 24 hours of a surgical procedure. The GC-1, prodrug thereof, or pharmaceutically acceptable salt thereof can be administered before and/or after a procedure.

The method can include measuring liver function using a quantitative and/or qualitative test. In some embodiments, the degree of liver impairment is assessed using tests which evaluate structure (e.g., biopsy), cellular permeability (e.g., transaminases) and synthetic ability (e.g., albumin. bilirubin and prothrombin time) (see Jalan and Hayes (1995) Aliment. Pharmacol. Ther. 9:263-270). A combination of various markers for liver injury can be masured to provide an analysis function. Commonly used tests for liver clearance capability are: indocyanine green (ICG), galactose elimination capacity (GEC), mono-ethyl-glycine-xylidide (MEG-X), antipryine clearance, aminopyrine breath test (ABT) and caffeine clearance. For assessment of graft function following transplantation, low ICG clearance and low MEG-X formation are predictive of a poor outcome. The method can also include measuring the lipid profile of a subject.

Acetaminophen Overdose Treatment

In some embodiments. GC-1 or a pharmaceutical salt thereof is administered to a subject who has taken an overdose or hepatotoxic dose acetaminophen. In some embodiments, a GC-1 or pharmaceutically acceptable salt thereof can that reduce the risk for liver transplantation following acetaminophen overdose. If the subject has a liver transplant subsequent to the acetaminophen overdose, then the GC-1 or pharmaceutically acceptable salt thereof can be administered following the liver transplant. In further embodiments, a subject can be selected that has taken an overdose or hepatotoxic dose acetaminophen. This subject can further undergo a transplantation, but need not undergo a transplantation.

Acetaminophen is a widely used analgesic and antipyretic medication that is generally perceived to be nontoxic. However, large or repeated doses of acetaminophen cause profound liver injury, potentially leading to liver failure. When consumed at doses outside the therapeutic range, or in the context of altered hepatic metabolism due to alcohol, drugs such as isoniazid, viral infections, or other concurrent medical conditions, this drug can cause significant liver damage. Acetaminophen-induced morbidity and mortality poses a serious clinical problem. Severe acute liver injury due to acetaminophen overdose is a major clinical issue, and often requires liver transplantation for the survival of the patient.

Acetaminophen overdoses are typically treated with N-acetyl-cysteine (NAC), which can prevent hepatic failure, but only if timely administered. When exposed to acetaminophen, the hepatocyte uses glutathione to neutralize the toxic effects of the N-acetyl-p-benzoquinoneimine metabolite of acetaminophen. The toxic effects of this metabolite can be reversed with the addition of NAC, but the efficacy of NAC declines precipitously as hepatocytes succumb to the toxic effects of N-acetyl-p-benzoquinoneimine. Delayed NAC treatment for acetaminophen-induced hepatotoxicity fails, in part, because this drug fails to trigger the restoration of the critical mass of hepatocytes needed for liver function. NAC treatment that is delayed more than eight hours after acetaminophen overdose can fail to prevent acute liver failure. After the therapeutic window of NAC is passed, liver transplantation is often the only clinical intervention that will ensure the survival of these patients. The GC-1 or pharmaceutically acceptable salt thereof can be administered in combination with NAC.

Despite the evidence that the liver possesses a tremendous capacity to regenerate following hepatic injury, few biological substances can increase hepatic cell number. GC-1 or a pharmaceutically acceptable salt thereof can be used to counteract the hepatic necrosis that follows acetaminophen-induced toxicity. In some embodiments, the GC-1 or pharmaceutically acceptable salt thereof can be administered within 1, 2, 3, 4, 5, 6, 7, or 8 hours of an acetaminophen overdose. In other embodiments, the GC-1 or pharmaceutically acceptable salt thereof is administered more than 8, 9, 01, 11, 12, 13, 14, 15, 16, 17, 18, 19, 20, 21, 22, 23, 24, 48 or 72 hours after an acetaminophen overdose. The GC-1 or pharmaceutically acceptable salt thereof is administered 8, 9, 01, 11, 12, 13, 14, 15, 16, 17, 18, 19, 20, 21, 22, 23, 24, 48 or 72 hours after an acetaminophen overdose. Optionally, an effective amount of NAC is also administered to the subject. Suitable doses are disclosed in the section above. Any of the oral or intravenous infusion protocols disclosed for use in transplant recipients or transplant donors are of use in acetaminophen-induced toxicity.

If a subject that has an acetaminophen overdose requires a liver transplant, then an effective amount of GC-1, or a pharmaceutically acceptable salt thereof, can also be administered, as discussed above.

Liver Disease Treatment

In some embodiments, GC-1 or a pharmaceutical salt thereof is administered to a subject who has a liver disease. In some embodiments, a GC-1 or pharmaceutically acceptable salt thereof can that reduce the risk for liver transplantation in a subject with liver disease. If the subject has a liver transplant subsequent to the liver disease, then the GC-1 or pharmaceutically acceptable salt thereof can be administered following the liver transplant. In further embodiments, a subject can be selected that has a liver disease. This subject can further undergo a transplantation, but need not undergo a transplantation. A subject can be selected that does not have liver cancer, such as hepatocellular carcinoma.

Thus, a subject can be treated that has alcoholic liver cirrhosis, liver cirrhosis caused by chronic infection after acute inflammation of the liver or immunological liver diseases characterized by chronic inflammation.

In some embodiments, the subject is an alcoholic or a recovering alcoholic. The development of cirrhosis hepatitis is preceded by a state of increasing accumulation of fat in the liver (steatosis hepatitis). This state is reversible and the liver can be normalized if consumption of alcohol is terminated. However, if the abuse goes on then the liver tissue will gradually be transformed to connective tissue which leads to badly working liver tissue and consequently reduced function of the liver. These subjects can be treated using the methods disclosed herein.

In some embodiments, subject are treated that have chronic liver disease, such as liver disease wherein there are very low concentrations of the proteins and hormones which are produced in the liver. A reduced concentration of the protein albumin in the blocxlod is of importance for the development of edema in the abdominal cavity such as ascites and in the legs caused by chronic liver disease. Subjects with liver disease can be treated that have a reduced capability of production of coagulation factors, which are important for the normal coagulation of blood, and an increased tendency of bleeding. Thus, in some embodiments, the disclosed methods include selecting subject with one or more of these features.

The disclosure is illustrated by the following non-limiting Examples.

EXAMPLES

The capacity of the liver to regenerate has long been of interest to the scientific community. It is a focus of much research both for academic purposes and clinical applications that could be lifesaving in cases of end stage liver disease (Karp (2009) *Am J Transplant* 9, 1973-1980). Out of the midst of redundant pathways that give the liver this unique ability, β-catenin has emerged as an important player (Monga (2014) *Gene Expr* 16, 51-62; Goessling et al. (2008) *Dev Biol* 320, 161-174).

Beta catenin is expressed throughout the adult liver. In hepatocytes, it is at the cell surface throughout the hepatic lobule. Beta catenin signaling is crucial for the repair/regeneration of the liver especially following surgical resection, toxic insult, infection, metabolic insult, or tumor. Beta catenin signaling is regulated through WNT signaling and WNT-independent pathways. Beta catenin can be activated via several different pathways, although the WNT signaling pathway has been the most widely studied. Zonation of hepatic lobule requires expression of specific genes in pericentral vs periportal hepatocytes for optimum hepatic function in regulating metabolism. WNT signaling might link several processes linked with NASH pathogenesis including altered glucose and lipid metabolism. WNT-β-catenin signaling is implicated in Hepatic adenomas, FNH and its role in liver fibrosis is just beginning to be investigated. Prior studies show distinctive patterns of β-catenin signaling and mutations in HCC. The various mechanisms of β-catenin activation in HCC have a distinct impact on tumor phenotype. The overall effects of β-catenin mutations and activation in patients with HCC, and how these affect their prognosis are still being debated. Changes in the expression and activity of β-catenin affect hepatic pathophysiology. The specific WNT proteins that modulate β-catenin activity is still not known completely. Preliminary data shows that activation of β-catenin could induce liver regeneration. Triiodothyronine can activate β-catenin in rodents.

Triiodothyronine (T3) induces hepatocyte proliferation in rodents. T3 has mitogenic effects through in large part via activation of β-catenin signaling. The hepatocytes mostly express T3 hormone receptor β (TRβ). GC-1 is a selective TRβ agonists which has β-catenin-dependent hepatocyte proliferation effect. A study shows that TRβ-selective agonists like GC-1 can induce hepatocyte proliferation through β-catenin activation in rodents via Wnt-dependent and Wnt-independent mechanisms and confer a regenerative advantage following surgical resection. The development of alternative methods of treatment of liver disease and regeneration is in great demand. The emerging field of regenerative medicine offers novel approaches. Regenerative response to partial hepatectomy involves numerous coordinated events occurring at the molecular, cellular, biochemical and tissue levels. Hepatocyte hypertrophy starts within hours after partial hepatectomy and is followed by hepatocyte hyperplasia. Restoration after injury involves restitution of all functions of normal liver including synthetic and metabolic function. GC-1 can accelerate liver regeneration which could be potentiate the normal physiological process.

EXAMPLES

Example 1

Materials and Methods

Animals.

All studies on mice were performed in strict accordance with Guidelines. Eight-week old male C57BL/6 male mice (Jackson/Charles River) were maintained on a standard laboratory basal diet (Test Diet) (n=4), or fed a T3-supplemented diet (4 mg/Kg of diet, Sigma Chemicals, St. Louis Mo.) (n=4). GC-1 was administered to the eight week-old male C57BL/6 male mice either via GC-1-supplemented diet (5 mg/Kg of diet, Medchem Express) for 8 days (n=4) or via daily intraperitoneal injections (IP) of GC-1 dissolved in DMSO (0.3 mg/kg/dose) for 8 days (n=7). As a control group for injections, DMSO alone was injected daily intraperitoneal (IP) for 8 days (n=5). Mice were sacrificed 24 hours after the last injection.

Eight to 10 week old male hepatocyte specific β-catenin knockout mice (β-cat-LKO) or sex-matched littermate controls obtained from breeding homozygous floxed β-catenin mice and albumin-cre transgenic mice (as described elsewhere (Tan et al., (2006) *Gastroenterology* 131, 1561-1572)) were given 8 daily IP injections of GC-1 (n=4) or DMSO (n=4) and harvested around 24 hours after the last injection.

Eight to 10 week-old LRP5-6-LKO were obtained from breeding homozygous LRP5-6 double floxed mice with albumin-cre transgenic mice as described previously (Yang et al. (2014) *Hepatology* 60, 964-976). LRP5-6-LKO or sex matched littermate controls were given either T3-supplemented diet (n=4), basal diet (n=3), IP GC-1 (n=3) or IP DMSO (n=3). Mice were sacrificed at 24 hours after the last IP injection.

To label dividing hepatocytes, BrdU (5-bromodeoxyuridine) dissolved in drinking water (1 mg/ml) was given to all animals throughout the experiment period. The animals were given food and water ad libitum with a 12-hour light/dark daily cycle.

Partial Hepatectomy.

After 7 days of receiving T3 supplemented diet (n=3) or GC-1 diet (n=3) or standard basal mouse chow (n=3), C57BL/6 male mice underwent partial hepatectomy as described previously (Tan et al. (2006) *Gastroenterology* 131, 1561-1572). Anesthesia was provided with inhaled Isoflurane. The animals were sacrificed 24 hours post hepatectomy, after Isoflurane anesthesia and cervical dislocation. Serum and liver tissue were harvested for further processing.

Immunohistochemistry.

Four micron liver sections were analyzed by immunohistochemistry for β-Catenin (BD Biosciences, San Jose, Calif.), Cyclin-D1 (Thermo-Scientific, Fremont, Calif.) and PCNA (Santa Cruz Biotechnology, Dallas, Tex.). Briefly, formalin-fixed sections were deparaffinized in graded xylene and alcohol. Endogenous peroxidase was inactivated using 3% hydrogen peroxide (Sigma). For β-Catenin, Cyclin-D1 staining, slides were microwaved in Citrate buffer followed by blocking with Superblock for 10 minutes. Sections were then incubated with secondary anti-mouse (for β-catenin) or anti-rabbit (for Cyclin-D1) horseradish peroxidase-conjugated antibody for 30 minutes.

For PCNA, slides were microwaved in zinc sulfate for 12 minutes, followed by blocking with Superblock for 20 minutes. Sections were incubated with PCNA antibody (Santa Cruz) diluted 1:4,000 in phosphate buffered saline (PBS) for 60 minutes. Slides then incubated with horse anti-mouse secondary antibody (1:700 dilution) for 30 minutes. ABC was applied for 30 minutes. DAB kit was then applied. Slides were then dehydrated, coverslips placed, and allowed to dry.

Bromodeoxyuridine (BrdU) was stained with mouse antibody (Becton Dickinson) as previously described (Fanti et al. (2014) *Hepatology* 59, 2309-2320). Briefly, tissue sections were deparaffinized, exposed to 0.3% hydrogen peroxide in deionized water for 10 minutes to block endogenous peroxidase, treated with 2N HCl, incubated with trypsin 0.1% for 20 minutes and then with normal goat serum for 20 minutes at room temperature. Sections were then incubated overnight in cold room with anti-BrdU monoclonal antibody, followed by biotinylated goat anti-mouse IgG. DAB kit was then applied, and sections were counterstained with hematoxylin. A small segment of intestine was included from each mouse as a positive control for the staining. For quantification of BrdU staining, at least 10 high power fields (400× or 600×) fields each from at least three biological replicates were counted as indicated in the figures. Statistical analysis was performed as described below.

Protein Extraction and Western Blot Analysis.

Protein extraction from frozen liver tissue and western blot analysis were performed as previously described (Fanti et al., (2014) *Hepatology* 59, 2309-2320). For protein extraction, a small amount of frozen liver tissue was obtained (over dry ice) and was homogenized using RIPA buffer with protease and phosphatase inhibitor cocktail (Sigma, St. Louis, Mo.). Samples were transferred to a 1.5 ml tube on ice, and spun in cold room centrifuge at 14,000 RPM for 5 minutes. Pellet was then discarded and sample was aliquoted and stored at −80 C for use. Fifty micrograms of the proteins were resolved by sodium dodecyl sulfate-polyacrylamide gel electrophoresis analysis, and transferred to immobilon-polyvinylidene difluoride membranes.

The primary antibodies used were against β-catenin (BD Biosciences); pSer675-β-catenin, pSer552-β-catenin, Active-β-catenin (Cell-Signaling), Cyclin-D1 (Thermo-Scientific), and β-Actin (Sigma). Dilutions of primary antibody were done according to manufacturer recommendations (1:1000 for all except Cyclin-D1 which was 1:200). Horseradish peroxidase-conjugated secondary antibodies used were goat anti-mouse (1:20,000) and goat anti-rabbit (1:10,000) (Millipore). The proteins were detected by SuperSignal West Pico Chemiluminescense Substrate (Thermo Scientific, Rockford Ill.) and visualized by autoradiography.

Real Time Polymerase Chain Reaction (PCR).

Total RNA was extracted by homogenizing frozen liver tissues in Trizol reagent (Invitrogen, Carlsbad, Calif.) from GC-1-injected β-Cat LKO (n=4) and littermate control mice (n=4); and GC-1-injected LRP5-6 LKO (n=3) and littermate control mice (n=3). Two micrograms of total RNA from each sample was reverse-transcribed after DNAse treatment using Super Script III first strand kit (Invitrogen). Real-time PCR was performed on an ABI Prism 7300 Sequence Detection System (applied Biosystems, Foster City, Calif.) using SYBR Green. For Cyclin-D1, values were normalized to GAPDH.

Statistics.

Data are presented as mean±SD or SE as indicated. All statistics were performed using Prism 6 software (GraphPad) for Mac OS X. Comparisons between various groups were performed by Student t test (for two groups) or ordinary one-way ANOVA for multiple comparisons. Analysis for significance was done by Tukey's multiple comparisons test. P values of <0.05 (*), <0.01 (), <0.001 (*) and <0.0001 (****) were considered significant throughout the study.

Example 2

Figure 1A:
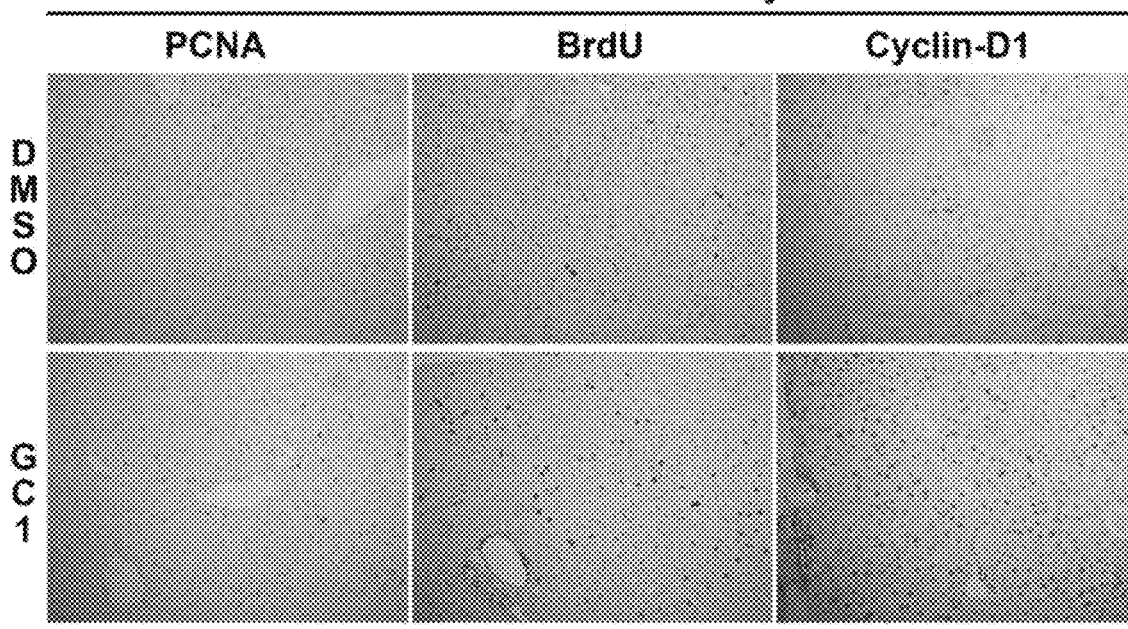
FIGS. 1A-1D. Thyroid hormone receptor β-agonist GC-1 induces hepatocyte proliferation in wild type mice. A. Representative photomicrographs (100×) of immunohistochemistry for BrdU and PCNA showed increased proliferation in GC-1 treated mouse livers compared with DMSO controls.
Figure 1B:
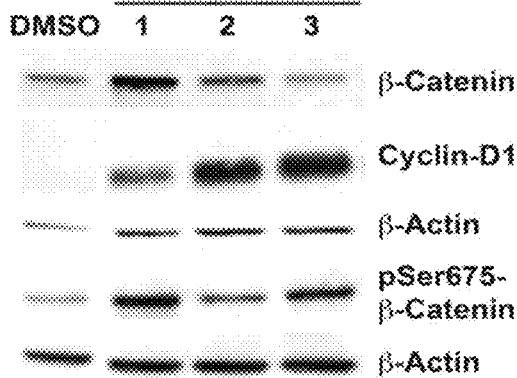
Figure 1C:
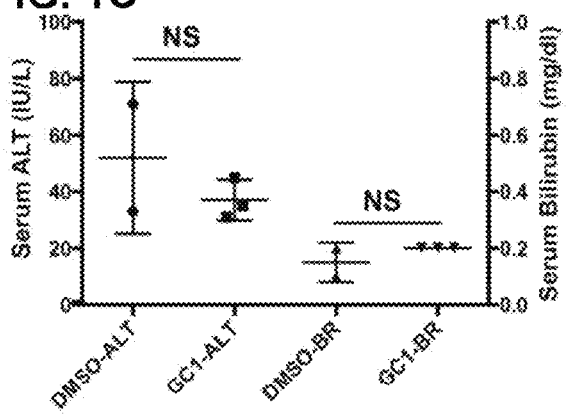
Figure 1D:
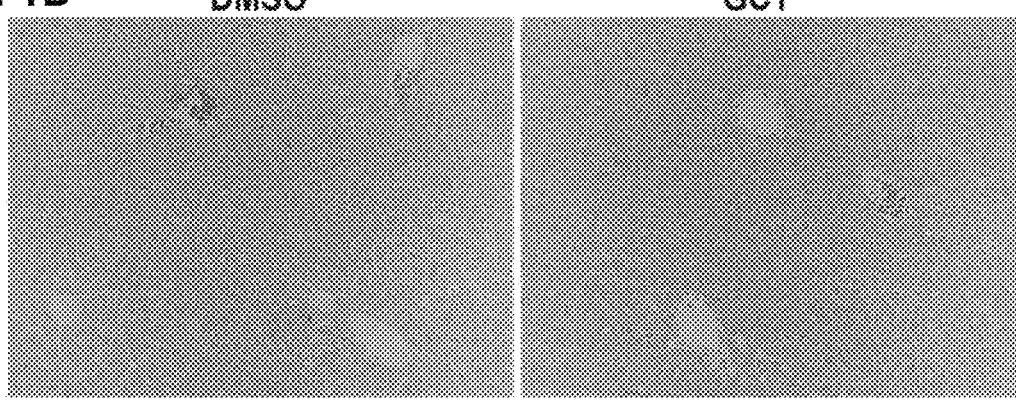

GC-1 Treatment Induces Hepatocyte Proliferation, β-Catenin Activation, and Cyclin-D1 Expression in Wild Type Mice without Evidence of any Liver Injury T3 hormone was previously shown to exert a strong mitogenic effect over hepatocytes in rats and mice, and this action has been shown to require β-catenin activation (Fanti et al. (2014) Hepatology 59, 2309-2320). To determine if TRβ-agonist GC-1 also causes hepatocyte proliferation, an experiment with normal mice was first performed. Two to three-month old C57BL/6 mice received daily intraperitoneal (IP) injections with GC-1 (0.3 mg/Kg/dose) dissolved in dimethyl sulfoxide DMSO, or DMSO alone as control. The results showed increased number of PCNA-positive hepatocytes as well as BrdU incorporation in GC-1 group showing an increase in hepatocyte proliferation in this group as compared to the DMSO control (FIG. 1A). Immunohistochemistry for cyclin-D1 also showed many positive hepatocytes in GC-1 but not DMSO control (FIG. 1A). Western Blot analysis using whole cell lysates from the livers from the two groups showed increased P-Ser675-β-catenin and cyclin-D1 levels in GC-1 treated group while total β-catenin levels did not show much difference (FIG. 1B). Serum analysis from the two groups of mice showed insignificant differences in serum ALT or total bilirubin, which remained normal (FIG. 1C). Further, normal hepatic histology comparable to DMSO injected control was evident in GC-1 group as shown in representative H&E staining (FIG. 1D). Thus GC-1 administration by daily IP injections induces hepatocyte proliferation through activation of β-catenin and increased cyclin-D1 without any untoward biochemical or histological consequences.

Example 3

GC-1 Induces Hepatocyte Proliferation

An initial comparison of T3 supplemented diet versus IP GC-1 for 8 days with ad libitum access to BrdU containing drinking water showed an overall fewer number of BrdU-positive hepatocytes indicating lesser proliferation in the GC-1 treated group (FIG. 2A). This went along with notably increased cyclin-D1 staining in hepatocytes after T3 and GC-1 as compared to their respective controls, although greater numbers of positive cells were evident in the T3 group (FIG. 2A). When BrdU-positive hepatocytes were carefully counted in T3-fed and GC-1-injected groups, the difference between the two groups was statistically significant (p<0.001) (FIG. 2B). Interestingly however, a decrease in the number of BrdU labeled hepatocyte nuclei was also observed in the DMSO injected mice when compared to mice on basal diet and this difference was also statistically significant (FIG. 2B).

Differences between the mode of drug delivery plus the finding of lower basal level of proliferating cells in the DMSO group prompted us to compare hepatocyte proliferation in mice administered T3 and GC-1 via supplemented diets. Normal male mice were fed regular rodent chow, T3-supplemented (4 mg/Kg of diet) chow, or GC-1-supplemented (5 mg/Kg of diet) chow for 8 days. As with GC-1 IP injection, no histological changes in the livers were observed after GC-1 or T3 feeding as compared to the control basal diet (FIG. 3A). Mice fed T3 or GC-1 supplemented diets showed increased BrdU incorporation when compared to basal diet-fed controls (FIG. 3B). Cyclin-D1 staining in hepatocytes was increased in both groups as compared to basal diet (FIG. 3B). However, when BrdU-positive hepatocytes were counted, a significant difference in BrdU incorporation was continuously observed between T3 versus GC-1 diet groups (FIG. 3C), although the discrepancy was less than what was observed in T3 diet fed versus GC-1 injected group. Thus, GC-1 induces hepatocyte proliferation via β-catenin activation and cyclin-D1 expression, although to modestly less extent than T3.

Example 4

Presence of β-Catenin is Required for Significant Level of Proliferation in Response to TRβ Agonist GC-1

T3 hormone has been shown to require β-catenin to exert mitogenic effect in mouse hepatocytes (Fanti et al. (2014) Hepatology 59, 2309-2320). Thus, it was determined whether the action of selective TR3 agonist would similarly be dependent on β-catenin. β-Cat LKO mice and wild type littermate controls received eight daily IP injections of GC-1 (0.3 mg/Kg/dose) or DMSO alone (control) as described in methods. Similar to T3, GC-1 treated β-Cat LKO mice showed decreased hepatocyte proliferation as shown by low BrdU incorporation in hepatocytes in β-Cat LKO as compared to controls (FIGS. 4A-B). However, notable BrdU incorporation continued to occur in the non-parenchymal cell population in the β-Cat LKO group after GC-1 administration. Both findings were similar to those observed after T3 administration to β-Cat LKO (Fanti et al., supra).

Consistent with the lack of optimum BrdU response to GC-1, the β-Cat LKO livers also showed a notable decrease in nuclear cyclin-D1 by immunohistochemistry when compared to controls, similar to that observed in response to T3

(FIG. 4C). This was verified by RT-PCR analysis, which showed a significant decrease in cyclin-D1 mRNA expression in β-catenin-LKO mice receiving GC-1 compared to controls (FIG. 4D).

Lastly, the status of PKA-dependent serine phosphorylation of β-catenin in β-Cat LKO was addressed following GC-1 and T3 treatment. Western blot analysis using liver lysates from β-Cat LKO and control mice treated with T3 or GC-1 showed notably lower total β-catenin in KO, which represents continued β-catenin expression in the non-parenchymal cells as also noted elsewhere (Tan et al. (2006) *Gastroenterology* 131, 1561-1572) (FIG. 4E). As expected, P-Ser675-β-catenin was absent in β-Cat LKO as compared to controls treated with GC-1 or T3. Intriguingly it was found that β-cat LKO mice that received T3 or GC-1 showed even higher levels of P-Ser552-β-catenin levels as compared to controls subjected to similar treatment (FIG. 4E). These findings suggest a divergence in PKA-dependent β-catenin activation in response to T3 or GC-1 in hepatocytes versus non-parenchymal cells that may eventually be contributing to their overall mitogenic response in the liver.

Example 5

Lack of Hepatocyte Proliferation in Response to Both T3 and GC-1 Upon Disruption of Wnt-β-Catenin Axis in the Hepatocytes Previous work and the work disclosed herein show that like T3, GC-1 also increases phosphorylation of β-catenin at Ser675. To further substantiate these results, it was directly investigated if Wnt-dependent β-catenin activation could be contributing to the overall mitogenic effect of T3 and GC-1. For this, LRP5-6 LKO mice were utilized that lack the two redundant Wnt co-receptors (LRP5 and LRP6). These mice, unlike n-Cat LKO have intact β-catenin in hepatocytes, however the absence of Wnt co-receptors, disallows β-catenin activation in hepatocytes in response to Wnt secretion (Fanti et al., supra).

LRP5-6 LKO male mice and littermate controls aged 2-3 months received either T3 supplemented diet (4 mg/Kg of diet) or regular control diet. Another cohort received 8 daily IP injections of GC-1 (0.3 mg/Kg/dose) or DMSO. Interestingly, LRP5-6 LKO mice treated with either T3 or GC-1 showed a notable decrease in the number of BrdU-labeled hepatocyte nuclei when compared with the controls (FIG. 5A). A careful counting of the BrdU-positive hepatocytes verified a significant difference in hepatocyte proliferation in response to T3 and GC-1 as compared to controls (FIG. 5B), and occurred with the same profoundness in response to T3 or GC-1 in the absence of LRP5-6 in hepatocytes (FIG. 5C). Likewise, the numbers of cyclin-D1-positive hepatocytes was also notably decreased in LRP5-6 LKO in response to T3 and GC-1 as shown by immunohistochemistry (FIG. 5A).

Figure 6A:
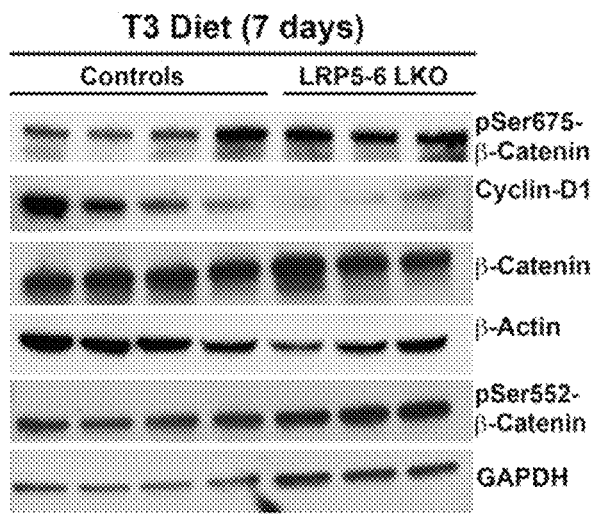
Figure 6B:
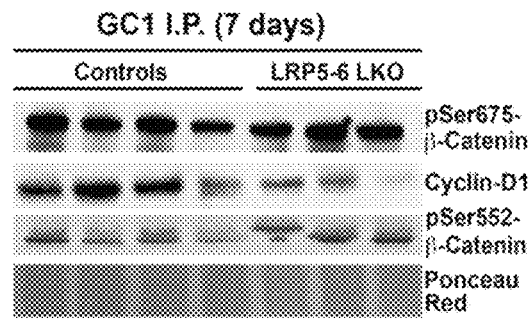
Figure 6C:
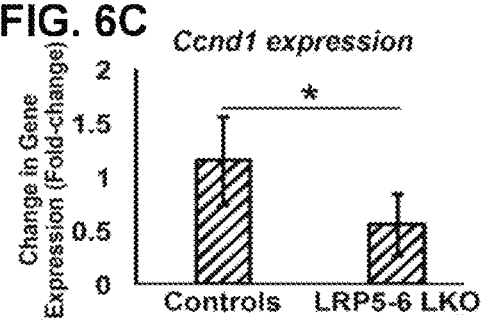

The mechanism of this unexpected finding was explored. It was determined if β-catenin levels were any different in LRP5-6 LKO. As expected, comparable levels of total β-catenin was found in the LRP5-6 LKO in control and T3 group (FIG. 6A) and GC-1 group. Further, in agreement with immunohistochemistry findings (FIG. 5A), LRP5-6 LKO showed decreased cyclin-D1 protein and mRNA expression in response to both T3 and GC-1 by Western blots as well (FIGS. 6A, 6B, and 6C). Interestingly, either comparable or even greater levels of pSer675-β-catenin were evident in LRP5-6-LKO and littermate controls treated with GC-1 and T3 (FIGS. 6A, 6B). There was a modest increase in the levels of pSer552-β-catenin in LRP5-6 LKO after both T3 and GC-1 (FIGS. 6A, 6B).

Figure 6D:
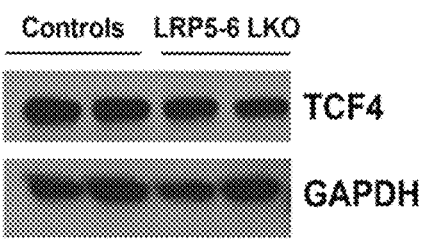

Because cyclin-D1 expression is regulated by β-catenin interaction with transcription factor TCF4, the liver lysates were assayed from the LRP5-6 LKO for the levels of TCF4. Comparable levels of total TCF4 were evident in the LRP-LKO and controls (FIG. 6D).

Figure 6E:
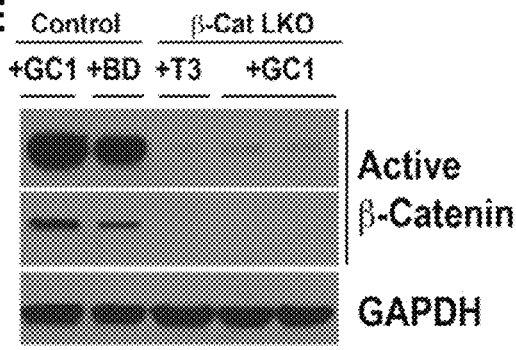
Figure 6F:
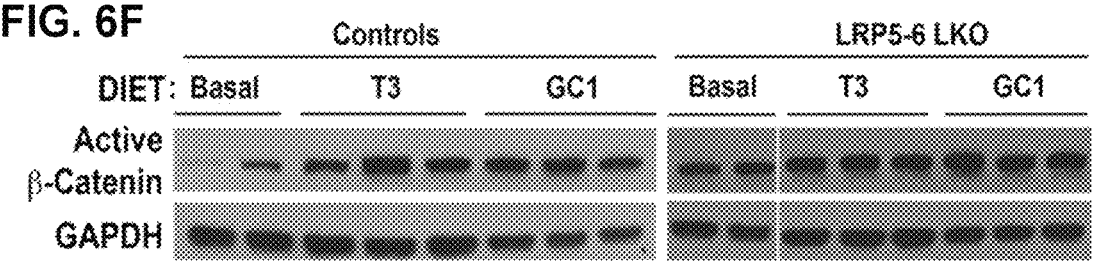

Because β-catenin-LKO and LRP5-6 LKO both are refractory to T3 and GC-1 treatment in terms of hepatocyte proliferation due to impaired cyclin-D1 induction, it was determined whether intact Wnt signaling was also contributing to β-catenin activation in addition to PKA-dependent β-catenin activation, as evidenced by increased pSer675-β-catenin. For this study, an antibody against active β-catenin (hypophosphorylated at Ser33, Ser37 and Thr41) was used. To check the specificity of this antibody, liver lysates were used from β-Cat LKO and controls treated with T3, GC1 or basal diet. A notable increase in active-β-catenin was evident in GC-1 treated group as compared to basal diet (FIG. 6E). A very faint signal presumably due to non-parenchymal cells, was evident in β-Cat LKO after T3 or GC-1 treatment indicating the specificity of the antibody (FIG. 6E). Next, it was determined if intact Wnt signaling is required to activate β-catenin in hepatocytes after T3 or GC-1 treatment. A dramatic increase in active β-catenin levels was evident in liver lysates of control mice fed T3 or GC-1 diet for 8 days as compared to basal diet fed mice (FIG. 6F). However, no notable differences in active β-catenin levels were evident in LRP5-6 LKO after T3 or GC-1 feeding when compared to basal diet (FIG. 6F).

Taken together, these findings suggest that hepatocyte proliferation in response to both T3 and GC-1 may eventually be a net result of PKA- and Wnt-dependent β-catenin activation.

Example 6

Pretreatment with T3 or GC-1 Supplemented Diet Prior to Partial Hepatectomy Leads to a Proliferative Advantage at 24 Hours Post Hepatectomy in Mice To directly investigate any significance of T3 or GC-1 in hepatic regenerative therapies, their usage in partial hepatectomy model was investigated. Because the kinetics of hepatocyte proliferation during liver regeneration after partial hepatectomy in C57BL/6 mice are well known, it was determined if T3 or GC-1 pre-treatment of mice offers any regenerative advantage in the setting of partial hepatectomy, a procedure relevant in patients as well. Two-month old C57BL/6 mice were put on T3-diet, GC-1-diet or kept on basal diet for 7 days with drinking water containing BrdU ad libitum. On day 7, all mice were subjected to two-thirds hepatectomy and resected lobes retained for analysis for BrdU and cyclin-D1 by immunohistochemistry. Hepatectomized mice from all three groups were sacrificed 24 hours later, a time-point around 12-16 hours prior to the observed peak hepatocyte proliferation (Fausto (2000) *J Hepatol* 32, 19-31; Michalopoulos (2013) *Compr Physiol* 3, 485-513). Livers from 24 hour time point were assessed for BrdU incorporation in hepatocytes and cyclin-D1 by immunohistochemistry. Seven-day pretreatment of mice with either T3 or GC-1 led to increased BrdU-positive hepatocytes as compared to basal diet as observed in the analysis of resected lobes (FIG. 7A). Interestingly, while very few hepatocytes showed BrdU positive nuclei at 24 hours after hepatectomy in mice fed basal diet, a pronounced increase was observed in T3 as well as GC-1-fed group of animals (FIG. 7A). In fact, the numbers of hepatocytes positive for nuclear BrdU were significantly higher in T3 and GC-1 fed mice versus basal diet (FIG. 7B). T3 pretreatment showed significantly greater hepatocyte proliferative response than GC-1 post hepatectomy (FIG. 7B).

Cyclin-D1 was assessed in the same groups by immunohistochemistry. Cyclin-D1 was restricted to a subset of midzonal hepatocytes in basal diet fed mice both in resected lobes as well as regenerating lobes at 24 hours (FIG. 7C). An expansion of cyclin-D1 positive hepatocytes in the midzonal area was evident in both T3 and GC-1 pretreatment livers in the resected lobes at the time of hepatectomy (FIG. 7C). However, at 24 hours after hepatectomy, a panlobular distribution of hepatocytes with nuclear cyclin-D1 was clearly evident in the livers from T3 as well as GC-1 treated mice. (FIG. 7C).

Finally, change in BrdU incorporation was determined longitudinally in the same animals in basal diet, T3 and GC-1 groups to address their relative efficacy in inducing hepatocyte proliferation over 24 hours during liver regeneration. No significant differences were observed in hepatocyte proliferation between pre-hepatectomy and 24 hour-post hepatectomy livers in animals that were on basal diet (FIG. 8A). T3 induced significant increase in hepatocyte proliferation which was around 2-fold over the 24-hour liver regeneration period in all three mice tested (FIG. 8B). Similarly, GC-1 also induced a significant increase in hepatocyte proliferation of around 2-fold over its baseline within 24 hours during liver regeneration in all three animals tested (FIG. 8C). Thus both T3 and GC-1 pretreatment offered a regenerative advantage to the liver following surgical resection in mice.

Thus, selective thyromimetics activating TRβ in the liver are effective in inducing hepatocyte proliferation. The hepatocyte proliferation induced by GC-1 could be dependent on the presence of β-catenin. Indeed, the results show that GC-1 is capable of inducing β-catenin activation, which in turn increased Cyclin-D1 expression and eventually hepatocyte proliferation, when given either as an injection or as a diet. Intriguingly, GC-1 when delivered IP in DMSO showed lesser increases in hepatocyte proliferation than its delivery orally through diet. This was most likely due to the use of DMSO as a solvent for GC-1. This was strengthened by the observation that DMSO delivery by itself affected hepatocyte proliferation. Indeed, the role of DMSO in inhibiting hepatocyte proliferation especially in cultures has been known for a long time (Chan et al. (1989) *J Cell Physiol* 141, 584-590). When GC-1 was administered to mice via diet, hepatocyte proliferation was increased to a notably greater extent, although it was less so than that induced with T3-diet. This could be due to the dose of GC-1 in diet or other mechanisms, especially since a previous study has reported comparable efficacy of T3 and GC-1 in inducing hepatocyte proliferation (Kowalik et al. (2010) *J Hepatol* 53, 686-692). Nonetheless, GC-1 administration caused a profound increase in hepatocyte proliferation.

This study also elucidated the mechanism by which T3 and selective thyromimetics cause hepatocyte proliferation. In order to identify if β-catenin is also required for the actions of GC-1, GC-1 was administered to β-cat-LKO mice and controls. The results showed that, similar to T3, there was a significant decrease in proliferation in response to GC-1 when β-catenin is absent from hepatocytes. This occurred concomitant to lack of Cyclin-D1 increase in hepatocytes, which is a known β-catenin target (Tan et al., supra). To further try and characterize the mechanism of β-catenin activation by the thyromimetics like T3 and GC-1, a mouse model was used that has conditional loss of Wnt co-receptors LRP5 and LRP6 in hepatocytes and has been described by us recently (Yang et al. (2014) *Hepatology* 60, 964-976). In the absence of these co-receptors, Wnt is unable to transduce its signal to β-catenin (Riddle et al. (2013) *PloS one* 8, e63323). However, β-catenin is present in hepatocytes and hence may be capable of being activated by non-Wnt mechanisms. Based on the previously proposed mechanism involving PKA-dependent phosphorylation of β-catenin, treatment of LRP5-6 LKO mice with T3 or GC-1 could result in a similar degree of hepatocyte proliferation when compared to the control mice. Intriguingly, the results show that LRP5-6 LKO mice have significantly reduced hepatocyte proliferation in response to T3 or GC-1 when compared to controls along with decreased Cyclin-D1 in hepatocyte nuclei. Furthermore, this occurred despite comparable levels of TCF4 and equally increased levels of pSer675-β-catenin in LRP5-6 LKO mice. This suggests that T3 and GC-1 induced β-catenin activation brought about via PKA activation is intact in the absence of LRP5-6 in hepatocytes. To address the discrepancy of low regenerative response in LRP5-6 LKO following GC-1 and T3, the effect of these factors on canonical Wnt signaling was revisited. The effect of T3 on Wnt-dependent β-catenin activation was previously studied by only assessing any changes in levels of Ser9-GSK3β (Fanti et al., supra). However, this phosphorylation site at GSK3β has been shown to be inconsequential in Wnt signaling and only relevant in Insulin signaling (McManus et al. (2005) *The EMBO journal* 24, 1571-1583). In the studies disclosed herein an antibody was used that detects β-catenin which is hypophosphorylated at Ser33, Ser37 and Thr41, which is a direct consequence of Wnt signaling (Villar et al. (2011) *PloS one* 6, e23914). The specificity of this antibody was verified using β-catenin LKO. Further, a notable increase in active-β-catenin levels following GC-1 treatment in normal animals was observed. In absence of LRP5-6 on hepatocytes, there was a failure of any increase in active-β-catenin levels in response to T3 and GC-1. Without being bound by theory, these findings suggest that T3 and TRβ-agonists require both intact Wnt signaling as well as PKA to allow for optimal β-catenin activation and hepatocyte proliferation (FIG. 9).

The mechanism wherein T3 or GC-1 cause Wnt-dependent β-catenin activation was investigated. In liver regeneration after partial hepatectomy, non-parenchymal cells (NPC) such as sinusoidal endothelial cells and macrophages are the source of Wnts which activate β-catenin in hepatocytes in a paracrine manner (Yang et al. (2014) *Hepatology* 60, 964-976; Ding et al. (2010) *Nature* 468, 310-315). NPC proliferation in response to T3 and GC-1 was observed. Thus, thyromimetics may also be contributing to β-catenin activation and hepatocyte proliferation indirectly by inducing Wnt secretion from NPCs (FIG. 9).

An increase in the levels of pSer552-β-catenin was observed in β-catenin-LKO and LRP5-6-LKO mice following treatment with T3 and GC-1, which was unexpected. This site can also lead to β-catenin activation (Taurin et al., (2006) *J Biol Chem* 281, 9971-9976). Intriguingly, this increase was evident even in livers that lacked β-catenin in hepatocytes and hence this observation most likely represents β-catenin phosphorylation and activation in the non-parenchymal cells of the liver following GC-1 and T3 treatment. Without being bound by theory, it is conceivable that T3 and GC-1 may be stimulating proliferation of non-parenchymal cells such as endothelial cells by β-catenin activation through phosphorylation at Ser552. Also, thyromimetics may induce release of Wnt proteins from endothelial cells, which could them contribute to eventually contribute to endothelial cell proliferation in an autocrine manner and to hepatocyte proliferation in a paracrine fashion through stimulation of the canonical Wnt signaling pathway (FIG. 9).

The last part of the disclosed study directly investigated whether pretreatment with T3 or GC-1 prior to partial hepatectomy would confer a regenerative advantage to mice. The effect of T3 on liver regeneration has been examined in rats previously, and those results did show a regenerative advantage after partial hepatectomy, and a survival advantage in a 90% hepatectomy model, which is normally associated with high mortality (Columbano et al. (2008) *Cell Prolif* 41, 521-53). The results show significantly increased BrdU incorporation in hepatocytes 24 hours after partial hepatectomy in mice that received T3- or GC-1-supplemented diet for 8 days prior to the surgery. Even though this is a nonlethal model and mouse livers typically regenerate within 14 days, a clear and robust regenerative response was shown following T3 or GC-1 pre-administration. This was again due to increased expression of Cyclin-D1. This part of the study demonstrates the direct relevance of administration of thyromimetics in the setting of liver transplantation to induce regeneration in the donor and/or recipient.

Thus, like T3, GC-1 causes pronounced hepatocyte proliferation secondary to increased Cyclin-D1 expression that is dependent on activation of β-catenin. It was found that disrupting Wnt signaling abolishes GC-1- and T3-dependent β-catenin activation. The efficacy of these agents to induce hepatocyte proliferation and stimulate the process of liver regeneration was validated, which has significant therapeutic implications in the transplantation settings.

Example 7

The mitogenic effects of TRβ-selective agonist GC-1 in hepatocyte regeneration and proliferation in liver donors are determined prior to hepatectomy. The effectiveness of GC-1 therapy, when given prior to hepatectomy in the selected liver donors leads to accelerated physiological regeneration, and provides a proliferative advantage when compared to the control group. GC-1 is also used in patients post living donor recipients. GC-1 accelerates the liver regeneration or proliferation. GC-1 is also used in post liver transplant patients with Small for Size syndrome. In addition, GC-1 is used in liver transplant recipients who received extended criteria livers.

Example 8

The effects of GC-1 are evaluated on lipid profile and liver function tests post hepatectomy. Ancillary studies are performed of the pathogenesis, diagnosis or diagnostic biomarker development, natural history and treatment of GC-1. In addition, the following is investigated:
1. Non-alcoholic fatty liver disease (NAFLD)/or liver injury for other reasons
2. Acute Alcoholic Hepatitis (AAH)
3. Fulminant Hepatic Failure (FHF)
4. Tylenol induced liver injury (LI) or
5. Patients post liver transplant (LT) with cholestasis or Drug Induced Liver Injury (DILI) or Total Parenteral Nutrition (TPN) induced liver injury (LI).

Example 9

An intravenous (IV) infusion is used, such as GC-1 (0.3 mg/kg/dose) dissolved in a solvent (DMSO). GC-1 is administered Day #1 after hepatectomy in donors or hepatectomy for other reasons. The duration can be one, two or three weeks. In some examples, subject who are liver transplant recipients from extended criteria donors are treated.

A liver biopsy is taken during the initial procedure. Imaging and laboratory tests are used to determine synthetic/metabolic function post-operatively in the non-GC-1 administered control group Vs GC-1 group and follow the liver proliferation and regeneration.

Example 10

Partial Hepatectomy Study in Mice

Seven days prior to surgery, mice are initiated on GC-1 containing diet (5 mg/kg). Diet is made available ad libitum. Surgery is performed at day 7. The mice continue to be on GC-1 diet. Three mice will be sacrificed at 12 hours, 3 mice at 24 hours, 3 mice at 48 hours, 3 mice at 7 days and 3 mice at 14 days. Blood is analyzed at all these times for serum albumin, serum ALT levels, serum AST levels, prothrombin time/INR (international normalized ratio), bilirubin and glucose and lipid profiles. Livers harvested at each time point are assessed for weight (body weight), hepatocyte proliferation, Wnt target genes and gene expression studies. These studies directly test prolonged benefit of GC-1 on liver regeneration.

Example 11

Promoting Regeneration to Treat Hepatic Steatosis

Long term regeneration in mice is associated with steatosis (one year after partial hepatectomy). GC-1 is used for 10 days after partial hepatectomy only and then mice are followed for 1 year to examine steatosis. In second group of mice, surgery is performed and 11.5 months after surgery, and these mice are randomized into 2 groups—one is put on GC-1 diet and other on regular diet for 15 days before sacrificing. The livers are examined for the same parameters as in Example 11 and are examined for fat deposition by H&E as well as oil red o staining. In addition, serum and liver are examined for triglycerides, HDL, VLDL and cholesterol. Increased hepatocyte proliferation, improved serum biochemistry and decreased serum and hepatic lipids in GC-1 group show an advantage of use of GC-1 in steatosis by promoting regeneration.

Example 12

Acetaminophen (APAP) Overdose a. Sublethal dose: Mice are on GC-1 diet or basal diet for 7 days. On day 7, they are overnight fasted and injected intraperitoneally with a sublethal dose of APAP at 300 mg/kg body. Mice (n=3/time point/group-basal diet versus GC-1) are sacrificed at 6 hours (h) and 12 h. Additional mice from each group are provided GC-1 or basal diet after 6 hours of APAP injection and 3 mice from each group are killed at 24n and 48 h to test for serum albumin, serum ALT levels, serum AST levels, prothrombin time/INR (international normalized ratio), bilirubin and glucose and lipid profiles. Liver weight/body weight ratio is assessed and liver histology and markers for liver regeneration are assessed at all times. Increased hepatocyte proliferation, improved liver weights and improved serum biochemistry in GC-1 group advantage of use of GC-1 in APAP overdose.

b. Lethal dose: Mice are on GC-1 diet or basal diet for 7 days. On day 7, they are overnight fasted and injected intraperitoneally with a lethal dose of APAP at 450 mg/kg body. Mice (n=3/time point/group-basal diet versus GC-1) are sacrificed at 6 h and 12 h. Additional mice from each group are provided GC-1 or basal diet after 6 hours of APAP injection and 3 mice from each group are killed at 24 h and 48 h to test for serum albumin, serum ALT levels, serum AST levels, prothrombin time/INR (international normalized ratio), bilirubin and glucose and lipid profiles. Liver weight/body weight ratio is assessed and liver histology and markers for liver regeneration are assessed at all times. Mice are expected to perish in the basal diet group by 12-24 h. Survival advantage will be assessed by Kaplan Meier analysis of GC-1 versus basal diet groups. Increased hepatocyte proliferation, improved liver weights, improved survival and improved serum biochemistry in GC-1 group advantage of use of GC-1 in APAP overdose.

Example 13

Clinical Trial

Role for the Potential Applications in Transplant Population:
  There is an unmet clinic need and utility in transplant population in areas of liver regeneration and liver regeneration. GC-1 can be utilized in a transplant population including:
  Living donors prior to donor surgery
  Living donor recipients
  Post hepatectomy patients for other reasons like Hepatoblasotoma, hepatic adenoma etc.
  Post liver transplant cadaveric recipients with SFSS (Small for size syndrome)
  Extended criteria donor livers including DCD donors given the scarcity of organs and increased wait list mortality
  Utility in high risk donors: Marginal or extended criteria donors (ECD) are defined as those with a greater risk of initial poor function or graft failure and therefore an increased risk for recipient morbidity and mortality
  The features of a marginal organ have not been clearly defined, although some circumstances are known to be related to impaired graft function: elderly donors, a high grade of steatosis, DCD/non-heart-beating donors, or split grafts
  In donors with high DRI (Donor risk index)
Dosage of GC-1
  Intravenous (IV) infusion
  GC-1 (0.3 mg/kg/dose) dissolved in a solvent (DMSO or saline) as an IV infusion, typically on Day #1 after hepatectomy in donors or hepatectomy for other reasons
  Patients who are liver transplant recipients from extended criteria donors
  Duration: 2 weeks
  Liver biopsy intra op and imaging and other labs to check synthetic/metabolic function post operatively.
  Control Vs GC-1 group and follow the liver proliferation and regeneration
Study Overview
  Compare liver regeneration in 10 patients who will be IV infused GC-1 (0.3 mg/kg/day)×7 days starting day 1 after transplantation to 10 patients without GC-1. Liver regeneration will be measured by radiological monitoring of hepatic size and hepatic function (serum albumin, Prothrombin time/INR (international normalized ratio), bilirubin, ALT and AST levels).

Example 14

Materials and Methods for Examples 15-21

Because GC-1 is of relevance as regenerative therapy both in transplantation settings, it is pertinent to directly address its effect on tumor growth and development, especially those that are driven by the Wnt/β-catenin signaling pathway. The effect of GC-1 on liver tumor cells, and in a HCC model driven by the co-expression of S45Y-β-catenin and hMet using SBTT and HTVI (Tao et al., Hepatology 2016, 64:1587-605), was assessed. It was demonstrated that GC-1 decreased tumor burden owing to decreased tumor cell proliferation with a notable decrease in Met-Erk and Met-Stat3 signaling and no effect on Akt or Wnt/β-catenin signaling. Thus, GC-1 suppresses tumorigenesis and does not enhance Wnt/β-catenin in HCC, demonstrating its overall safety for use in chronic liver diseases and after transplantation, to induce regeneration.

The following materials and methods were used in these studies:

Animals, Plasmids and Hydrodynamic Tail Vein Injections.

SBTT plasmids and HTVI have been described previously (Tao et al., Hepatology 2016, 64:1587-605). Briefly, 20 μg pT3-EF5α-hMet-V5 and pT3-EF5α-S45Y-β-catenin-Myc combination along with the transposase in a ratio of 25:1 were diluted in 2 ml of normal saline (0.9% NaCl), filtered through 0.22 μm filter (Millipore), and injected into the lateral tail vein of 23 FVB mice that were around 6-week-old, in 5-7 seconds. These mice are referred henceforth as hMet-mutant-β-catenin mice. Four weeks after injection, hMet-mutant-β-catenin mice were randomized into two groups. One group was kept on basal diet (n=12) and another group was switched to GC-1-supplemented diet (5 mg/kg of diet, Medchem Express) (n=11). Animals on control diet were sacrificed at either 21 days (n=8) or 10 days (n=4) after initiation of diet. Similarly, animals on GC-1-diet were sacrificed at either 21 days (n=7) or 10 days (n=4) after initiation of the diet. The animals were given access to food and water ad libitum with a 12-hour light/dark daily cycle. One intraperitoneal injection of BrdU was performed on day 9 during 10 days of GC-1 or basal diet treatment and livers were harvested 24 hours later. Guidelines for the Care and Use of Laboratory Animals were followed.

Immunohistochemistry.

Four micron formalin-fixed sections were deparaffinized in graded xylene and alcohol and rinsed in PBS. To block endogenous peroxidase activity, the sections were incubated in 3% hydrogen peroxide (Sigma). For antigen retrieval, slides were microwaved in citrate buffer followed by blocking with Superblock (ScyTek Laboratories, Logan, Utah) for 10 minutes. Sections were incubated overnight at 4° C. or 1 hour room temperature in the following antibodies: cyclin-D1 (Thermo-Scientific, Fremont, Calif.), Glutamine synthetase, Ki-67, Myc-tag and CD45 (Santa Cruz Biotechnology, Dallas, Tex.). Sections were then incubated with species-specific secondary horseradish peroxidase-conjugated antibody for 30 minutes at room temperature. Sections stained with antibodies were incubated with streptavidin-biotin and signal was detected with DAB. Cell death was evaluated in liver sections by terminal deoxynucleotidyl transferase dUTP nick end labeling (TUNEL) using manufacturer's instructions available with the kit (EMD-Millipore). BrdU was stained with mouse antibody (Becton Dickinson, Franklin Lakes, N.J.) as previously described (Alvarado et al., Gene Expr 2016, 17:19-34). Briefly, tissue sections were deparaffinized, exposed to 0.3% hydrogen peroxide in deionized water for 10 minutes to block endogenous peroxidase, treated with 2N HCl, incubated with trypsin 0.1% for 20 minutes and then with normal goat serum for 20 minutes at room temperature. Sections were then incubated overnight in cold room with anti-BrdU monoclonal antibody, followed by biotinylated goat anti-mouse IgG. DAB kit was then applied, and sections were counterstained with hematoxylin.

For quantification of Ki-67 immunohistochemistry (IHC), pictures were taken at 200× magnification from either tumor or non-tumor areas in the same slide. Each picture was separated into DAB staining channel and hematoxylin staining channel by Color Deconvolution using Imagej Fiji. To quantify the number of Ki-67 positive nuclei on each picture, the DAB staining on the DAB channel was highlighted with the threshold of 48 and then quantified with Analyze Particles. All particles of areas smaller than 100 pixels were excluded. To quantify the total number of nuclei on each picture the hematoxylin staining on the hematoxylin channel was highlighted with the threshold of 205 and then quantified with Analyze Particles with similar exclusion of small areas. The percentage of Ki-67-positive nuclei on each picture was calculated by dividing the number of particles counted from DAB channel by the number of particles counted from the hematoxylin channel.

Protein Extraction and Western Blot Analysis.

Flash-frozen livers from hMet-mutant-β-catenin FVB mice on control/basal diet or GC-1-diet were used to obtain whole cell lysates. For protein extraction, a small amount of liver tissue was homogenized using RIPA buffer containing the protease and phosphatase inhibitor cocktail (Sigma, St. Louis, Mo.). Tissue homogenate was centrifuged at 14,000 RPM for 5 minutes in cold room. Supernatant was recovered and stored at −80° C. for use. Aliquots of 30-50 μg of proteins were denatured by boiling in Tris-Glycine SDS Sample Buffer (Life Technologies, Carlsbad, Calif.), resolved by SDS PAGE, and transferred to PVDF membranes (Life Technologies) using the Biorad transfer apparatus. Membranes were blocked in 5% non-fat dry milk or 5% BSA in Tris-buffered saline containing 0.1% Tween 20 for 1 hour. Western blot analysis was performed using the following primary antibodies Active-β-catenin (1:800, Cell Signaling, Danvers, Mass.), cyclin-D1 (1:1000, Thermo-Scientific), GS (1:2000, Santa Cruz Biotechnology), ERK1/2 (1:1000, Cell Signaling), P-ERK1/2 (T202, Y204) (1:1000, Cell Signaling), P-MET (Y1234/1235) (1; 1:500, Cell Signaling CST 3077S), P-MET (Y1234/1235) (2; 1:500, Cell Signaling CST 3129S), Total MET (1:500, Cell Signaling), STAT3 (1:500, Santa Cruz), P-STAT3 (Y705) (1:100, Cell Signaling), AKT (1:1000, Cell Signaling) and P-AKT (S475) (1:1000, Cell Signaling). Membranes were incubated in primary antibodies, diluted in 5% skim milk or 5% BSA following overnight incubation at 4° C. Incubation with anti-rabbit or anti-mouse secondary antibody horseradish peroxidase-conjugated immunoglobulin G (IgG; Santa Cruz Biotechnology, Santa Cruz, Calif., USA) was done for 30 minutes at room temperature. Immunoreactive bands were detected by Super-Signal West Pico Chemiluminescense Substrate (ThermoFisher Scientific, Rockford Ill.) and revealed by autoradiography.

Real Time Polymerase Chain Reaction (RT-PCR).

Isolation of total RNA was performed using Trizol reagent (Invitrogen, Carlsbad, Calif.), from frozen liver tissue. Aliquots containing 21 μg of total RNA were reverse-transcribed after DNAse enzymatic treatment to remove genomic DNA contamination, using Super Script III first strand kit (ThermoFisher Scientific). Real-time PCR was performed on an ABI Prism 7300 Sequence Detection System (Applied Biosystems, Foster City, Calif.) using Sybrgreen. Deiodinase I values were normalized to GAPDH.

TopFlash Reporter Assay.

Three liver tumor cell lines Hep3B, HepG2 and Snu-398 cells were obtained from ATCC (Manassas, Va.). Cells were transfected simultaneously with *Renilla reniformis* luciferase (pRL-TK; Promega, Madison, Wis.) as a transfection control and TopFlash firefly luciferase plasmids (Upstate Biotechnology, Lake Placid, N.Y.), which contains three copies of the Tcf/Lef sites upstream of a thymidine kinase (TK) promoter and the firefly luciferase gene using Lipofectamine 2000 (Life Technologies). Twenty-four hours after transfection, cells were treated with either DMSO (Fisher Scientific) or 5-7 μM GC-1 (Medchem Express, Monmouth Junction, N.J.) for 24 hours. Lysates were harvested using the Dual-Luciferase Reporter Assay System (Promega, Madison, Wis.). Firefly luciferase signals were normalized to *Renilla* luciferase and ratio between groups compared by student's t-test to determine significance. $P<0.05$ was considered significant.

Statistical Analysis.

All statistics were performed using the Prism 6 for Mac OS X software (Version 6) (GraphPad Software, Inc.) and the comparison between treated and control group was performed by Student's t test. $P<0.05$ was considered significant (*), $p<0.01$ was considered highly significant () and $p<0.001$ was considered extremely significant (*).

Example 15

GC-1 Treatment does not Enhance β-Catenin-TCF4 Reporter Activity in CTNNB1-Mutated and Non-Mutated Human HCC Cells GC-1 has been found to stimulate hepatocyte proliferation at least in part through the activation of Wnt/β-catenin signaling (Alvarado et al., Gene Expr 2016, 17:19-34; Fanti et al., Hepatology 2014, 59:2309-20). Since Wnt/β-catenin activation due to mutations in key effectors of the pathway is reported in a significant subset of HCC cases, it was addressed if GC-1 could promote β-catenin-TCF4 activity in various liver tumor cells. The effect of GC-1 treatment was directly examined on three different liver tumor cell lines which normally contain wild-type CTNNB1 (Hep3B cells), point-mutant β-catenin (Snu-398 cells) and exon-3-deletion mutant of CTNNB1 (HepG2 cells). TopFlash reporter-transfected cells were treated for GC-1 as indicated in methods. GC-1 treatment had no significant effect on the TopFlash luciferase reporter activity in any of the three cell lines as compared to the respective DMSO-treated controls (FIGS. 10 A-10F). Thus, irrespective of the status of β-catenin gene mutations, GC-1 does not increase or decrease Wnt/β-catenin activity in various HCC cell lines.

Example 16

Figure 12A:
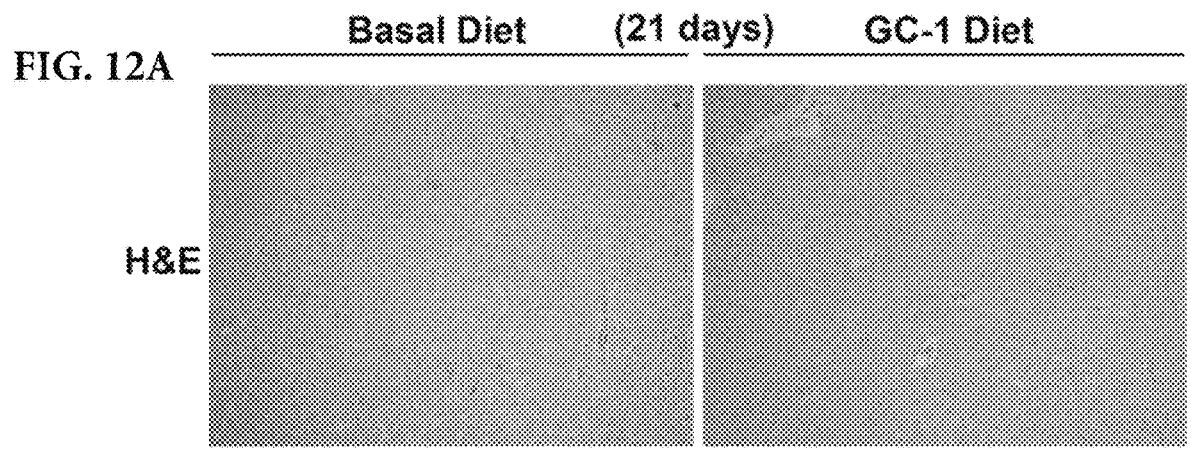
Figure 12B:
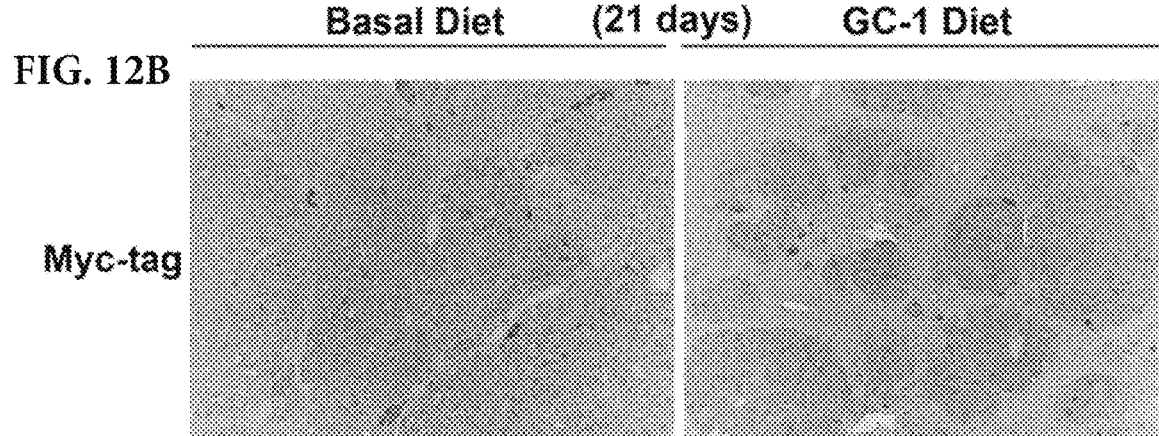
Figure 12C:
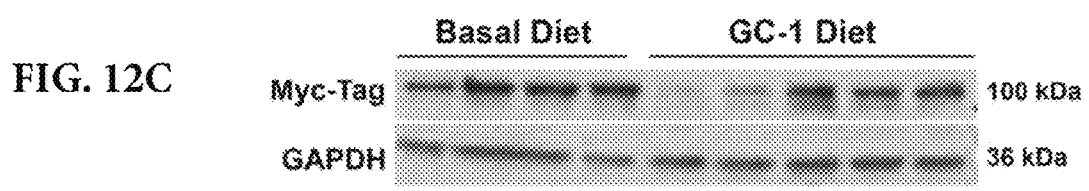

Three-Week Treatment with GC-1 Decreases Tumor Burden in hMet-S45Y-β-Catenin HCC Model by Decreasing Tumor Cell Proliferation To further address any effect of GC-1 on HCC in vivo in a model which represents a clinical disease, and is driven by combination of two proto-oncogenes—mutant-CTNNB1 and hMet, a recently described murine model (Tao et all, Hepatology 2016, 64:1587-605) was employed. hMet-S45Y-β-catenin mice were randomized into two groups, one received basal and another GC-1-diet for 21 days (FIG. 11A). The effectiveness of GC-1 was verified by examining hepatic expression of deiodinase 1 (Dio1) gene, a surrogate target of THR3 (Bianco et al., J Clin Invest 2006, 116:2571-9; Gullbeg et al., Mol Endocrinol 2002, 16:1767-77), which was significantly upregulated in GC-1-treated group by RT-PCR (FIG. 11B). GC-1's effect on overall tumor burden was next assessed by comparing the liver weight to body weight ratios (LW/BW×100; percent) in the two groups. An almost significant decrease (p=0.0506) in LW/BW was evident in the GC-1 group (FIG. 11C). Grossly, most livers from basal diet group showed large tumors and irregular surface depicting notable tumorigenesis, while all livers from GC-1 treated groups showed relatively smooth surface and smaller nodules (FIG. 11D). H&E staining of livers from basal diet-fed mice after 7 weeks of HTVI showed several abutting tumor foci with only a few layers of normal hepatocytes compressed in between (FIG. 12A). This was clearly evident in immunohistochemistry (IHC) for Myc-tag in these liver sections (FIG. 12B), as also shown previously (Tao et al., Hepatology 2016, 64:1587-605). The GC-1 diet-fed hMet-S45Y-β-catenin mice showed notably smaller tumor nodules interspersed among normal hepatocytes as seen by both H&E and Myc-tag IHC (FIGS. 12A-12B). A modest decrease in Myc-tag levels by Western blot (WB) analysis also verified overall lower tumor burden in these group of animals (FIG. 12C).

Figure 12D:
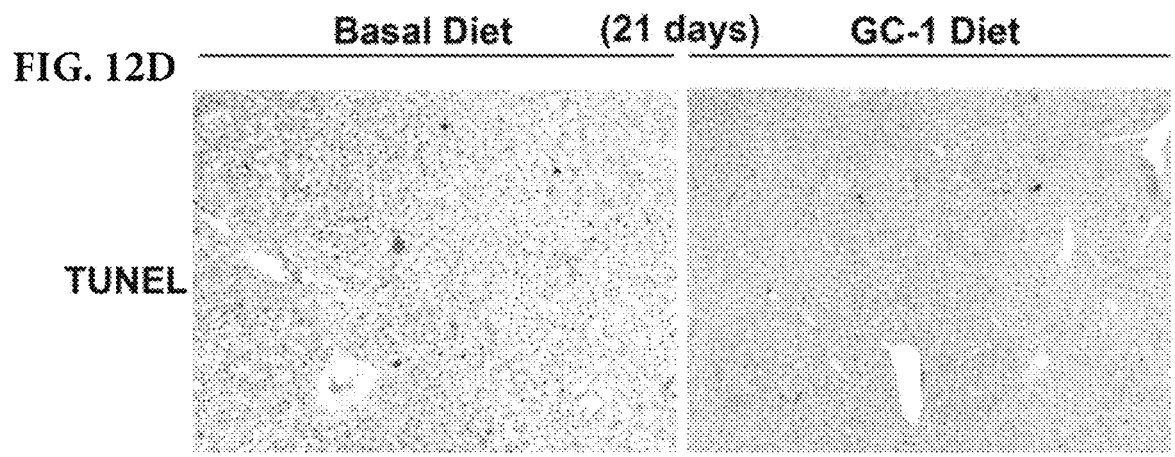

To address the basis of smaller tumor foci in hMet-S45Y-β-catenin mice after GC-1 versus control diet, a terminal deoxynucleotidyl transferase dUTP nick end labeling (TUNEL) was performed as a marker of cell death. More TUNEL-positive cells were evident in the basal diet group as compared to GC-1 group likely due to excessive tumor size, precluding increased cell death to be mechanism of lower tumor burden (FIG. 12D).

Next, IHC for Ki-67, marker of cells in S-phase of cell cycle, was performed. While tumor nodules were smaller in the liver sections of the GC-1 treated group, several cells were positive for Ki-67 staining within the tumor nodules as compared to basal diet, where relatively fewer tumor cells within large nodules were positive (FIG. 13A). Quantification of Ki-67 IHC revealed insignificant differences in the percentage of positive tumor cells within nodules between the two groups (FIG. 13B). Likewise, non-tumor areas of both group showed scant KI-67-positive cells and differences between GC-1 and basal diet group were insignificant (FIG. 13B).

Example 17

Three-Week Treatment with GC-1 in hMet-S45Y-β-Catenin HCC Model does not Impact Wnt Signaling To address the molecular basis of reduced tumor burden, it was first assessed if GC-1 could have any paradoxical and negative effect on Wnt signaling pathway since it is known to promote Wnt signaling in the context of cell proliferation and liver regeneration (Alvarado et al., Gene Expr 2016, 17:19-34; Fanti et al., Hepatology 2014, 59:2309-20). The status of tumor nodules was assessed in each group for Wnt/β-catenin pathway targets such as cyclin-D1 and Glutamine synthetase (GS) by IHC. Tumor nodules in basal diet group were strongly positive for cyclin-D1 as were the nodules in GC-1 diet, despite being smaller in the latter group (FIG. 14A). Cyclin-D1 was localized to both tumors as well as surrounding normal tissue in both groups. The tumors were uniformly and comparably positive for GS by IHC in both groups despite the smaller size of nodules in the GC-1 group (FIG. 14B). GS was localized mostly in the tumors in both groups.

To validate IHC findings, Western Blot (WB) analysis was performed on lysates from tumor-bearing livers from both groups for Wnt signaling components. Total and active β-catenin levels remained unaltered in the two groups (FIG. 14C). Similarly, no change in cyclin-D1 levels were evident by WB (FIG. 14C). A modest decrease in GS levels by WB in the GC-1 group may also represent a decrease in tumor burden since like Myc-tag, GS was predominantly expressed in tumor nodules only (FIG. 14C). Thus, GC-1 had no impact on Wnt/β-catenin signaling in hMet-S45Y-β-catenin mice and did not increase this signaling pathway or promote hepatocellular carcinoma (HCC) burden.

Example 18

Three-Week Treatment with GC-1 in hMet-S45Y-β-Catenin HCC Model Impairs Met-Erk and Met-Stat3 Signaling Because HCC in the hMet-S45Y-β-catenin mice is due to functional and synergistic cooperation of the two proto-oncogenes (Tao et al., Hepatology 2016, 64:1587-605) and because GC-1 did not alter Wnt signaling, its effect was next tested on Met signaling. A dramatic decrease in p-Met (Tyr 1234/1235) was observed in GC-1-treated group as compared to the basal diet controls (FIG. 15A). Total Met levels were only marginally and variably decreased after GC-1 treatment (FIG. 15A).

Since Met signaling was recently shown to predominantly act through downstream Ras-Erk signaling, and cooperate with mutant-β-catenin in the development of HCC (Tao J, Zhang R, Singh S, Poddar M, Xu E, Oertel M, Chen X, Ganesh S, Abrams M, Monga S P: Targeting beta-catenin in hepatocellular cancers induced by coexpression of mutant beta-catenin and K-Ras in mice. Hepatology 2016, the levels of both total and p-ERK were assessed. Both total and p-ERK1 and total and p-ERK2 were notably decreased following GC-1 treatment (FIG. 15B). p-AKT levels showed comparable levels in the two groups (FIG. 15C). There was however, a striking decrease in p-STAT3 levels following GC-1 treatment (FIG. 15C). Thus GC-1 treatment led to a notable decrease in Met-ERK and Met-Stat3 signaling to affect overall tumor burden in the hMet-S45Y-β-catenin mice.

Example 19

Ten-Day Treatment with GC-1 Decreases Tumor Burden in hMet-S45Y-β-Catenin HCC Model by Decreasing Tumor Cell Proliferation To further validate the mechanism of GC-1 on tumorigenesis in the hMet-S45Y-β-catenin mouse model of HCC, a short-term GC-1 treatment was performed as described in methods and shown in FIG. 16A. Hepatic expression of Dio1 was significantly increased in the 10-day GC-1 versus control group (FIG. 16B).

To address effect of GC-1 on tumor burden, LW/BW was compared between the two groups. A significant decrease (p=0.0022) in LW/BW was evident after GC-1 treatment (FIG. 16C). Grossly, the livers from basal diet and GC-1 diet groups looked indistinguishable and without gross tumor nodules (FIG. 16D). H&E staining of liver sections showed several small well-differentiated tumor foci composed of cells with basophilic cytoplasm and some nuclear atypia (FIG. 17A). Staining for Myc-tag confirmed presence of several tumor foci spread throughout liver sections (FIG. 17A). Smaller and fewer tumor foci were apparent in the GC-1 diet fed group as observed by H&E and Myc-tag staining, although histological features of tumors were not altered (FIG. 17A).

To address the basis of reduced tumor burden, the livers from both groups were compared for TUNEL. Comparable numbers of TUNEL-positive cells were evident between the two groups (FIG. 17B). No differences in the number of CD45-positive between the two groups were observed suggesting that intra- and extra-tumoral inflammation is unaffected by GC-1 (FIG. 17C).

Any effect of 10-day treatment of GC-1 on cell proliferation was assessed by IHC for BrdU and Ki-67. A notable decrease in both markers was evident within the tumor foci in the GC-1-treated group (FIG. 18A-18B). Quantification revealed a significant decrease in the percentage of Ki-67-positive cells within tumor nodules after GC-1 treatment (FIG. 18C). No differences in Ki-67-positive cell numbers were observed in non-tumor areas between basal- and GC-diet (FIG. 18C).

Example 20

Ten-Day Treatment with GC-1 in hMet-S45Y-β-Catenin HCC Model does not Impact Wnt Signaling To investigate if there was any effect of short term GC-1 treatment on the Wnt/β-catenin signaling, IHC was performed for cyclin-D1 and GS. Tumor nodules in basal diet group were strongly and uniformly positive for cyclin-D1 as well as GS (FIGS. 19A-19B). After GC-1 treatment for 10 days, tumors continued to be positive for cyclin-D1 as well as GS although a notable diminution in number and size of tumor foci was visible (FIGS. 19A-19B). Both GS and cyclin-D1 were predominantly localized the tumor foci.

Protein expression of total and active β-catenin was examined, along with cyclin-D1 and GS levels, by WB using the liver lysates from both groups. A modest decrease in the levels of total but not active β-catenin were observed in 10 days GC-1-diet groups (FIG. 19C). Similarly, marginal decreases in cyclin-D1 and modest decreases in GS levels by WB were evident in the GC-1 group (FIG. 19C).

IHC and WB results together suggest that the seeming reduction in the Wnt signaling following GC-1 may be actually be the result of, and not the cause of, overall decreased tumor burden, because cyclin-D1 and GS continued to be mostly expressed in the tumor foci in both control and treatment groups. Thus, short term GC-1-treatment also did not impact Wnt/β-catenin signaling and did not induce it to promote HCC burden.

Example 21

Ten-Day Treatment with GC-1 in hMet-S45Y-β-Catenin HCC Model Impairs Met-Erk and Met-Stat3 Signaling To further validate the impact on Met-Erk and Met-Stat3 signaling, liver lysates from 10-day GC-1 treated or control group were assessed. Total Met levels were modestly decreased after GC-1 treatment (FIG. 20A). A profound decrease by in p-Met (Tyr 1234/1235) was observed in the GC-1-treated group and validated by two independent antibodies (FIG. 20B). Likewise, while total ERK levels were unaffected, both p-ERK1 and p-ERK2 were dramatically decreased following GC-1 treatment as compared to the controls (FIG. 20C). GC-1 treatment did not have any effect on p-AKT levels, however a profound decrease in p-STAT3 was evident (FIG. 20C). Thus, GC-1 affects Met-ERK and Met-Stat signaling to reduce tumor burden in the hMet-S45Y-β-catenin mice.

There is a major unmet clinical need in the field of hepatic regenerative medicine as there are limited options for acute or chronic hepatic insufficiency which will ultimately progress to end stage liver disease. Treatment of end stage liver disease is often liver transplantation, however, a shortage of organs for transplantation necessitates further methods (Collin de l'Hortet et al., American Journal of transplantation 2016, 16:1688-96). T3 and GC-1 induce cell proliferation through upregulation of cyclin-D1 (Ledda-Columbano et al., FASEB J 2006, 20:87-94; Pibiri et al., FASEB J 2001, 15:1006-13) which in the liver, depends on Wnt/β-catenin signaling and PKA-dependent β-catenin activation (Alvarado et al., Gene Expr 2016, 17:19-34; Fanti et al., Hepatology 2014, 59:2309-20). Also, β-catenin signaling is normally activated during regeneration after acetaminophen-induced hepatic injury or after partial hepatectomy, and β-catenin stabilization itself promotes liver regeneration (Apte et al., Am J Pathol 2009, 175:1056-65; Bhushan et al., Developmental biology 2008, 320:161-74; Monga, Gene Expr 2014, 16:51-62, Nejak-Bowen et al., Hepatology 2010, 51:1603-13). GC-1 pretreatment before partial hepatectomy accelerated cyclin-D1 expression after the surgery and led to an earlier transition of hepatocytes into S-phase during liver regeneration (Alvarado et al., Gene Expr 2016, 17:19-34).

Chronic hepatic injuries can benefit from regenerative therapies to sustain and even expand the residual functional hepatocyte mass. However, chronic hepatic injuries like viral hepatitis, non-alcoholic or alcoholic hepatitis and others, often and over an extended time period, lead to progressive fibrosis with regenerative nodules that maintain liver function and often complicated by acute-on-chronic liver failure (Sarin et al., Nature reviews Gastroenterology & hepatology 2016, 13:131-49). As injury progresses and cirrhosis ensues, the risk for development of HCC also increases. Thus, it is pertinent to directly address the effect of a regenerative therapy on HCC to especially demonstrate that it does not worsen the growth and development of hepatic tumors. This is relevant for GC-1, which induces activation of β-catenin in normal liver to induce regeneration (Alvarado et al., Gene Expr 2016, 17:19-34). β-catenin activation due to mutations in CTNNB1 is a common event in HCC (Columbano et al., Endocrinology 2006, 147:3211-8).

In vitro studies using three different cell lines with varying status of β-catenin gene mutations and associated Wnt/β-catenin activity, showed no effect of GC-1 on β-catenin-TCF4 activity. Furthermore, GC-1 never increased TopFlash activity in any of the liver tumor lines irrespective of CTNNB1 mutational status. While basal luciferase activity in the three cell lines used was commensurate with CTNNB1 mutational status, such that HepG2 cells (exon-3 deletion) had the highest, Snu-398 cells (missense mutation in exon-3) the next highest, and Hep3B cells (wild-type) the lowest, GC-1 treatment did not alter the respective basal β-catenin-TCF4 activity.

To validate lack of effect of GC-1 on β-catenin-TCF4 activity and to investigate any effect of GC-1 on tumor growth and development in vivo, a clinically relevant model was utilized that represents 10% of human HCC (Tao et al., Hepatology 2016, 64:1587-605). Stable expression of mutant β-catenin and hMet in a subset of hepatocytes in mice leads to HCC, which partially β-catenin-addicted. Administration of GC-1 for 10 or 21 days to these mice, once tumors were established, did not promote Wnt/β-catenin signaling in hepatic as shown by unaltered levels of total- and active-(hypophosphorylated) β-catenin along with its targets GS and cyclin-D1. In fact, no difference in the localization or intensity of cyclin-D1 or GS within existing tumor nodules was observed after GC-1 treatment as compared to the controls fed normal diet. This was in contrast to the lipid nanoparticles used to deliver siRNA against CTNNB1, which suppressed β-catenin expression, inhibited downstream signaling as demonstrated by the lack of GS and cyclin-D1 in tumor nodules, and dramatically inhibited tumor growth in a related HCC model. Thus, GC-1 did not alter (did not increase) β-catenin activity in HCC in vivo in the hMet-β-catenin model (FIG. 21).

Despite the lack of effect on Wnt signaling, GC-1 treatment decreased overall HCC burden in this model. This was desirable, as GC-1 use could not only induce regeneration but could affect tumorigenesis in chronic liver diseases (FIG. 21). Indeed, despite its mitogenic capacity, T3 was previously shown to accelerate remodeling of chemically-induced preneoplastic lesions in rats subjected to the resistant-hepatocyte model of hepatocarcinogenesis (Ledda-Columbano et al., Cancer Res 2000, 60:603-9). GC-1 was shown to also negatively influence the carcinogenic process through an induction of a differentiation program within preneoplastic hepatocytes based on analysis of molecular markers (Perra et al., Hepatology 2009, 49:1287-96). In the study disclosed herein, the previously unrecognized effect of GC-1 on inhibiting Met phosphorylation was identified. Both at 10 days and 21 days, GC-1 treatment profoundly suppressed Met-phosphorylation and modestly decreased total Met levels. Met phosphorylation and activation in the hMet-β-catenin model is due to Met overexpression, which leads to activation of Met signaling via autophosphorylation at Y1234/1235. GC-1 inhibited Met phosphorylation at these residues, which in turn impacted p-ERK1 and p-ERK2 as well as p-STAT3, without impacting P-AKT (FIG. 21).

The studies demonstrated that the use of GC-1 in chronic liver diseases to induce regeneration was safe, and could be advantageous due to the tumor inhibitory effect.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for increasing hepatocyte cell number and mass in a liver transplant in a subject, comprising
selecting a subject that is the recipient of a liver transplant;
administering to the subject an effective amount of a pharmaceutical composition comprising GC-1 (sobetirome) or a pharmaceutically acceptable salt thereof, wherein the pharmaceutical composition is administered to the subject within one day after liver transplantation and is continued for at most three weeks following the liver transplantation;
thereby increasing hepatocyte cell number and mass in the liver transplant in the subject.

2. The method of claim 1, wherein the subject has small for size syndrome (SFSS).

3. The method of claim 1, wherein the subject is the recipient of a cadaveric liver transplant.

4. The method of claim 1, wherein the subject is the recipient of a liver transplant from a living donor.

5. The method of claim 3, wherein the subject is a high risk donor.

6. The method of claim 5, wherein the subject is older than about 45 years of age.

7. The method of claim 1, wherein the GC-1 or the pharmaceutically acceptable salt thereof is administered intravenously to the subject.

8. The method of claim 7, wherein the GC-1 or the pharmaceutically acceptable salt thereof is administered at a dose of 0.1 mg/kg to about 0.5 mg/kg.

9. The method of claim 8, the GC-1 or the pharmaceutically acceptable salt thereof is administered at a dose of 0.3 mg/kg.

10. The method of claim 1, wherein the GC-1 or the pharmaceutically acceptable salt thereof is administered orally to the subject.

11. The method of claim 1, wherein the GC-1 or the pharmaceutically acceptable salt thereof is administered for at most 14 days after liver transplantation.

12. The method of claim 1, further comprising monitoring the metabolic function of the liver in the subject.

13. The method of claim 1, further comprising measuring liver size in the subject.

14. The method of claim 1, further comprising obtaining a lipid profile of the subject.

15. The method of claim 1, wherein the subject is human.

16. The method of claim 1, wherein the subject has overdosed on acetaminophen.

17. The method of claim 3, wherein the GC-1 or the pharmaceutically acceptable salt thereof is administered within one day of a resection procedure.

18. The method of claim 1, wherein the subject is the recipient of a liver transplant from a living donor, the GC-1 is administered orally, and the subject is human.

19. The method of claim 1, wherein hepatocyte proliferation is measured by radiological monitoring of hepatic size in the subject.

20. The method of claim 1, further comprising measuring an increase in hepatocyte cell number in the subject.

* * * * *